(12) United States Patent
Ali et al.

(10) Patent No.: US 8,563,567 B2
(45) Date of Patent: Oct. 22, 2013

(54) SUBSTITUTED HETEROCYCLIC COMPOUNDS

(75) Inventors: Syed M. Ali, North Andover, MA (US); Mark A. Ashwell, Carlisle, MA (US); Yanbin Liu, Acton, MA (US); Magdi Moussa, Malden, MA (US); Jianqiang Wang, Acton, WA (US); Hui Wu, Malden, MA (US)

(73) Assignee: ArQule, Inc., Woburn, MA (US)

( * ) Notice: Subject to any disclaimer, the term of this patent is extended or adjusted under 35 U.S.C. 154(b) by 183 days.

(21) Appl. No.: 12/981,095

(22) Filed: Dec. 29, 2010

(65) Prior Publication Data

US 2011/0160237 A1 Jun. 30, 2011

Related U.S. Application Data

(60) Provisional application No. 61/290,932, filed on Dec. 30, 2009, provisional application No. 61/290,904, filed on Dec. 30, 2009.

(51) Int. Cl.
| | | |
|---|---|---|
| *A61K 31/505* | (2006.01) | |
| *A61K 31/44* | (2006.01) | |
| *C07D 401/04* | (2006.01) | |
| *C07D 413/04* | (2006.01) | |
| *C07D 453/06* | (2006.01) | |

(52) U.S. Cl.
USPC .............. 514/275; 514/294; 544/331; 546/94

(58) Field of Classification Search
USPC ....................... 514/275, 294; 546/94; 544/331
See application file for complete search history.

(56) References Cited

U.S. PATENT DOCUMENTS

| 4,522,811 A | 6/1985 | Eppstein et al. |
|---|---|---|
| 6,441,020 B1 | 8/2002 | Quick et al. |
| 2006/0223760 A1 | 10/2006 | Li et al. |
| 2009/0105166 A1 | 4/2009 | Ashwell et al. |
| 2010/0178291 A1* | 7/2010 | Wang et al. ................. 424/133.1 |

FOREIGN PATENT DOCUMENTS

| CN | 101302216 A | 11/2008 |
|---|---|---|
| DE | 4128015 A1 | 2/1993 |
| EP | 300541 A1 | 1/1989 |
| EP | 322016 A1 | 6/1989 |
| EP | 327307 A2 | 8/1989 |
| EP | 347980 A1 | 12/1989 |
| EP | 375045 A1 | 6/1990 |
| EP | 384349 A1 | 8/1990 |
| EP | 393766 A2 | 10/1990 |
| EP | 403261 A2 | 12/1990 |
| EP | 414023 A2 | 2/1991 |
| EP | 1336406 A1 | 8/2003 |
| JP | 09040557 A | 2/1997 |
| WO | WO-9012569 A1 | 11/1990 |
| WO | WO-9514668 A1 | 6/1995 |
| WO | WO-0144235 A2 | 6/2001 |
| WO | WO-0144247 A2 | 6/2001 |
| WO | WO-02060871 A2 | 8/2002 |
| WO | WO-02066472 A1 | 8/2002 |
| WO | WO-03076442 A1 | 9/2003 |
| WO | WO-2006086484 A1 | 8/2006 |
| WO | WO-2007139569 A1 | 12/2007 |
| WO | WO-2009002806 A1 | 12/2008 |
| WO | WO-2009002807 A2 | 12/2008 |
| WO | WO-2009026446 A2 | 2/2009 |

OTHER PUBLICATIONS

Al-awar et al. "1,7-Annulated indolocarbazoles as cyclin-dependent kinase inhibitors", Bioorganic & Medicinal Chemistry Letters (2004), 14(12), 3217-3220.

Grandberg et al., "Indoles. XXXVI. Synthesis of 2-unsubstituted tryptamines", Khimiya Geterotsiklicheskikh Soedinenii (1973), (2), 213-18.

Joule, J.A. "Product class 13: indole and its derivatives", Science of Synthesis (2001), 10, 361-652.

Isaac et al. "Pyrrolo[3,2,1-ij]quinoline derivatives, 5-HT2c receptor agonists with selectivity over the 5-HT2a receptor: potential therapeutic applications for epilepsy and obesity", Bioorganic & Medicinal Chemistry Letters (2000), 10(9), 919-921.

Katritzky et al., "General and Efficient Approaches to Fused [1,2-a]Pyrroles and [1,2-a]Indoles", Journal of Organic Chemistry (1997), 62(12), 4148-4154.

Martinet, J., "Indirubin", Compt. rend. (1919), 169, 183.

Masuda et al. "Synthetic studies of teleocidin. III. Regioselective introduction of a nitro group at the 4-position of substituted indole derivatives", Heterocycles (1987), 26(6), 1475-8.

McKittrick et al. "Synthetic entries to 6-fluoro-7-substituted indole derivatives", Journal of Heterocyclic Chemistry (1990), 27(7), 2151-63.

Moffat et al. "Comparison of Field-Based Similarity Searching Methods: CatShape, FBSS, and ROCS", Journal of Chemical Information and Modeling (2008), 48(4), 719-729.

Nakatsuka et al. "Regiospecific cyclization of 3-carbomethoxyindole-1-propanoic acid onto 7-position of the indole nucleus", Heterocycles (1986), 24(8), 2109-10.

Paris et al. "Synthesis, Structure-Activity Relationships, and Pharmacological Evaluation of Pyrrolo[3,2,1-ij]quinoline Derivatives: Potent Histamine and Platelet Activating Factor Antagonism and 5-Lipoxygenase Inhibitory Properties. Potential Therapeutic Application in Asthma", Journal of Medicinal Chemistry (1995), 38(4), 669-85.

(Continued)

*Primary Examiner* — James O Wilson
*Assistant Examiner* — Ebenezer O Sackey
(74) *Attorney, Agent, or Firm* — Mintz Levin Cohn Ferris Glovsky and Popeo, P.C.; Ivor R. Elrifi; Matthew Pavao

(57) ABSTRACT

The present invention relates to substituted heterocyclic compounds and methods of synthesizing these compounds. The present invention also relates to pharmaceutical compositions containing substituted heterocyclic compounds and methods of treating cell proliferative disorders, such as cancer, by administering these compounds and pharmaceutical compositions to subjects in need thereof.

17 Claims, No Drawings

(56) References Cited

OTHER PUBLICATIONS

Ruccia et al., "Addition reactions of heterocycles. IV. Indoles and nitrilimines", Tetrahedron (1973), 29(20), 3159-64.

Steck et al., "5,6-Dihydro-4H-pyrrolo[3,2,1-ij]quinolines", Journal of Heterocyclic Chemistry (1974), 11(3), 387-93.

Tsotinis et al. "Design, synthesis and melatoninergic activity of new unsubstituted and β, β'-difunctionalised 2,3-dihydro-1H-pyrrolo[3,2,1-ij]quinolin-6-alkanamides", European Journal of Medicinal Chemistry (2007), 42(7), 1004-1013.

Tsotinis et al. "Design, synthesis and melatoninergic potency of new N-acyl 8,9-dihydro-4-methoxy-7H-2-benzo[de] quinolinalkanamines", Bioorganic Chemistry (2007), 35(2), 189-204.

van Wijngaarden et al. "Development of high-affinity 5-HT3 receptor antagonists. Structure-affinity relationships of novel 1,7-annulated indole derivatives", Journal of Medicinal Chemistry (1993), 36(23), 3693-9.

* cited by examiner

SUBSTITUTED HETEROCYCLIC COMPOUNDS

RELATED APPLICATIONS

This application claims the benefit of U.S. Provisional Application No. 61/290,904, filed Dec. 30, 2009, and U.S. Provisional Application No. 61/290,932, filed Dec. 30, 2009, the contents of each of which are incorporated herein by reference in their entireties.

BACKGROUND OF THE INVENTION

Cancer is the second leading cause of death in the United States, exceeded only by heart disease. (*Cancer Facts and Figures* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational "mechanisms" may lead to the development of cancer. As such, heterogeneity frequently exists between cancer cells taken from tumors of the same tissue and same type that have originated in different individuals. Frequently observed mutational "mechanisms" associated with some cancers may differ between one tissue type and another (e.g., frequently observed mutational "mechanisms" leading to colon cancer may differ from frequently observed "mechanisms" leading to leukemias). It is therefore often difficult to predict whether a particular cancer will respond to a particular chemotherapeutic agent (*Cancer Medicine*, 5$^{th}$ edition, Bast et al., B. C. Decker Inc., Hamilton, Ontario).

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

Abl (c-Abl) codes for a protein that is a member of the tyrosine kinase family. The N-terminal half of Abl protein contains SH-3 and SH-2 domains. Abl has a DNA-binding domain and an F-actin-binding domain within its long C-terminal extension. C-Abl kinase is an important non-receptor tyrosine kinase involved in cell signal transduction. An abnormal form of c-Abl is known to form from a chromosomal translocation event, referred to as the Philadelphia chromosome. This abnormal chromosomal translocation leads abnormal gene fusion between the Abl kinase gene and the breakpoint cluster region (BCR) gene, thus encoding an aberrant protein called bcr-Abl.

Alterations in the activity (expression) of the Abl gene are associated with various disorders, diseases and other deleterious conditions. The altered gene expression may lead to diseases, disorders and conditions include inflammatory, proliferative, hyperproliferative and immunologically-mediated diseases. Diseases and conditions associated with Abl family tyrosine kinases also include cancers, for example, leukemia, a major cancer occurring in children in the United States. The present invention addresses these needs.

Accordingly, new compounds and methods for modulating the Abl gene and treating proliferation disorders, including cancer, are needed. The present invention addresses these needs.

SUMMARY OF THE INVENTION

The present invention provides, in part, substituted heterocyclic compounds of formula I, II, IIa, III, IIIa, IIIb, IV or V and methods of preparing the compounds of formula I, II, IIa, III, IIIa, IIIb, IV or V:

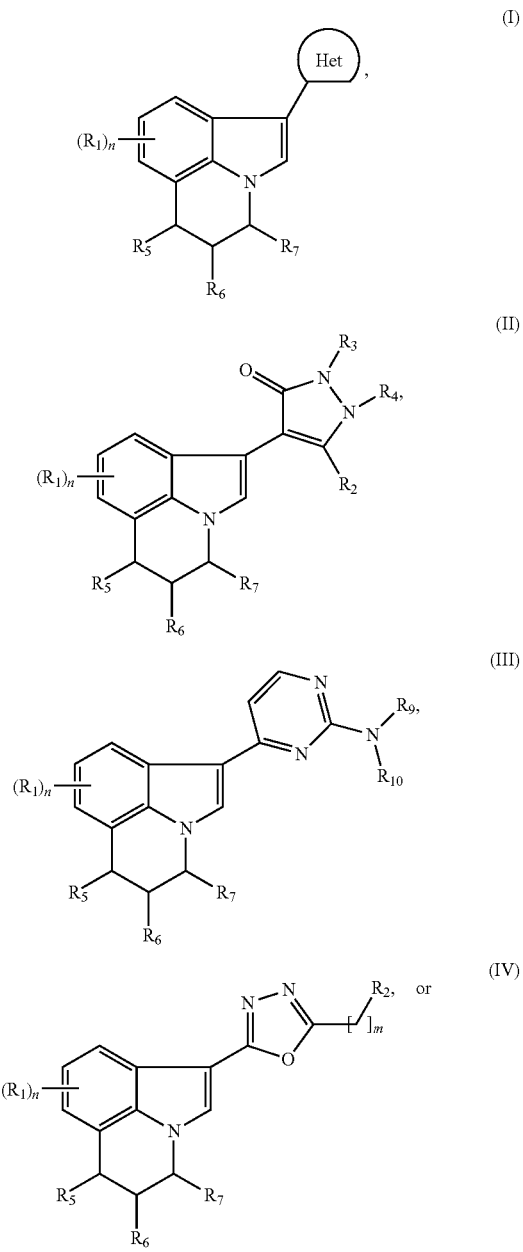

-continued

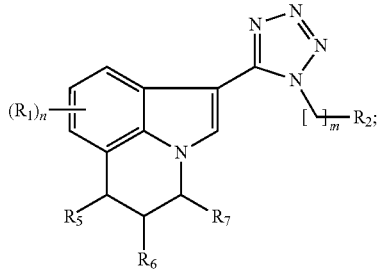

(V)

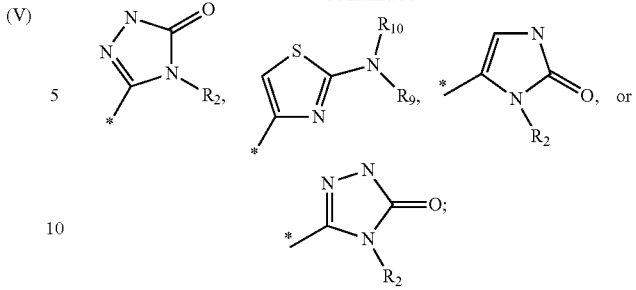

wherein:

is an optionally substituted heteroaryl or heterocycle selected from:

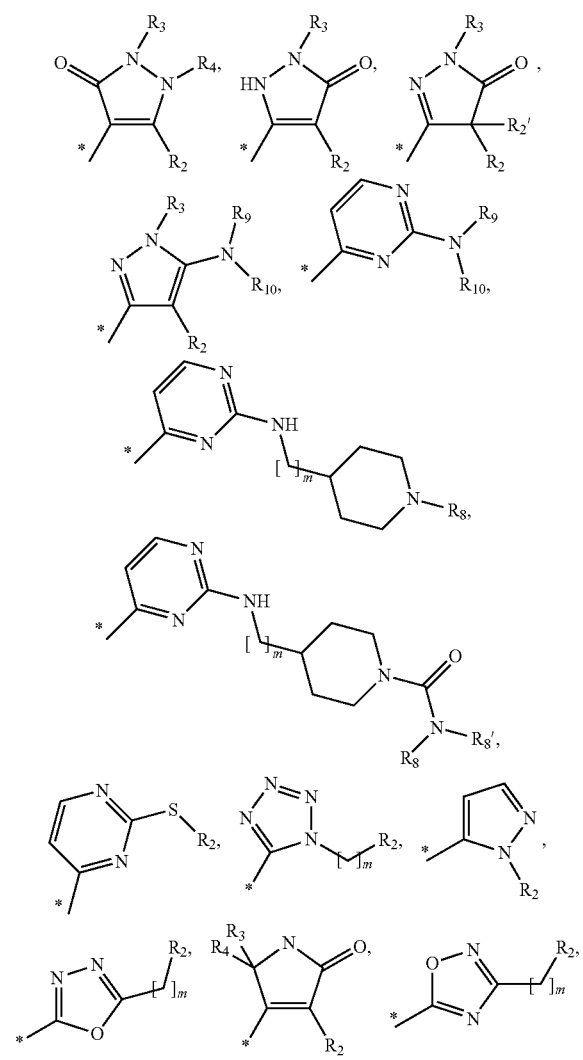

wherein "*" indicates the point of attachment of the optionally substituted heteroaryl or heterocycle;

n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ and $R_2$, are each independently H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_r$-$R_r$;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2, 5- or 6-member rings and 1-4 heteroatoms selected from N, O and S, and optionally containing unsaturation;

$R_3$, $R_4$, $R_5$, $R_6$, $R_7$ and $R_8$, are each independently H, unsubstituted or substituted $C_1$-$C_6$ alkyl, or unsubstituted or substituted $C_3$-$C_{10}$ carbocycle optionally containing unsaturation;

$R_8$ is H, unsubstituted or substituted $C_1$-$C_6$ alkyl, —C(O)$R_{11}$, —C(O)O$R_{11}$, —C(O)N$R_{11}R_{12}$, or —S(O)$_2R_{11}$;

$R_9$ and $R_{10}$ are each independently H, unsubstituted or substituted $C_1$-$C_6$ alkyl, or -$T_q$-$R_q$;

$T_q$ is unsubstituted or substituted $C_1$-$C_6$ alkyl linker, or a bond;

$R_q$ is H or unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S;

$R_{11}$ and $R_{12}$ are each independently H, unsubstituted or substituted $C_1$-$C_6$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S, or -T$_t$-R$_t$;

T$_t$ is unsubstituted or substituted C$_1$-C$_6$ alkyl linker, or a bond;

R$_t$ is H, unsubstituted or substituted C$_1$-C$_6$ alkyl, unsubstituted or substituted C$_6$-C$_{10}$ aryl, unsubstituted or substituted C$_1$-C$_6$ alkoxy, unsubstituted or substituted C$_6$-C$_{10}$ aryloxy, unsubstituted or substituted heteroaryl comprising 1 or 2, 5- or 6-member rings and 1-4 heteroatoms selected from N, O and S, unsubstituted or substituted C$_3$-C$_{10}$ carbocycle, unsubstituted or substituted heterocycle comprising 1 or 2, 5- or 6-member rings and 1-4 heteroatoms selected from N, O and S, —C(O)OR$_{13}$, or —C(O)R$_{13}$; and R$_{13}$ is H or unsubstituted or substituted C$_1$-C$_6$ alkyl;

and pharmaceutically acceptable salts, prodrugs, metabolites, analogs and derivatives thereof. The present invention also provides pharmaceutical compositions comprising one or more compounds of formula I, II, IIa, III, IIIa, IIIb, IV or V and one or more pharmaceutically acceptable carriers.

The present invention also provides methods of treating a cell proliferative disorder by administering to a subject in need thereof, a therapeutically effective amount of a compound of formula I, II, IIa, III, IIIa, IIIb, IV or V, or a pharmaceutically acceptable salt, prodrug, metabolite, analog or derivative thereof, in combination with a pharmaceutically acceptable carrier, such that the disorder is treated.

The present invention also provides methods of treating cancer by administering to a subject in need thereof, a therapeutically effective amount of a compound of formula I, II, IIa, III, IIIa, IIIb, IV or V, or a pharmaceutically acceptable salt, prodrug, metabolite, analog or derivative thereof, in combination with a pharmaceutically acceptable carrier, such that the cancer is treated.

The present invention also provides methods of selectively inducing cell death in precancerous or cancerous cells by contacting a cell with an effective amount of a compound of formula I, II, IIa, III, IIIa, IIIb, IV or V, or a pharmaceutically acceptable salt, prodrug, metabolite, analog or derivative thereof, in combination with a pharmaceutically acceptable carrier, such that contacting the cell results in selective induction of cell death in the precancerous or cancer cells.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

1. Substituted Heterocyclic Compounds

The present invention provides novel substituted heterocyclic compounds, synthetic methods for making the compounds, pharmaceutical compositions containing them and various uses of the disclosed compounds.

The present invention provides a compound of Formula I or a pharmaceutically acceptable salt, prodrug, metabolite, analog or derivative thereof:

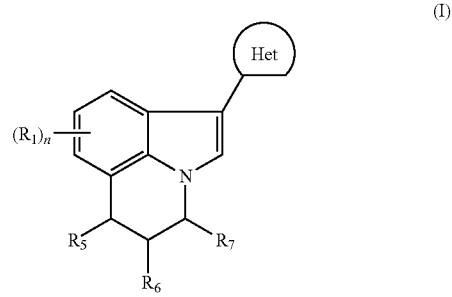

wherein:

is an optionally substituted heteroaryl or heterocycle selected from:

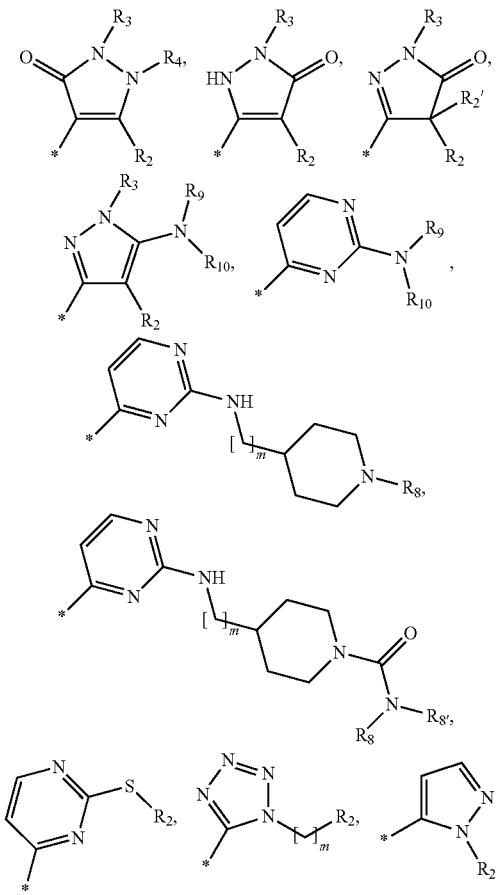

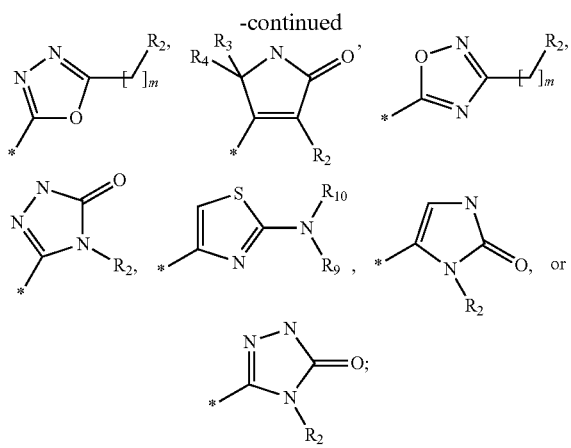

wherein "*" indicates the point of attachment of the optionally substituted heteroaryl or heterocycle;

n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ and $R_{2'}$ are each independently H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_{r'}$-$R_{r'}$;

$T_{r'}$ is unsubstituted or substituted $C_1$-$C_6$ alkyl linker, or a bond;

$R_{r'}$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2, 5- or 6-member rings and 1-4 heteroatoms selected from N, O and S, and optionally containing unsaturation;

$R_3$, $R_4$, $R_5$, $R_6$, $R_7$ and $R_{8'}$ are each independently H, unsubstituted or substituted $C_1$-$C_6$ alkyl, or unsubstituted or substituted $C_3$-$C_{10}$ carbocycle optionally containing unsaturation;

$R_8$ is H, unsubstituted or substituted $C_1$-$C_6$ alkyl, —C(O)$R_{11}$, —C(O)O$R_{11}$, —C(O)N$R_{11}R_{12}$, or —S(O)$_2R_{11}$;

$R_9$ and $R_{10}$ are each independently H, unsubstituted or substituted $C_1$-$C_6$ alkyl, or -$T_q$-$R_q$;

$T_q$ is unsubstituted or substituted $C_1$-$C_6$ alkyl linker, or a bond;

$R_q$ is H, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S;

$R_{11}$ and $R_{12}$ are each independently H, unsubstituted or substituted $C_1$-$C_6$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S, or -$T_t$-$R_t$;

$T_t$ is unsubstituted or substituted $C_1$-$C_6$ alkyl linker, or a bond;

$R_t$ is H, unsubstituted or substituted $C_1$-$C_6$ alkyl, unsubstituted or substituted $C_6$-$C_{10}$ aryl, unsubstituted or substituted $C_1$-$C_6$ alkoxy, unsubstituted or substituted $C_6$-$C_{10}$ aryloxy, unsubstituted or substituted heteroaryl comprising 1 or 2, 5- or 6-member rings and 1-4 heteroatoms selected from N, O and S, unsubstituted or substituted $C_3$-$C_{10}$ carbocycle, unsubstituted or substituted heterocycle comprising 1 or 2, 5- or 6-member rings and 1-4 heteroatoms selected from N, O and S, —C(O)O$R_{13}$, or —C(O)$R_{13}$; and $R_{13}$ is H or unsubstituted or substituted $C_1$-$C_6$ alkyl.

For example,

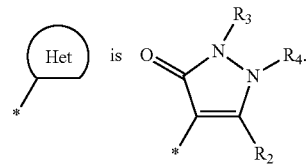

For example,

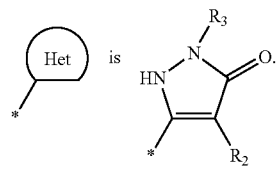

For example,

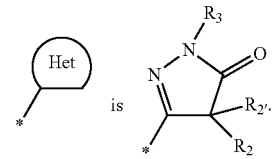

For example,

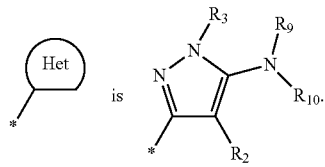

For example,
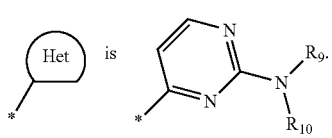
For example,
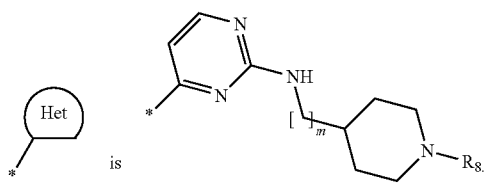
For example,
For example,
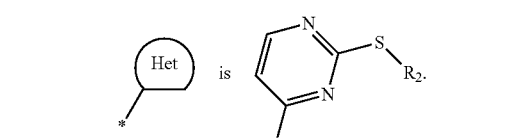
For example,
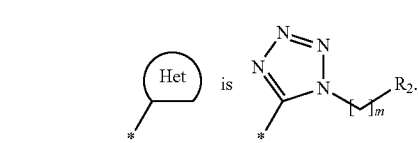
For example,
For example,
For example,
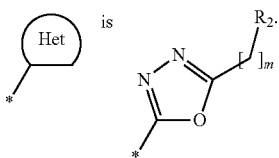
For example,
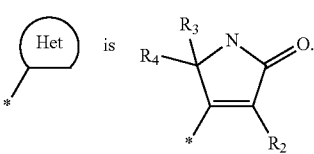
For example,
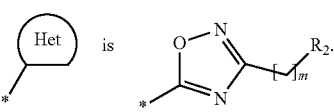
For example,
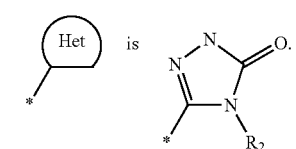
For example,
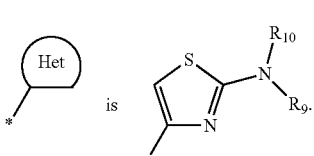
For example,
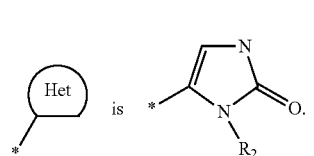
For example,
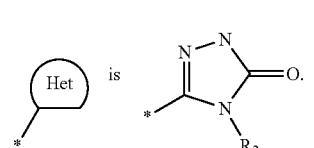
For example,

For example, n is 0.

For example, n is 1.

For example, n is 1 and $R_1$ is unsubstituted or substituted $C_1$-$C_6$ alkyl.

For example, $R_1$ is unsubstituted or substituted methyl, ethyl, n-propyl, i-propyl, n-butyl, s-butyl, t-butyl, n-pentyl, s-pentyl or n-hexyl.

For example, $R_1$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_1$ is unsubstituted or substituted methoxyl, ethoxyl, propyloxyl or iso-propyloxyl.

For example, $R_1$ is $C_1$-$C_6$ alkoxyl substituted with one or more groups, each of which can be the same or different, selected from fluorine, chlorine, bromine, and iodine.

For example, $R_1$ is fluorine, chlorine, bromine, or iodine.

For example, $R_2$ is H, and $R_{2'}$ is selected from H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_r$-$R_r$.

For example, $R_2$ is H.

For example, $R_2$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.

For example, $R_2$ is unsubstituted or substituted methyl, ethyl, n-propyl, i-propyl, or 2,2-dimethylpropyl.

For example, $R_2$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is unsubstituted or substituted phenyl or naphthyl.

For example, $R_2$ is unsubstituted or substituted phenyl or naphthyl.

For example, $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is phenyl or naphthyl substituted with one or more groups, each of which can be the same or different, selected from unsubstituted or substituted $C_1$-$C_6$ straight chain or $C_3$-$C_6$ branched alkyl.

For example, $R_2$ is phenyl or naphthyl substituted with one or more groups, each of which can be the same or different, selected from unsubstituted or substituted methyl, ethyl, n-propyl, i-propyl, n-butyl, s-butyl, and t-butyl.

For example, $R_2$ is phenyl or naphthyl substituted with one or more groups, each of which can be the same or different, selected from unsubstituted or substituted methoxyl, ethoxyl, propyloxyl and iso-propyloxyl.

For example, $R_2$ is phenyl or naphthyl substituted with one or more groups, each of which can be the same or different, selected from fluorine, chlorine, bromine, and iodine.

For example, $R_2$ is phenyl or naphthyl substituted with two or more groups, each of which can be the same or different, selected from fluorine, chlorine, bromine, and iodine.

For example, $R_2$ is phenyl or naphthyl substituted with unsubstituted or substituted di-$C_1$-$C_6$ alkylamino.

For example, $R_2$ is phenyl or naphthyl substituted with $C_1$-$C_6$ haloalkyl.

For example, $R_2$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzothiadiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, any of which may be optionally substituted with one or more groups, each of which can be the same or different, selected from hydroxyl, halogen, nitro, cyano, and unsubstituted or substituted $C_1$-$C_6$ alkyl, unsubstituted or substituted $C_1$-$C_6$ alkoxyl.

For example, $R_2$ is heteroaryl substituted with one or more groups, each of which can be the same or different, selected from unsubstituted or substituted $C_1$-$C_6$ straight chain or $C_3$-$C_6$ branched alkyl.

For example, $R_2$ is heteroaryl substituted with one or more groups, each of which can be the same or different, selected from unsubstituted or substituted methyl, ethyl, n-propyl, i-propyl, n-butyl, s-butyl, and t-butyl.

For example, $R_2$ is heteroaryl substituted with one or more groups, each of which can be the same or different, selected from fluorine, chlorine, bromine, and iodine.

For example, $R_2$ is pyridinyl, thiophenyl, isoxazolyl, benzofuranyl, benzothiophenyl, benzoimidazolyl or benzothiadiazolyl.

For example, $R_2$ is unsubstituted or substituted indolyl.

For example, $R_2$ is unsubstituted or substituted $C_1$-$C_6$ alkyl substituted indolyl.

For example, $R_2$ is unsubstituted or substituted benzothiophenyl.

For example, $R_2$ is cyclopropyl, cyclobutyl, cyclopentyl, cyclohexyl, or cycloheptyl, and is optionally substituted.

For example, $R_2$ is cyclopentyl or cyclohexyl.

For example, $R_2$ is cyclopentyl or cyclohexyl substituted with unsubstituted or substituted di-$C_1$-$C_6$ alkylamino.

For example, $R_2$ is pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_2$ is piperidinyl and is optionally substituted.

For example, $R_2$ is pyrrolidinyl and is optionally substituted.

For example, $R_2$ is -$T_r$-$R_r$.

For example, $R_3$, $R_4$, $R_5$, $R_6$, $R_7$, $R_8$, $R_9$ and $R_{10}$ are each independently H.

For example, one or more of $R_3$, $R_4$, $R_5$, $R_6$, $R_7$, $R_8$, $R_9$ and $R_{10}$ are each independently unsubstituted or substituted $C_1$-$C_6$ straight chain or $C_3$-$C_6$ branched alkyl selected from unsubstituted or substituted methyl, ethyl, n-propyl, i-propyl, n-butyl, s-butyl, and t-butyl.

For example, $T_r$ is unsubstituted or substituted $C_1$-$C_9$ straight chain or $C_3$-$C_9$ branched alkyl linker.

For example, $T_r$ is unsubstituted or straight chain methyl, ethyl, propyl, butyl, pentyl, hexyl, heptyl, octyl, or nonyl or branched propyl, butyl, pentyl, hexyl, heptyl, octyl, or nonyl.

For example, $R_r$ is unsubstituted or substituted phenyl or naphthyl.

For example, $R_r$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_r$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted.

For example, $R_r$ is cyclopropyl, cyclobutyl, cyclopentyl, cyclohexyl, or cycloheptyl, and is optionally substituted.

For example, $R_r$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_r$ is a fused polycyclic aromatic moiety.

For example, one of $R_9$ and $R_{10}$ is H and the other is -$T_q$-$R_q$.

For example, $T_q$ is a bond and $R_q$ is unsubstituted or substituted heterocycle comprising 1 or 2, 5- or 6-member rings and 1-4 heteroatoms selected from N, O and S.

For example, $T_q$ is a bond and $R_q$ is unsubstituted or substituted piperidinyl.

For example, $T_q$ is $C_1$-$C_6$ alkyl linker and $R_q$ is unsubstituted or substituted heterocycle comprising 1 or 2, 5- or 6-member rings and 1-4 heteroatoms selected from N, O and S.

For example, $T_q$ is $C_1$-$C_6$ alkyl linker and $R_q$ is unsubstituted or substituted piperidinyl.

For example m is 0.

For example, m is 1.

For example, m is 1 and $R_8$ is —C(O)$NR_{11}R_{12}$.

For example, m is 1 and $R_8$ is —S(O)$_2R_{11}$.

For example, m is 1 and $R_8$ is —C(O)$R_{11}$.

For example, $R_{11}$ is unsubstituted or substituted $C_1$-$C_6$ alkyl.

For example, $R_{11}$ is phenyl substituted $C_1$-$C_6$ alkyl.

For example, $R_{11}$ is unsubstituted or substituted $C_6$-$C_{10}$ aryl.

For example, $R_{11}$ is unsubstituted or substituted phenyl.

For example, $R_{11}$ is phenyl substituted with one or more groups, each of which can be the same or different, selected from fluorine, chlorine, bromine, and iodine.

For example, $R_{11}$ is phenyl substituted with one or more groups, each of which can be the same or different, selected from unsubstituted or substituted $C_1$-$C_6$ straight chain or $C_3$-$C_6$ branched alkyl.

For example, $R_{11}$ is phenyl substituted with one or more groups, each of which can be the same or different, selected from unsubstituted or substituted methyl, ethyl, n-propyl, i-propyl, n-butyl, s-butyl, and t-butyl.

For example, $R_{11}$ is phenyl substituted with one or more groups, each of which can be the same or different, selected from unsubstituted or substituted methoxyl, ethoxyl, propyloxyl and iso-propyloxyl.

For example, $R_{11}$ is phenyl substituted with unsubstituted or substituted $C_1$-$C_6$ alkylcarbonyl.

For example, $R_{11}$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_{12}$ is H.

For example, $R_{11}$ is -$T_tR_t$.

For example, $T_t$ is a bond.

For example, $T_t$ is unsubstituted or substituted $C_1$-$C_6$ alkyl linker.

For example, $R_t$ is unsubstituted or substituted $C_1$-$C_6$ alkyl.

For example, $R_t$ is unsubstituted or substituted $C_6$-$C_{10}$ aryl.

For example, $R_r$ is —C(O)OR$_{13}$.
For example, $R_r$ is —C(O)R$_{13}$.
For example, $R_{13}$ is H.
For example, $R_{13}$ is unsubstituted or substituted $C_1$-$C_6$ straight chain or $C_3$-$C_6$ branched alkyl.
For example, $R_{13}$ is unsubstituted or substituted methyl, ethyl, n-propyl, i-propyl, n-butyl, s-butyl, and t-butyl.

The present invention also provides a compound of Formula II or IIa or a pharmaceutically acceptable salt, prodrug, metabolite, analog or derivative thereof:

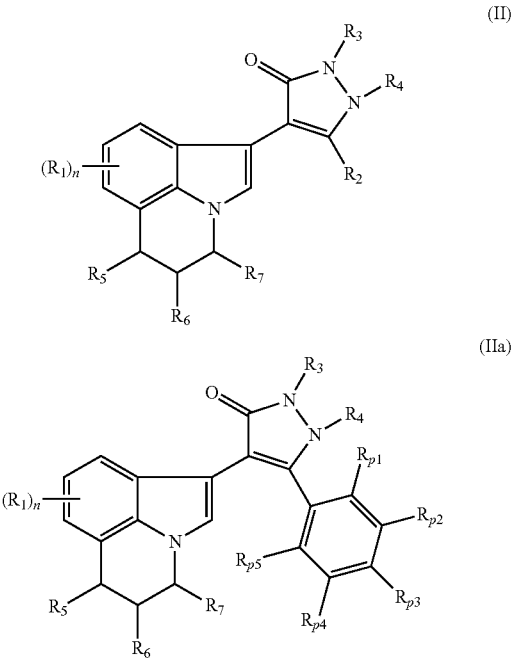

wherein:
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

$R_2$ is H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_r$-$R_r$;

$R_3$, $R_4$, $R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2, 5- or 6-member rings and 1-4 heteroatoms selected from N, O and S, and optionally containing unsaturation; and $R_{P1}$, $R_{P2}$, $R_{P3}$, $R_{P4}$ and $R_{P5}$ are each independently H, hydroxyl, halogen, unsubstituted or substituted $C_1$-$C_6$ alkyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, nitro, cyano, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or any two adjacent of $R_{P1}$, $R_{P2}$, $R_{P3}$, $R_{P4}$ and $R_{P5}$, together with the carbon atoms to which they are attached, form a 5- or 6-member ring which optionally comprises 1-4 heteroatoms selected from N, O and S, optionally is partially unsaturated or fully unsaturated, and optionally is substituted.

For example, n is 0.
For example, n is 1.
For example, n is 1 and $R_1$ is unsubstituted or substituted $C_1$-$C_6$ alkyl.
For example, $R_1$ is unsubstituted or substituted methyl, ethyl, n-propyl, i-propyl, n-butyl, s-butyl, t-butyl, n-pentyl, s-pentyl or n-hexyl.
For example, $R_1$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_5$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.
For example, $R_1$ is unsubstituted or substituted methoxyl, ethoxyl, propyloxyl or iso-propyloxyl.
For example, $R_1$ is $C_1$-$C_6$ alkoxyl substituted with one or more groups, each of which can be the same or different, selected from fluorine, chlorine, bromine, and iodine.
For example, $R_1$ is fluorine, chlorine, bromine, or iodine.
For example, $R_2$ is H.
For example, $R_2$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.
For example, $R_2$ is unsubstituted or substituted methyl, ethyl, n-propyl, i-propyl, or 2,2-dimethylpropyl.
For example, $R_2$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is unsubstituted or substituted phenyl or naphthyl.

For example, $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is phenyl or naphthyl substituted with one or more groups, each of which can be the same or different, selected from unsubstituted or substituted $C_1$-$C_6$ straight chain or $C_3$-$C_6$ branched alkyl.

For example, $R_2$ is phenyl or naphthyl substituted with one or more groups, each of which can be the same or different, selected from unsubstituted or substituted methyl, ethyl, n-propyl, i-propyl, n-butyl, s-butyl, and t-butyl.

For example, $R_2$ is phenyl or naphthyl substituted with one or more groups, each of which can be the same or different, selected from unsubstituted or substituted methoxyl, ethoxyl, propyloxyl and iso-propyloxyl.

For example, $R_2$ is phenyl or naphthyl substituted with one or more groups, each of which can be the same or different, selected from fluorine, chlorine, bromine, and iodine.

For example, $R_2$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzothiadiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted with one or more groups, each of which can be the same or different, selected from hydroxyl, halogen, nitro, cyano, and unsubstituted or substituted $C_1$-$C_6$ alkyl, unsubstituted or substituted $C_1$-$C_6$ alkoxyl.

For example, $R_2$ is heteroaryl substituted with one or more groups, each of which can be the same or different, selected from unsubstituted or substituted $C_1$-$C_6$ straight chain or $C_3$-$C_6$ branched alkyl.

For example, $R_2$ is heteroaryl substituted with one or more groups, each of which can be the same or different, selected from unsubstituted or substituted methyl, ethyl, n-propyl, i-propyl, n-butyl, s-butyl, and t-butyl.

For example, $R_2$ is heteroaryl substituted with one or more groups, each of which can be the same or different, selected from fluorine, chlorine, bromine, and iodine.

For example, $R_2$ is pyridinyl, thiophenyl, isoxazolyl, benzofuranyl, benzothiophenyl, benzoimidazolyl, or benzothiadiazolyl.

For example, $R_2$ is unsubstituted or substituted benzothiophenyl.

For example, $R_2$ is cyclopropyl, cyclobutyl, cyclopentyl, cyclohexyl, or cycloheptyl, and is optionally substituted.

For example, $R_2$ is cyclopentyl or cyclohexyl.

For example, $R_2$ is pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_2$ is -$T_r$-$R_r$.

For example, $R_3$, $R_4$, $R_5$, $R_6$ and $R_7$ are each independently H.

For example, one or more of $R_3$, $R_4$, $R_5$, $R_6$ and $R_7$ are each independently unsubstituted or substituted $C_1$-$C_6$ straight chain or $C_3$-$C_6$ branched alkyl selected from unsubstituted or substituted methyl, ethyl, n-propyl, i-propyl, n-butyl, s-butyl, and t-butyl.

For example, $R_3$ is H.

For example, $R_4$ is H.

For example, $T_r$ is unsubstituted or substituted $C_1$-$C_9$ straight chain or $C_3$-$C_9$ branched alkyl linker.

For example, $T_r$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.

For example, $R_r$ is unsubstituted or substituted phenyl or naphthyl.

For example, $R_r$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_r$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted.

For example, $R_r$ is cyclopropyl, cyclobutyl, cyclopentyl, cyclohexyl, or cycloheptyl, and is optionally substituted.

For example, $R_r$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_r$ is a fused polycyclic aromatic moiety.

For example, each of $R_{P1}$, $R_{P2}$, $R_{P3}$, $R_{P4}$ and $R_{P5}$ is H.

For example, four of $R_{P1}$, $R_{P2}$, $R_{P3}$, $R_{P4}$ and $R_{P5}$ are H.

For example, three of $R_{P1}$, $R_{P2}$, $R_{P3}$, $R_{P4}$ and $R_{P5}$ are H.

For example, two of $R_{P1}$, $R_{P2}$, $R_{P3}$, $R_{P4}$ and $R_{P5}$ are H.

For example, one of $R_{P1}$, $R_{P2}$, $R_{P3}$, $R_{P4}$ and $R_{P5}$ is H.

For example, at least one of $R_{P1}$, $R_{P2}$, $R_{P3}$, $R_{P4}$ and $R_{P5}$ is not H.

For example, at least two of $R_{P1}$, $R_{P2}$, $R_{P3}$, $R_{P4}$ and $R_{P5}$ are not H.

For example, at least three of $R_{P1}$, $R_{P2}$, $R_{P3}$, $R_{P4}$ and $R_{P5}$ are not H.

For example, at least one of $R_{P1}$, $R_{P2}$, $R_{P3}$, $R_{P4}$ and $R_{P5}$ is unsubstituted or substituted methyl, ethyl, n-propyl, i-propyl, n-butyl, s-butyl, t-butyl, n-pentyl, s-pentyl or n-hexyl.

For example, at least one of $R_{P1}$, $R_{P2}$, $R_{P3}$, $R_{P4}$ and $R_{P5}$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, at least one of $R_{P1}$, $R_{P2}$, $R_{P3}$, $R_{P4}$ and $R_{P5}$ is fluorine, chlorine, bromine, or iodine.

For example, at least two of $R_{P1}$, $R_{P2}$, $R_{P3}$, $R_{P4}$ and $R_{P5}$ are fluorine, chlorine, bromine, or iodine.

For example, at least one of $R_{P1}$, $R_{P2}$, $R_{P3}$, $R_{P4}$ and $R_{P5}$ is unsubstituted or substituted methoxyl, ethoxyl, propyloxyl or iso-propyloxyl.

For example, at least one of $R_{P1}$, $R_{P2}$, $R_{P3}$, $R_{P4}$ and $R_{P5}$ is unsubstituted or substituted phenyl or naphthyl.

For example, at least one of $R_{P1}$, $R_{P2}$, $R_{P3}$, $R_{P4}$ and $R_{P5}$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_5$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, at least one of $R_{P1}$, $R_{P2}$, $R_{P3}$, $R_{P4}$ and $R_{P5}$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted.

For example, at least one of $R_{P1}$, $R_{P2}$, $R_{P3}$, $R_{P4}$ and $R_{P5}$ is cyclopropyl, cyclobutyl, cyclopentyl, cyclohexyl, or cycloheptyl, and is optionally substituted.

For example, at least one of $R_{P1}$, $R_{P2}$, $R_{P3}$, $R_{P4}$ and $R_{P5}$ is heterocycle selected from pyrrolidinyl, imidazolidinyl, pyrazolidinyl, oxazolidinyl, isoxazolidinyl, triazolidinyl, tetrahydrofuranyl, piperidinyl, piperazinyl and morpholinyl, and the like, and is optionally substituted.

For example, any two adjacent of $R_{P1}$, $R_{P2}$, $R_{P3}$, $R_{P4}$ and $R_{P5}$, together with the carbon atoms they are attached, form a phenyl which is optionally substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, and unsubstituted or substituted $C_6$-$C_{10}$ arylaminocarbonyl.

For example, any two adjacent of $R_{P1}$, $R_{P2}$, $R_{P3}$, $R_{P4}$ and $R_{P5}$, together with the carbon atoms they are attached, form an unsubstituted or substituted heteroaryl comprising 1 or 2, 5- or 6-member rings and 1-4 heteroatoms selected from N, O and S, which is optionally partially unsaturated or fully unsaturated.

For example, any two adjacent of $R_{P1}$, $R_{P2}$, $R_{P3}$, $R_{P4}$ and $R_{P5}$, together with the carbon atoms they are attached, form an unsubstituted or substituted fused polycyclic aromatic moiety.

For example, any two adjacent of $R_{P1}$, $R_{P2}$, $R_{P3}$, $R_{P4}$ and $R_{P5}$, together with the carbon atoms they are attached, form pyrrolyl, furanyl, thiophenyl, thiazolyl, isothiazolyl, thiadiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted with one or more groups, each of which can be the same or different, selected from hydroxyl, halogen, nitro, cyano, and unsubstituted or substituted $C_1$-$C_6$ alkyl, unsubstituted or substituted $C_1$-$C_6$ alkoxyl.

For example, any two adjacent of $R_{P1}$, $R_{P2}$, $R_{P3}$, $R_{P4}$ and $R_{P5}$, together with the carbon atoms they are attached, form heteroaryl substituted with one or more groups, each of which can be the same or different, selected from unsubstituted or substituted $C_1$-$C_6$ straight chain or $C_3$-$C_6$ branched alkyl.

For example, any two adjacent of $R_{P1}$, $R_{P2}$, $R_{P3}$, $R_{P4}$ and $R_{P5}$, together with the carbon atoms they are attached, form heteroaryl substituted with one or more groups, each of which can be the same or different, selected from unsubstituted or substituted methyl, ethyl, n-propyl, i-propyl, n-butyl, s-butyl, and t-butyl.

For example, any two adjacent of $R_{P1}$, $R_{P2}$, $R_{P3}$, $R_{P4}$ and $R_{P5}$, together with the carbon atoms they are attached, form heteroaryl substituted with one or more groups, each of which can be the same or different, selected from fluorine, chlorine, bromine, and iodine.

The present invention also provides a compound of Formula III, IIIa, or IIIb or a pharmaceutically acceptable salt, prodrug, metabolite, analog or derivative thereof:

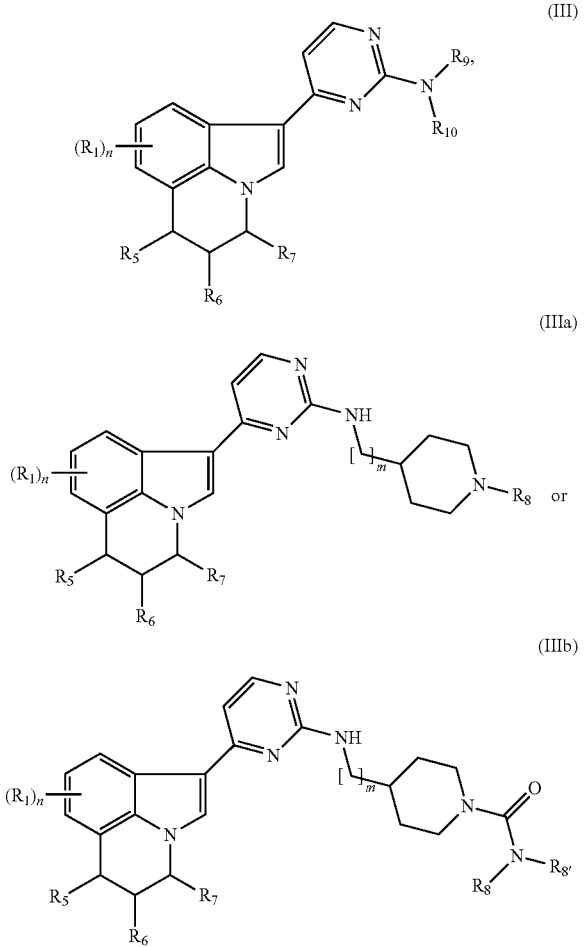

wherein:

n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_5$, $R_6$, $R_7$ and $R_{8'}$ are each independently H, unsubstituted or substituted $C_1$-$C_6$ alkyl, or unsubstituted or substituted $C_3$-$C_{10}$ carbocycle optionally containing unsaturation;

$R_8$ is H, unsubstituted or substituted $C_1$-$C_6$ alkyl, —C(O)$R_{11}$, —C(O)O$R_{11}$, —C(O)N$R_{11}R_{12}$, or —S(O)$_2R_{11}$;

$R_9$ and $R_{10}$ are each independently H, unsubstituted or substituted $C_1$-$C_6$ alkyl, or -$T_q$-$R_q$;

$T_q$ is unsubstituted or substituted $C_1$-$C_6$ alkyl linker, or a bond;

$R_q$ is H, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S;

$R_{11}$ and $R_{12}$ are each independently H, unsubstituted or substituted $C_1$-$C_6$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, or unsubstituted or substituted heterocycle comprising 1 or 2, 5- or 6-member rings and 1-4 heteroatoms selected from N, O and S, or -$T_t$-$R_t$;

$T_t$ is unsubstituted or substituted $C_1$-$C_6$ alkyl linker, or a bond;

$R_t$ is H, unsubstituted or substituted $C_1$-$C_6$ alkyl, unsubstituted or substituted $C_6$-$C_{10}$ aryl, unsubstituted or substituted $C_1$-$C_6$ alkoxy, unsubstituted or substituted $C_6$-$C_{10}$ aryloxy, unsubstituted or substituted heteroaryl comprising 1 or 2, 5- or 6-member rings and 1-4 heteroatoms selected from N, O and S, unsubstituted or substituted $C_3$-$C_{10}$ carbocycle, unsubstituted or substituted heterocycle comprising 1 or 2, 5- or 6-member rings and 1-4 heteroatoms selected from N, O and S, —C(O)O$R_{13}$, or —C(O)$R_{13}$; and $R_{13}$ is H or unsubstituted or substituted $C_1$-$C_6$ alkyl.

For example, n is 0.

For example, $R_1$ is H or unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl and n-hexyl.

For example, $R_5$, $R_6$ and $R_7$ are each H.

For example, $R_5$, $R_6$ and $R_7$ are each independently unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl and n-hexyl.

For example, each of $R_9$ and $R_{10}$ is H.

For example, one of $R_9$ and $R_{10}$ is H.

For example, at least one of $R_9$ and $R_{10}$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl and n-hexyl.

For example, $T_q$ is a bond.

For example, $T_q$ is $C_1$-$C_6$ straight chain or $C_3$-$C_6$ branched alkyl linker, including but not limited to, methyl, ethyl, n-propyl, i-propyl, n-butyl, s-butyl, t-butyl, n-pentyl, s-pentyl, and n-hexyl.

For example, $R_q$ is H.

For example, $R_q$ is phenyl or naphthyl optionally substituted with hydroxyl, halogen (e.g., fluorine, chlorine, bromine, and iodine), nitro, cyano, unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl), or unsubstituted or substituted $C_1$-$C_6$ alkoxy (e.g., methoxy, ethoxy, propyloxy, i-propyloxy, methylenedioxy, and ethylenedioxy).

For example, $R_q$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, imidazolthiazolyl, quinoxalinyl, and the like, and is optionally substituted.

For example, $R_q$ is cyclopropyl, cyclobutyl, cyclopentyl, cyclohexyl, or cycloheptyl, and is optionally substituted.

For example, $R_q$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

For example, $R_q$ is piperidinyl.

For example, $R_q$ is 4-piperidinyl.

For example, $R_q$ is heterocycle substituted with unsubstituted or substituted $C_1$-$C_6$ alkyl, —C(O)$R_{14}$, —C(O)O$R_{14}$, —C(O)N$R_{14}R_{15}$, or —S(O)$_2R_{14}$, wherein:

$R_{14}$ and $R_{15}$ are each independently H, unsubstituted or substituted $C_1$-$C_6$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, unsubstituted or substituted heterocycle comprising 1 or 2, 5- or 6-member rings and 1-4 heteroatoms selected from N, O and S, or -$T_z$-$R_z$;

$T_z$ is unsubstituted or substituted $C_1$-$C_6$ alkyl linker, or a bond;

$R_z$ is H, unsubstituted or substituted $C_1$-$C_6$ alkyl, unsubstituted or substituted $C_6$-$C_{10}$ aryl, unsubstituted or substituted $C_1$-$C_6$ alkoxy, unsubstituted or substituted $C_6$-$C_{10}$ aryloxy, unsubstituted or substituted heteroaryl comprising 1 or 2, 5- or 6-member rings and 1-4 heteroatoms selected from N, O and S, —C(O)$R_{16}$, —C(O)O$R_{16}$— (CH$_2$)$_u$C(O)O$R_{16}$, —(CH$_2$)$_u$C(O)N$R_{17}R_{18}$ or unsubstituted or substituted aralkyl;

$R_{16}$ is H, or unsubstituted or substituted $C_1$-$C_6$ alkyl;

u is 0, 1, 2, 3, 4, 5 or 6; and $R_{17}$ and $R_{18}$ are each independently H, unsubstituted or substituted $C_1$-$C_6$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle, unsubstituted or substituted heterocycle comprising 1 or 2, 5- or 6-member rings and 1-4 heteroatoms selected from N, O and S.

For example, each of $R_{14}$ and $R_{15}$ is H.

For example, one of $R_{14}$ and $R_{15}$ is H.

For example, at least one of $R_{14}$ and $R_{15}$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl and n-hexyl.

For example, at least one of $R_{14}$ and $R_{15}$ is $C_1$-$C_6$ straight chain or $C_3$-$C_6$ branched alkyl substituted with hydroxyl, halogen (e.g., fluorine, chlorine, bromine, and iodine), unsubstituted or substituted amino, alkylamino (e.g., methylamino, ethylamino, propylamino and i-propylamino), unsubstituted or substituted di-$C_1$-$C_6$ alkylamino (e.g., dimethylamino, diethylamino, dipropylamino and di-i-propylamino), or unsubstituted or substituted $C_1$-$C_6$ alkoxy (e.g., methoxy, ethoxy, propyloxy, and i-propyloxy).

For example, at least one of $R_{14}$ and $R_{15}$ is unsubstituted or substituted phenyl or naphthyl.

For example, at least one of $R_{14}$ and $R_{15}$ is phenyl substituted with one or more groups, each of which can be the same or different, selected from hydroxyl, halogen (e.g., fluorine, chlorine, bromine, and iodine), nitro, cyano, unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl, each of which is optionally substituted with halogen), unsubstituted or substituted $C_1$-$C_6$ alkoxy (e.g., methoxy, ethoxy, propyloxy, i-propyloxy, methylenedioxy, and ethylenedioxy, each of which is optionally substituted with halogen), unsubstituted or substituted $C_6$-$C_{10}$ aryl-$C_1$-$C_6$ alkyl (e.g., benzyl), unsubstituted or substituted heteroaryl-$C_1$-$C_6$ alkyl, unsubstituted or substituted $C_6$-$C_{10}$ aryloxy (e.g., phenoxy), unsubstituted or substituted heteroaryloxy, unsubstituted or substituted $C_1$-$C_6$ alkylcarbonyl (e.g., methylcarbonyl, ethylcarbonyl, propylcarbonyl, i-propylcarbonyl, butylcarbonyl, and t-butylcarbonyl), unsubstituted or substituted $C_1$-$C_6$ alkoxycarbonyl (e.g., methoxycarbonyl, ethoxycarbonyl, propyloxycarbonyl, i-propyloxycarbonyl, butoxycarbonyl, and t-butoxycarbonyl), carboxyl, amino, unsubstituted or substituted $C_1$-$C_6$ alkylamino (e.g., methylamino, ethylamino, propylamino and i-propylamino), unsubstituted or substituted di-$C_1$-$C_6$ alkylamino (e.g., dimethylamino, diethylamino, dipropylamino and di-i-propylamino), unsubstituted or substituted $C_1$-$C_6$ alkylcarbonylamino (e.g., methylcarbonylamino, ethylcarbonylamino, propylcarbonylamino, i-propylcarbonylamino, butylcarbonylamino, and t-butylcarbonylamino), unsubstituted or substituted $C_1$-$C_6$ alkylsulfonyl (e.g., methylsulfonyl and ethylsulfonyl), and unsubstituted or substituted $C_1$-$C_6$ alkylsulfinyl (e.g., methylsulfinyl and ethylsulfinyl).

For example, at least one of $R_{14}$ and $R_{15}$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, imidazolthiazolyl, quinoxalinyl, and the like, and is optionally substituted with halogen (e.g., fluorine, chlorine, bromine, and iodine), unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl, each of which is optionally substituted with halogen), unsubstituted or substituted $C_1$-$C_6$ alkylcarbonyl (e.g., methylcarbonyl, ethylcarbonyl, propylcarbonyl, i-propylcarbonyl, butylcarbonyl, and t-butylcarbonyl), unsubstituted or substituted $C_1$-$C_6$ alkoxycarbonyl (e.g., methoxycarbonyl, ethoxycarbonyl, propyloxycarbonyl, i-propyloxycarbonyl, butoxycarbonyl, and t-butoxycarbonyl), carboxyl, amino, unsubstituted or substituted $C_1$-$C_6$ alkylamino (e.g., methylamino, ethylamino, propylamino and i-propylamino), unsubstituted or substituted di-$C_1$-$C_6$ alkylamino (e.g., dimethylamino, diethylamino, dipropylamino and di-i-propylamino), or unsubstituted or substituted $C_1$-$C_6$ alkylcarbonylamino (e.g., methylcarbonylamino, ethylcarbonylamino, propylcarbonylamino, i-propylcarbonylamino, butylcarbonylamino, and t-butylcarbonylamino).

For example, at least one of $R_{14}$ and $R_{15}$ is heteroaryl selected from furanyl, thiophenyl, thiazolyl, imidazolyl, pyridinyl, and quinolinyl.

For example, at least one of $R_{14}$ and $R_{15}$ is cyclopropyl, cyclobutyl, cyclopentyl, cyclohexyl, or cycloheptyl, and is optionally substituted.

For example, at least one of $R_{14}$ and $R_{15}$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

For example, at least one of $R_{14}$ and $R_{15}$ is -$T_z$-$R_z$.

For example, $T_z$ is a bond.

For example, $T_z$ is $C_1$-$C_6$ straight chain or $C_3$-$C_6$ branched alkyl linker, including but not limited to, methyl, ethyl, n-propyl, i-propyl, n-butyl, s-butyl, t-butyl, n-pentyl, s-pentyl, and n-hexyl.

For example, $R_z$ is H.

For example, $R_z$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl and n-hexyl.

For example, $R_z$ is unsubstituted or substituted phenyl or naphthyl.

For example, $R_z$ is phenyl substituted with one or more groups, each of which can be the same or different, selected from hydroxyl, halogen (e.g., fluorine, chlorine, bromine, and iodine), nitro, cyano, unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl, each of which is optionally substituted with halogen), unsubstituted or substituted $C_1$-$C_6$ alkoxy (e.g., methoxy, ethoxy, propyloxy, i-propyloxy, methylenedioxy, and ethylenedioxy, each of which is optionally substituted with halogen), and unsubstituted or substituted amino For example, $R_z$ is unsubstituted or substituted $C_1$-$C_6$ alkoxy, including but not limited to, methoxy, ethoxy, propyloxy, and i-propyloxy.

For example, $R_z$ is phenoxy.

For example, $R_z$ is unsubstituted or substituted heteroaryl comprising 1 or 2, 5- or 6-member rings and 1-4 heteroatoms selected from N, O and S.

For example, $R_z$ is —$(CH_2)_uC(O)OR_{16}$ where u is 1 and $R_{16}$ is methyl, ethyl, n-propyl, i-propyl, n-butyl, s-butyl, t-butyl, n-pentyl, s-pentyl or n-hexyl.

For example, $R_z$ is —$(CH_2)_uC(O)NR_{17}R_{18}$.

For example, $R_z$ is unsubstituted or substituted aralkyl, including but not limited to benzyl.

For example, $R_z$ is phenyl substituted with one or more groups, each of which can be the same or different, selected from unsubstituted or substituted $C_6$-$C_{10}$ aryl, —$C(O)OR_{16}$, —$C(O)R_{16}$ or —$(CH_2)_uC(O)NR_{17}R_{18}$.

For example, $R_z$ is —$C(O)OR_{16}$ where $R_{16}$ is methyl, ethyl, n-propyl, i-propyl, n-butyl, s-butyl, t-butyl, n-pentyl, s-pentyl or n-hexyl.

For example, $R_{16}$ is H.

For example, $R_{16}$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl, and n-hexyl.

For example, m is 0.

For example, m is 1.

For example, $R_8$ is H.

For example, $R_8$ is unsubstituted or substituted $C_1$-$C_6$ alkyl.

For example, $R_8$ is —$C(O)R_{11}$.

For example, $R_8$ is —$C(O)OR_{11}$.

For example, $R_8$ is —$C(O)NR_{11}R_{12}$.

For example, $R_8$ is —$S(O)_2R_{11}$.

For example, $R_{12}$ is H.

For example, $R_{11}$ is H.

For example, $R_{11}$ is unsubstituted or substituted $C_1$-$C_6$ alkyl.

For example, $R_{11}$ is phenyl substituted $C_1$-$C_6$ alkyl.

For example, $R_{11}$ is unsubstituted or substituted $C_1$-$C_6$ aryl.

For example, $R_{11}$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, imidazolthiazolyl, quinoxalinyl, and the like, and is optionally substituted with halogen (e.g., fluorine, chlorine, bromine, and iodine), unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl, each of which is optionally substituted with halogen), unsubstituted or substituted $C_1$-$C_6$ alkylcarbonyl (e.g., methylcarbonyl, ethylcarbonyl, propylcarbonyl, i-propylcarbonyl, butylcarbonyl, and t-butylcarbonyl), unsubstituted or substituted $C_1$-$C_6$ alkoxycarbonyl (e.g., methoxycarbonyl, ethoxycarbonyl, propyloxycarbonyl, i-propyloxycarbonyl, butoxycarbonyl, and t-butoxycarbonyl), carboxyl, amino, unsubstituted or substituted $C_1$-$C_6$ alkylamino (e.g., methylamino, ethylamino, propylamino and i-propylamino), unsubstituted or substituted di-$C_1$-$C_6$ alkylamino (e.g., dimethylamino, diethylamino, dipropylamino and di-i-propylamino), or unsubstituted or substituted $C_1$-$C_6$ alkylcarbonylamino (e.g., methylcarbonylamino, ethylcarbonylamino, propylcarbonylamino, i-propylcarbonylamino, butylcarbonylamino, and t-butylcarbonylamino).

For example, $R_{11}$ is cyclopropyl, cyclobutyl, cyclopentyl, cyclohexyl, or cycloheptyl, and is optionally substituted.

For example, $R_{11}$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

For example, $R_{11}$ is -$T_t$-$R_t$.

For example, $T_t$ is a bond.

For example, $T_t$ is unsubstituted or substituted $C_1$-$C_6$ alkyl linker.

For example, $R_t$ is H.

For example, $R_t$ is unsubstituted or substituted $C_1$-$C_6$ alkyl.

For example, $R_t$ is unsubstituted or substituted $C_1$-$C_6$ aryl.

For example, $R_t$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, imidazolthiazolyl, quinoxalinyl, and the like, and is optionally substituted with halogen (e.g., fluorine, chlorine, bromine, and iodine), unsubstituted or substituted $C_1$-$C_6$ alkyl (e.g., methyl, ethyl, n-propyl, i-propyl, n-butyl, s-butyl, t-butyl, n-pentyl, s-pentyl and n-hexyl, each of which is optionally substituted with halogen), unsubstituted or substituted $C_1$-$C_6$ alkylcarbonyl (e.g., methylcarbonyl, ethylcarbonyl, propylcarbonyl, i-propylcarbonyl, butylcarbonyl, and t-butylcarbonyl), unsubstituted or substituted $C_1$-$C_6$ alkoxycarbonyl (e.g., methoxycarbonyl, ethoxycarbonyl, propyloxycarbonyl, i-propyloxycarbonyl, butoxycarbonyl, and t-butoxycarbonyl), carboxyl, amino, unsubstituted or substituted $C_1$-$C_6$ alkylamino (e.g., methylamino, ethylamino, propylamino and i-propylamino), unsubstituted or substituted di-$C_1$-$C_6$ alkylamino (e.g., dimethylamino, diethylamino, dipropylamino and di-i-propylamino), or unsubstituted or substituted $C_1$-$C_6$ alkylcarbonylamino (e.g., methylcarbonylamino, ethylcarbonylamino, propylcarbonylamino, i-propylcarbonylamino, butylcarbonylamino, and t-butylcarbonylamino).

For example, $R_t$ is cyclopropyl, cyclobutyl, cyclopentyl, cyclohexyl, or cycloheptyl, and is optionally substituted.

For example, $R_t$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

For example, $R_t$ is —$C(O)OR_{13}$.

For example, $R_t$ is —$C(O)R_{13}$.

For example, $R_{13}$ is H.

For example, $R_{13}$ is unsubstituted or substituted $C_1$-$C_6$ alkyl.

For example, $R_{13}$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl, and n-hexyl.

For example, $R_{8'}$ is H.

For example, $R_{8'}$ is unsubstituted or substituted $C_1$-$C_6$ alkyl.

For example, $R_{8'}$ is unsubstituted or substituted, $C_1$-$C_6$ straight chain or $C_3$-$C_6$ branched alkyl, including but not limited to, methyl, ethyl, n-propyl, i-propyl, n-butyl, s-butyl, t-butyl, n-pentyl, s-pentyl, and n-hexyl.

The present invention also provides a compound of Formula IV or a pharmaceutically acceptable salt, prodrug, metabolite, analog or derivative thereof:

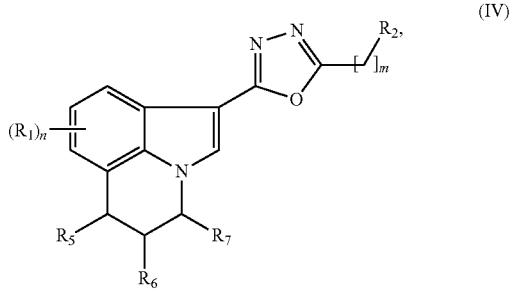

wherein
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;
m is 0, 1, 2, 3, 4, 5 or 6;
$R_2$ is H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_r$-$R_r$;
$T_r$ is unsubstituted or substituted $C_1$-$C_6$ alkyl linker, or a bond;
$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2, 5- or 6-member rings and 1-4 heteroatoms selected from N, O and S, and optionally containing unsaturation; and
$R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation.

For example, n is 0.
For example, n is 1.
For example, n is 1 and $R_1$ is unsubstituted or substituted $C_1$-$C_6$ alkyl.
For example, $R_1$ is unsubstituted or substituted methyl, ethyl, n-propyl, i-propyl, n-butyl, s-butyl, t-butyl, n-pentyl, s-pentyl or n-hexyl.
For example, $R_1$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_5$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_1$ is unsubstituted or substituted methoxyl, ethoxyl, propyloxyl or iso-propyloxyl.
For example, $R_1$ is $C_1$-$C_6$ alkoxyl substituted with one or more groups, each of which can be the same or different, selected from fluorine, chlorine, bromine, and iodine.
For example, $R_1$ is fluorine, chlorine, bromine, or iodine.
For example, m is 0.
For example, m is 1.
For example, $R_2$ is H.
For example, $R_2$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.
For example, $R_2$ is unsubstituted or substituted methyl, ethyl, n-propyl, i-propyl, or 2,2-dimethylpropyl.
For example, $R_2$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.
For example, $R_2$ is unsubstituted or substituted phenyl or naphthyl.
For example, $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.
For example, $R_2$ is phenyl or naphthyl substituted with one or more groups, each of which can be the same or different, selected from unsubstituted or substituted $C_1$-$C_6$ straight chain or $C_3$-$C_6$ branched alkyl.
For example, $R_2$ is phenyl or naphthyl substituted with one or more groups, each of which can be the same or different, selected from unsubstituted or substituted methyl, ethyl, n-propyl, i-propyl, n-butyl, s-butyl, and t-butyl.
For example, $R_2$ is phenyl or naphthyl substituted with one or more groups, each of which can be the same or different, selected from unsubstituted or substituted methoxyl, ethoxyl, propyloxyl and iso-propyloxyl.

For example, $R_2$ is phenyl or naphthyl substituted with one or more groups, each of which can be the same or different, selected from fluorine, chlorine, bromine, and iodine.

For example, $R_2$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzothiadiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted with one or more groups, each of which can be the same or different, selected from hydroxyl, halogen, nitro, cyano, and unsubstituted or substituted $C_1$-$C_6$ alkyl, unsubstituted or substituted $C_1$-$C_6$ alkoxyl.

For example, $R_2$ is heteroaryl substituted with one or more groups, each of which can be the same or different, selected from unsubstituted or substituted $C_1$-$C_6$ straight chain or $C_3$-$C_6$ branched alkyl.

For example, $R_2$ is heteroaryl substituted with one or more groups, each of which can be the same or different, selected from unsubstituted or substituted methyl, ethyl, n-propyl, i-propyl, n-butyl, s-butyl, and t-butyl.

For example, $R_2$ is heteroaryl substituted with one or more groups, each of which can be the same or different, selected from fluorine, chlorine, bromine, and iodine.

For example, $R_2$ is pyridinyl, thiophenyl, isoxazolyl, benzofuranyl, benzothiophenyl, benzoimidazolyl, or benzothiadiazolyl.

For example, $R_2$ is unsubstituted or substituted benzothiophenyl.

For example, $R_2$ is cyclopropyl, cyclobutyl, cyclopentyl, cyclohexyl, or cycloheptyl, and is optionally substituted.

For example, $R_2$ is cyclopentyl or cyclohexyl.

For example, $R_2$ is pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_2$ is -$T_r$-$R_r$.

For example, $R_5$, $R_6$ and $R_7$ are each independently H.

For example, one or more of $R_5$, $R_6$ and $R_7$ are each independently unsubstituted or substituted $C_1$-$C_6$ straight chain or $C_3$-$C_6$ branched alkyl selected from unsubstituted or substituted methyl, ethyl, n-propyl, i-propyl, n-butyl, s-butyl, and t-butyl.

For example, $T_r$ is unsubstituted or substituted $C_1$-$C_9$ straight chain or $C_3$-$C_9$ branched alkyl linker.

For example, $T_r$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.

For example, $R_r$ is unsubstituted or substituted phenyl or naphthyl.

For example, $R_r$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_r$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted.

For example, $R_r$ is cyclopropyl, cyclobutyl, cyclopentyl, cyclohexyl, or cycloheptyl, and is optionally substituted.

For example, $R_r$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_r$ is a fused polycyclic aromatic moiety.

The present invention also provides a compound of Formula V or a pharmaceutically acceptable salt, prodrug, metabolite, analog or derivative thereof:

(V)

wherein n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ is H, unsubstituted or substituted $C_1$-$C_9$ alkyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2, 5- or 6-member rings and 1-4 heteroatoms selected from N, O and S, and optionally containing unsaturation, or -$T_r$-$R_r$;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2, 5- or 6-member rings and 1-4 heteroatoms selected from N, O and S, and optionally containing unsaturation; and $R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation.

For example, n is 0.

For example, n is 1.

For example, n is 1 and $R_1$ is unsubstituted or substituted $C_1$-$C_6$ alkyl.

For example, $R_1$ is unsubstituted or substituted methyl, ethyl, n-propyl, i-propyl, n-butyl, s-butyl, t-butyl, n-pentyl, s-pentyl or n-hexyl.

For example, $R_1$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_5$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_1$ is unsubstituted or substituted methoxyl, ethoxyl, propyloxyl or iso-propyloxyl.

For example, $R_1$ is $C_1$-$C_6$ alkoxyl substituted with one or more groups, each of which can be the same or different, selected from fluorine, chlorine, bromine, and iodine.

For example, $R_1$ is fluorine, chlorine, bromine, or iodine.

For example, m is 0.

For example, m is 1.

For example, $R_2$ is H.

For example, $R_2$ is unsubstituted or substituted straight chain methyl, ethyl, propyl, butyl, pentyl, hexyl, heptyl, octyl, or nonyl or branched propyl, butyl, pentyl, hexyl, heptyl, octyl, or nonyl.

For example, $R_2$ is unsubstituted or substituted methyl, ethyl, n-propyl, i-propyl, or 2,2-dimethylpropyl.

For example, $R_2$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is unsubstituted or substituted phenyl or naphthyl.

For example, $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_2$ is phenyl or naphthyl substituted with one or more groups, each of which can be the same or different, selected from unsubstituted or substituted $C_1$-$C_6$ straight chain or $C_3$-$C_6$ branched alkyl.

For example, $R_2$ is phenyl or naphthyl substituted with one or more groups, each of which can be the same or different, selected from unsubstituted or substituted methyl, ethyl, n-propyl, i-propyl, n-butyl, s-butyl, and t-butyl.

For example, $R_2$ is phenyl or naphthyl substituted with one or more groups, each of which can be the same or different, selected from unsubstituted or substituted methoxyl, ethoxyl, propyloxyl and iso-propyloxyl.

For example, $R_2$ is phenyl or naphthyl substituted with one or more groups, each of which can be the same or different, selected from fluorine, chlorine, bromine, and iodine.

For example, $R_2$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzothiadiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted with one or more groups, each of which can be the same or different, selected from hydroxyl, halogen, nitro, cyano, and unsubstituted or substituted $C_1$-$C_6$ alkyl, unsubstituted or substituted $C_1$-$C_6$ alkoxyl.

For example, $R_2$ is heteroaryl substituted with one or more groups, each of which can be the same or different, selected from unsubstituted or substituted $C_1$-$C_6$ straight chain or $C_3$-$C_6$ branched alkyl.

For example, $R_2$ is heteroaryl substituted with one or more groups, each of which can be the same or different, selected from unsubstituted or substituted methyl, ethyl, n-propyl, i-propyl, n-butyl, s-butyl, and t-butyl.

For example, $R_2$ is heteroaryl substituted with one or more groups, each of which can be the same or different, selected from fluorine, chlorine, bromine, and iodine.

For example, $R_2$ is pyridinyl, thiophenyl, isoxazolyl, benzofuranyl, benzothiophenyl, benzoimidazolyl, or benzothiadiazolyl.

For example, $R_2$ is unsubstituted or substituted benzothiophenyl.

For example, $R_2$ is cyclopropyl, cyclobutyl, cyclopentyl, cyclohexyl, or cycloheptyl, and is optionally substituted.

For example, $R_2$ is cyclopentyl or cyclohexyl.

For example, $R_2$ is pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_2$ is -$T_r$-$R_r$.

For example, $R_5$, $R_6$ and $R_7$ are each independently H.

For example, one or more of $R_5$, $R_6$ and $R_7$ are each independently unsubstituted or substituted $C_1$-$C_6$ straight chain or $C_3$-$C_6$ branched alkyl selected from unsubstituted or substituted methyl, ethyl, n-propyl, i-propyl, n-butyl, s-butyl, and t-butyl.

For example, $T_r$ is unsubstituted or substituted $C_1$-$C_9$ straight chain or $C_3$-$C_9$ branched alkyl linker.

For example, $T_r$ is straight chain methyl, ethyl, propyl, butyl, pentyl, hexyl, heptyl, octyl, or nonyl or branched propyl, butyl, pentyl, hexyl, heptyl, octyl, or nonyl.

For example, $R_r$ is unsubstituted or substituted phenyl or naphthyl.

For example, $R_r$ is phenyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2, 5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2, 5- or 6-member rings and 1-4 heteroatoms selected from N, O and S, and optionally containing unsaturation.

For example, $R_r$ is heteroaryl selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, methylenedioxyphenyl, quinolinyl, isoquinolinyl, naphthrydinyl, indolyl, benzofuranyl, purinyl, deazapurinyl, indolizinyl, and the like, and is optionally substituted.

For example, $R_r$ is cyclopropyl, cyclobutyl, cyclopentyl, cyclohexyl, or cycloheptyl, and is optionally substituted.

For example, $R_r$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl and morpholinyl, and the like, and is optionally substituted.

For example, $R_r$ is a fused polycyclic aromatic moiety.

Representative compounds of the present invention include compounds listed in Table 1.

TABLE 1

| Compound No. | Structure | Chemical Name |
|---|---|---|
| 4 | 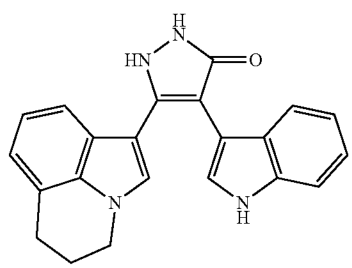 [SMILES: O=c1[nH][nH]c(-c2cn3c4c(cccc24)CCC3)c1-c1c[nH]c2ccccc12] | 5-(5,6-dihydro-4H-pyrrolo[3,2,1-ij]quinolin-1-yl)-4-(1H-indol-3-yl)-1,2-dihydro-3H-pyrazol-3-one |
| 5 | 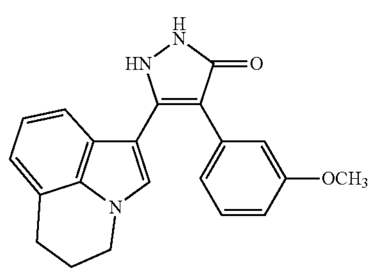 [SMILES: COc1cccc(-c2c(-c3cn4c5c(cccc35)CCC4)[nH][nH]c2=O)c1] | 5-(5,6-dihydro-4H-pyrrolo[3,2,1-ij]quinolin-1-yl)-4-(3-methoxyphenyl)-1H-pyrazol-3(2H)-one |
| 7 | 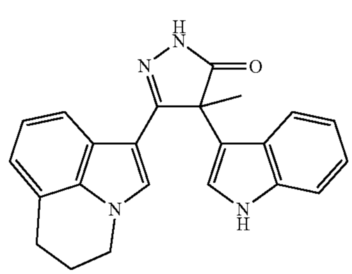 [SMILES: CC1(c2c[nH]c3ccccc23)C(=O)NN=C1c1cn2c3c(cccc13)CCC2] | 3-(5,6-dihydro-4H-pyrrolo[3,2,1-ij]quinolin-1-yl)-4-(1H-indol-3-yl)-4-methyl-1H-pyrazol-5(4H)-one |

TABLE 1-continued

| Compound No. | Structure | Chemical Name |
| --- | --- | --- |
| 10 | 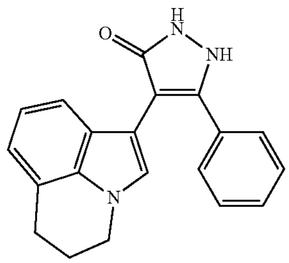 [SMILES: O=c1[nH][nH]c(-c2ccccc2)c1-c1cn2c3c(cccc13)CCC2] | 4-(5,6-dihydro-4H-pyrrolo[3,2,1-ij]quinolin-1-yl)-5-phenyl-1,2-dihydro-3H-pyrazol-3-one |
| 11 | 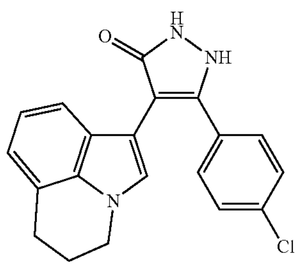 [SMILES: O=c1[nH][nH]c(-c2ccc(Cl)cc2)c1-c1cn2c3c(cccc13)CCC2] | 5-(4-chlorophenyl)-4-(5,6-dihydro-4H-pyrrolo[3,2,1-ij]quinolin-1-yl)-1,2-dihydro-3H-pyrazol-3-one |
| 12 | 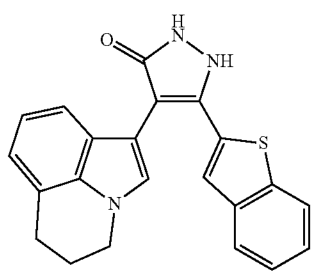 [SMILES: O=c1[nH][nH]c(-c2cc3ccccc3s2)c1-c1cn2c3c(cccc13)CCC2] | 5-(1-benzothien-2-yl)-4-(5,6-dihydro-4H-pyrrolo[3,2,1-ij]quinolin-1-yl)-1,2-dihydro-3H-pyrazol-3-one |
| 13 | 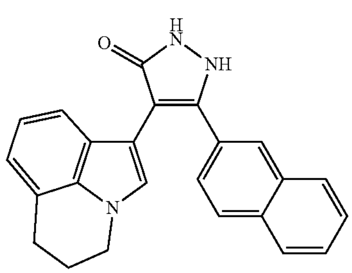 [SMILES: O=c1[nH][nH]c(-c2ccc3ccccc3c2)c1-c1cn2c3c(cccc13)CCC2] | 4-(5,6-dihydro-4H-pyrrolo[3,2,1-ij]quinolin-1-yl)-5-(2-naphthyl)-1,2-dihydro-3H-pyrazol-3-one |
| 14 | 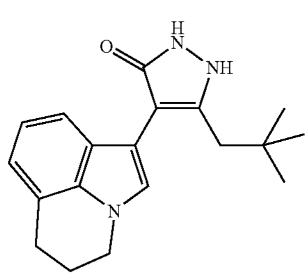 [SMILES: CC(C)(C)Cc1[nH][nH]c(=O)c1-c1cn2c3c(cccc13)CCC2] | 4-(5,6-dihydro-4H-pyrrolo[3,2,1-ij]quinolin-1-yl)-5-(2,2-dimethylpropyl)-1,2-dihydro-3H-pyrazol-3-one |

TABLE 1-continued

| Compound No. | Structure | Chemical Name |
|---|---|---|
| 15 | 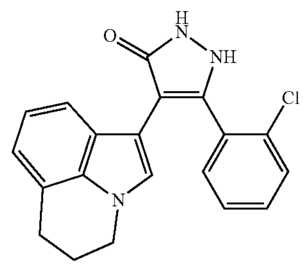 [SMILES: O=c1[nH][nH]c(-c2ccccc2Cl)c1-c1cn2c3c(cccc13)CCC2] | 5-(2-chlorophenyl)-4-(5,6-dihydro-4H-pyrrolo[3,2,1-ij]quinolin-1-yl)-1,2-dihydro-3H-pyrazol-3-one |
| 16 | 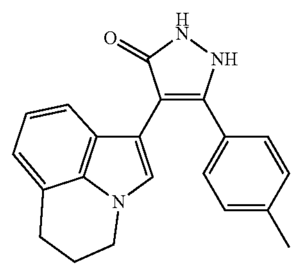 [SMILES: Cc1ccc(-c2[nH][nH]c(=O)c2-c2cn3c4c(cccc24)CCC3)cc1] | 4-(5,6-dihydro-4H-pyrrolo[3,2,1-ij]quinolin-1-yl)-5-(4-methylphenyl)-1,2-dihydro-3H-pyrazol-3-one |
| 17 | 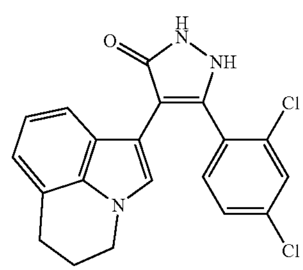 [SMILES: O=c1[nH][nH]c(-c2ccc(Cl)cc2Cl)c1-c1cn2c3c(cccc13)CCC2] | 5-(2,4-dichlorophenyl)-4-(5,6-dihydro-4H-pyrrolo[3,2,1-ij]quinolin-1-yl)-1,2-dihydro-3H-pyrazol-3-one |
| 18 | 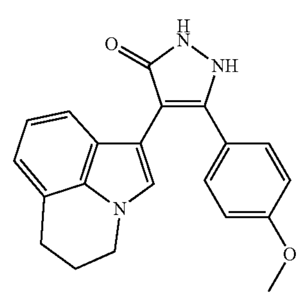 [SMILES: COc1ccc(-c2[nH][nH]c(=O)c2-c2cn3c4c(cccc24)CCC3)cc1] | 4-(5,6-dihydro-4H-pyrrolo[3,2,1-ij]quinolin-1-yl)-5-(4-methoxyphenyl)-1,2-dihydro-3H-pyrazol-3-one |
| 19 | 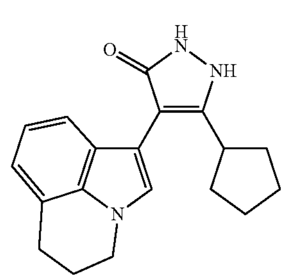 [SMILES: O=c1[nH][nH]c(C2CCCC2)c1-c1cn2c3c(cccc13)CCC2] | 5-cyclopentyl-4-(5,6-dihydro-4H-pyrrolo[3,2,1-ij]quinolin-1-yl)-1,2-dihydro-3H-pyrazol-3-one |

TABLE 1-continued

| Compound No. | Structure | Chemical Name |
|---|---|---|
| 20 | 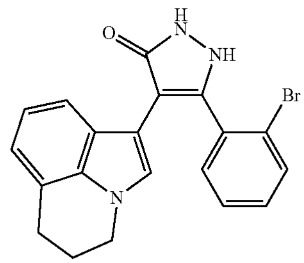 [SMILES: O=c1[nH][nH]c(-c2ccccc2Br)c1-c1cn2c3c(cccc13)CCC2] | 5-(2-bromophenyl)-4-(5,6-dihydro-4H-pyrrolo[3,2,1-ij]quinolin-1-yl)-1,2-dihydro-3H-pyrazol-3-one |
| 21 | 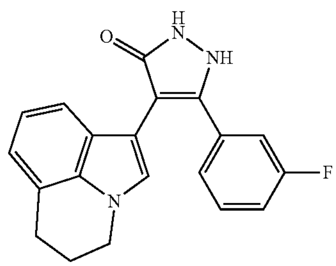 [SMILES: O=c1[nH][nH]c(-c2cccc(F)c2)c1-c1cn2c3c(cccc13)CCC2] | 4-(5,6-dihydro-4H-pyrrolo[3,2,1-ij]quinolin-1-yl)-5-(3-fluorophenyl)-1,2-dihydro-3H-pyrazol-3-one |
| 22 | 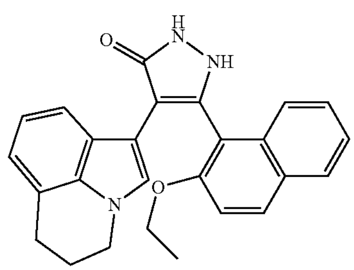 [SMILES: CCOc1ccc2ccccc2c1-c1[nH][nH]c(=O)c1-c1cn2c3c(cccc13)CCC2] | 4-(5,6-dihydro-4H-pyrrolo[3,2,1-ij]quinolin-1-yl)-5-(2-ethoxy-1-naphthyl)-1,2-dihydro-3H-pyrazol-3-one |
| 23 | 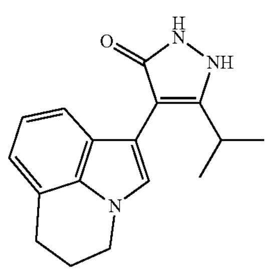 [SMILES: CC(C)c1[nH][nH]c(=O)c1-c1cn2c3c(cccc13)CCC2] | 4-(5,6-dihydro-4H-pyrrolo[3,2,1-ij]quinolin-1-yl)-5-isopropyl-1,2-dihydro-3H-pyrazol-3-one |
| 28 | 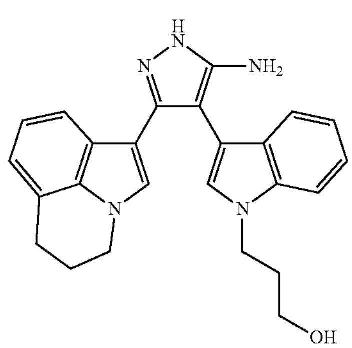 [SMILES: Nc1[nH]nc(-c2cn3c4c(cccc24)CCC3)c1-c1cn(CCCO)c2ccccc12] | 3-{3-[5-amino-3-(5,6-dihydro-4H-pyrrolo[3,2,1-ij]quinolin-1-yl)-1H-pyrazol-4-yl]-1H-indol-1-yl}propan-1-ol |

TABLE 1-continued

| Compound No. | Structure | Chemical Name |
|---|---|---|
| 34 | 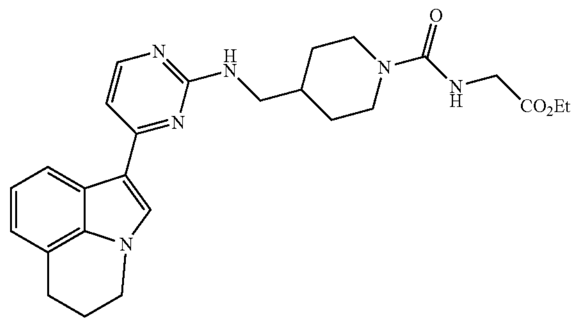 [SMILES: CCOC(=O)CNC(=O)N1CCC(CNc2nccc(-c3cn4c5c(cccc35)CCC4)n2)CC1] | ethyl 2-(4-((4-(5,6-dihydro-4H-pyrrolo[3,2,1-ij]quinolin-1-yl)pyrimidin-2-ylamino)methyl)piperidine-1-carboxamido)acetate |
| 35 | 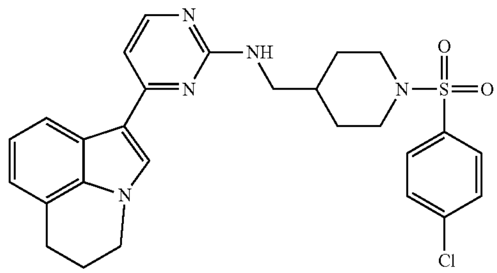 [SMILES: O=S(=O)(c1ccc(Cl)cc1)N1CCC(CNc2nccc(-c3cn4c5c(cccc35)CCC4)n2)CC1] | N-((1-(4-chlorophenylsulfonyl)piperidin-4-yl)methyl)-4-(5,6-dihydro-4H-pyrrolo[3,2,1-ij]quinolin-1-yl)pyrimidin-2-amine |
| 36 | 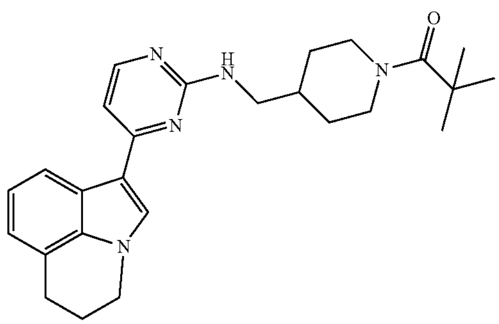 [SMILES: CC(C)(C)C(=O)N1CCC(CNc2nccc(-c3cn4c5c(cccc35)CCC4)n2)CC1] | 1-(4-((4-(5,6-dihydro-4H-pyrrolo[3,2,1-ij]quinolin-1-yl)pyrimidin-2-ylamino)methyl)piperidin-1-yl)-2,2-dimethylpropan-1-one |
| 37 | 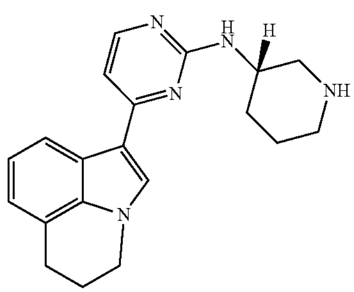 [SMILES: c1cc2c3c(c1)c(-c1ccnc(N[C@H]4CCCNC4)n1)cn3CCC2] | (S)-4-(5,6-dihydro-4H-pyrrolo[3,2,1-ij]quinolin-1-yl)-N-(piperidin-3-yl)pyrimidin-2-amine |
| 38 | 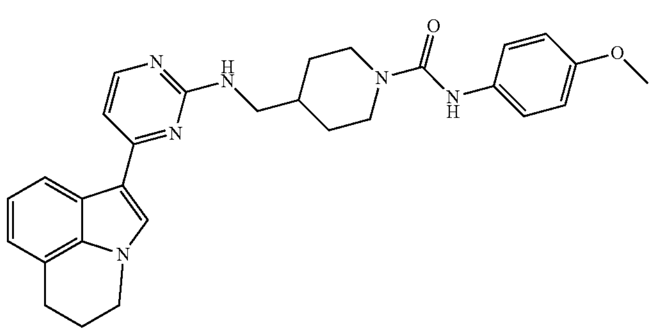 [SMILES: COc1ccc(NC(=O)N2CCC(CNc3nccc(-c4cn5c6c(cccc46)CCC5)n3)CC2)cc1] | 4-((4-(5,6-dihydro-4H-pyrrolo[3,2,1-ij]quinolin-1-yl)pyrimidin-2-ylamino)methyl)-N-(4-methoxyphenyl)piperidine-1-carboxamide |

TABLE 1-continued

| Compound No. | Structure | Chemical Name |
|---|---|---|
| 39 | 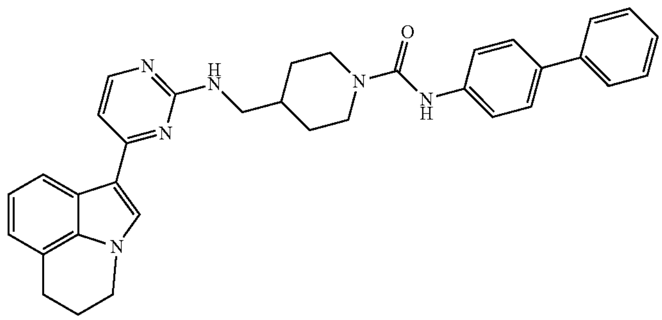 [SMILES: O=C(Nc1ccc(-c2ccccc2)cc1)N1CCC(CNc2nccc(-c3cn4c5c(cccc35)CCC4)n2)CC1] | N-(biphenyl-4-yl)-4-((4-(5,6-dihydro-4H-pyrrolo[3,2,1-ij]quinolin-1-yl)pyrimidin-2-ylamino)methyl)piperidine-1-carboxamide |
| 40 | 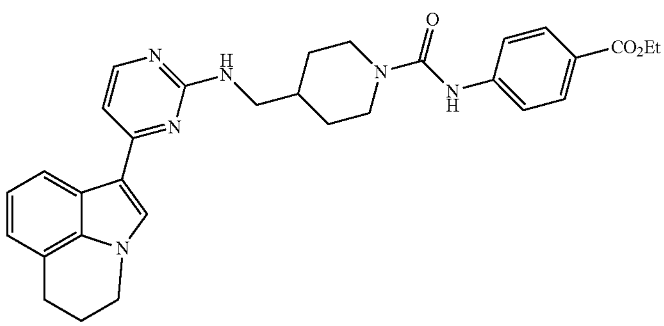 [SMILES: CCOC(=O)c1ccc(NC(=O)N2CCC(CNc3nccc(-c4cn5c6c(cccc46)CCC5)n3)CC2)cc1] | ethyl 4-(4-((4-(5,6-dihydro-4H-pyrrolo[3,2,1-ij]quinolin-1-yl)pyrimidin-2-ylamino)methyl)piperidine-1-carboxamido)benzoate |
| 41 | 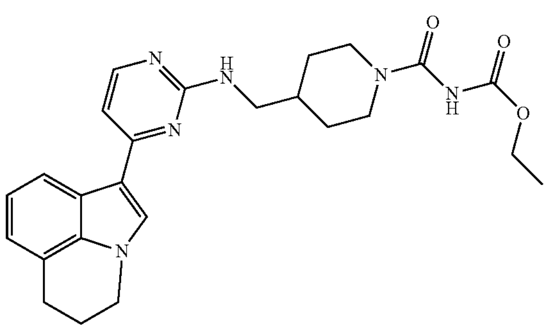 [SMILES: CCOC(=O)NC(=O)N1CCC(CNc2nccc(-c3cn4c5c(cccc35)CCC4)n2)CC1] | ethyl 4-((4-(5,6-dihydro-4H-pyrrolo[3,2,1-ij]quinolin-1-yl)pyrimidin-2-ylamino)methyl)piperidine-1-carbonylcarbamate |
| 42 | 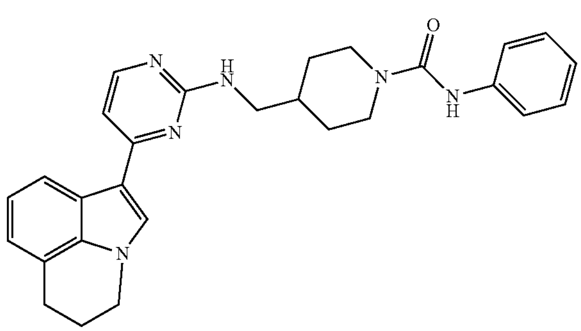 [SMILES: O=C(Nc1ccccc1)N1CCC(CNc2nccc(-c3cn4c5c(cccc35)CCC4)n2)CC1] | 4-((4-(5,6-dihydro-4H-pyrrolo[3,2,1-ij]quinolin-1-yl)pyrimidin-2-ylamino)methyl)-N-phenylpiperidine-1-carboxamide |

TABLE 1-continued

| Compound No. | Structure | Chemical Name |
|---|---|---|
| 43 | 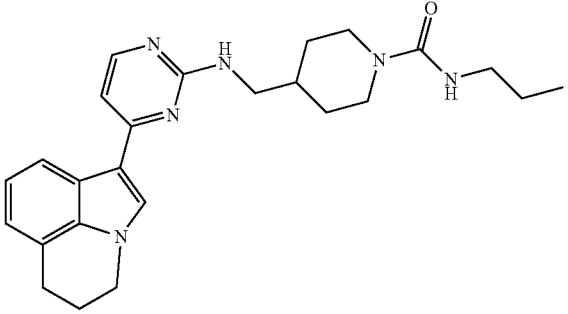 [SMILES: CCCNC(=O)N1CCC(CNc2nccc(-c3cn4c5c(cccc35)CCC4)n2)CC1] | 4-((4-(5,6-dihydro-4H-pyrrolo[3,2,1-ij]quinolin-1-yl)pyrimidin-2-ylamino)methyl)-N-propylpiperidine-1-carboxamide |
| 44 | 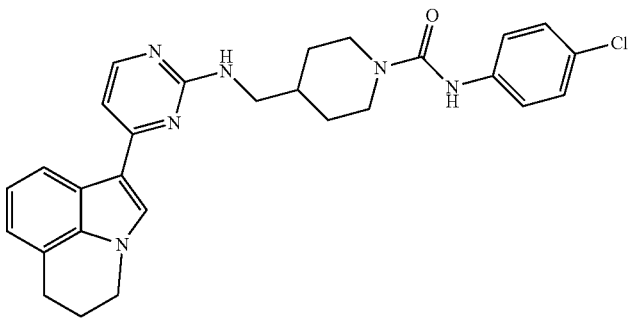 [SMILES: O=C(Nc1ccc(Cl)cc1)N1CCC(CNc2nccc(-c3cn4c5c(cccc35)CCC4)n2)CC1] | N-(4-chlorophenyl)-4-((4-(5,6-dihydro-4H-pyrrolo[3,2,1-ij]quinolin-1-yl)pyrimidin-2-ylamino)methyl)piperidine-1-carboxamide |
| 45 | 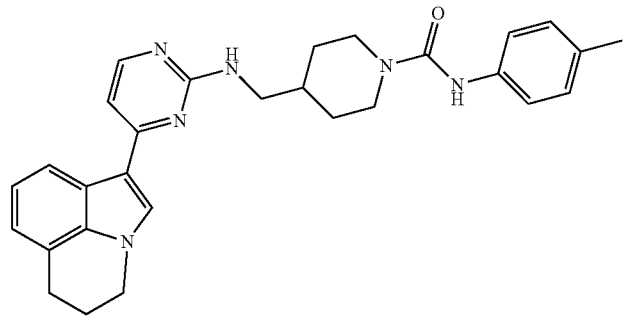 [SMILES: Cc1ccc(NC(=O)N2CCC(CNc3nccc(-c4cn5c6c(cccc46)CCC5)n3)CC2)cc1] | 4-((4-(5,6-dihydro-4H-pyrrolo[3,2,1-ij]quinolin-1-yl)pyrimidin-2-ylamino)methyl)-N-p-tolylpiperidine-1-carboxamide |
| 46 | 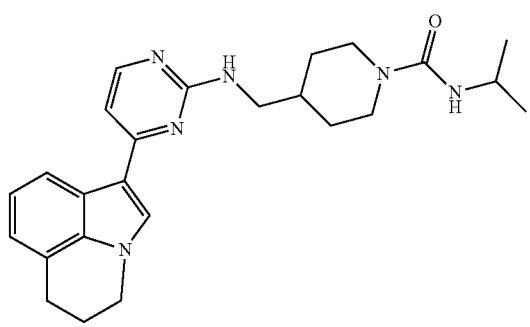 [SMILES: CC(C)NC(=O)N1CCC(CNc2nccc(-c3cn4c5c(cccc35)CCC4)n2)CC1] | 4-((4-(5,6-dihydro-4H pyrrolo[3,2,1-ij]quinolin-1-yl)pyrimidin-2-ylamino)methyl)-N-isopropylpiperidine-1-carboxamide |

TABLE 1-continued

| Compound No. | Structure | Chemical Name |
| --- | --- | --- |
| 47 | 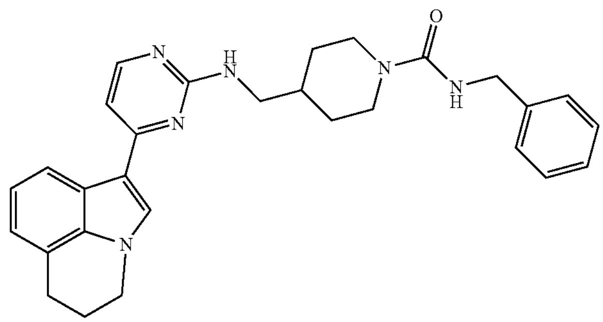 [SMILES: O=C(NCc1ccccc1)N1CCC(CNc2nccc(-c3cn4c5c(cccc35)CCC4)n2)CC1] | N-benzyl-4-((4-(5,6-dihydro-4H-pyrrolo[3,2,1-ij]quinolin-1-yl)pyrimidin-2-ylamino)methyl)piperidine-1-carboxamide |
| 48 | 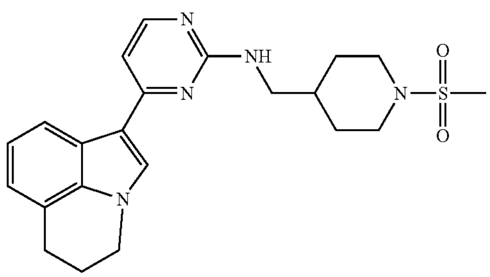 [SMILES: CS(=O)(=O)N1CCC(CNc2nccc(-c3cn4c5c(cccc35)CCC4)n2)CC1] | 4-(5,6-dihydro-4H-pyrrolo[3,2,1-ij]quinolin-1-yl)-N-((1-(methylsulfonyl)piperidin-4-yl)methyl)pyrimidin-2-amine |
| 49 | 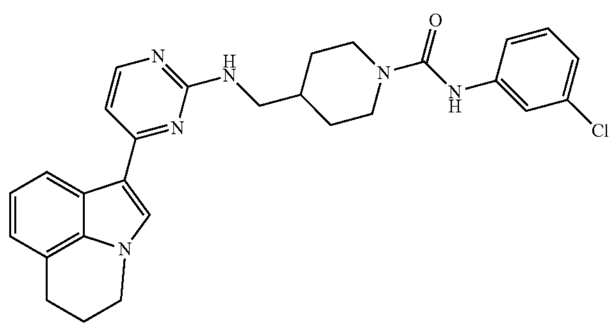 [SMILES: O=C(Nc1cccc(Cl)c1)N1CCC(CNc2nccc(-c3cn4c5c(cccc35)CCC4)n2)CC1] | N-(3-chlorophenyl)-4-((4-(5,6-dihydro-4H-pyrrolo[3,2,1-ij]quinolin-1-yl)pyrimidin-2-ylamino)methyl)piperidine-1-carboxamide |
| 50 | 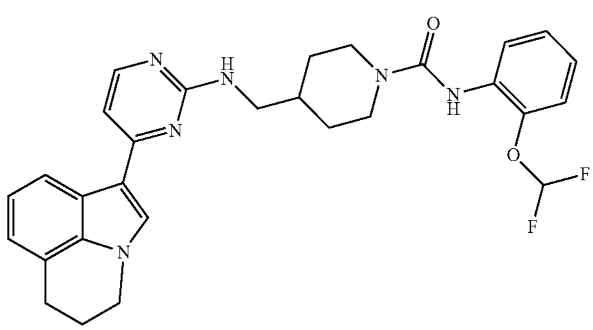 [SMILES: O=C(Nc1ccccc1OC(F)F)N1CCC(CNc2nccc(-c3cn4c5c(cccc35)CCC4)n2)CC1] | N-(2-(difluoromethoxy)phenyl)-4-((4-(5,6-dihydro-4H-pyrrolo[3,2,1-ij]quinolin-1-yl)pyrimidin-2-ylamino)methyl)piperidine-1-carboxamide |
| 51 | 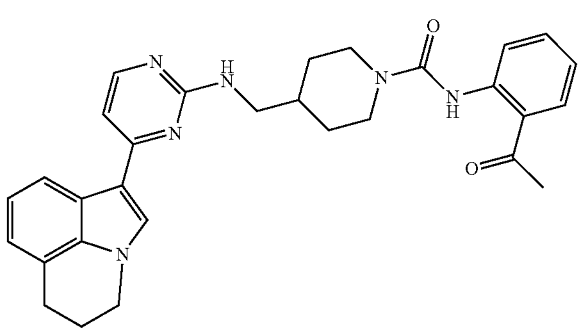 [SMILES: CC(=O)c1ccccc1NC(=O)N1CCC(CNc2nccc(-c3cn4c5c(cccc35)CCC4)n2)CC1] | N-(2-acetylphenyl)-4-((4-(5,6-dihydro-4H-pyrrolo[3,2,1-ij]quinolin-1-yl)pyrimidin-2-ylamino)methyl)piperidine-1-carboxamide |

TABLE 1-continued

| Compound No. | Structure | Chemical Name |
|---|---|---|
| 52 | 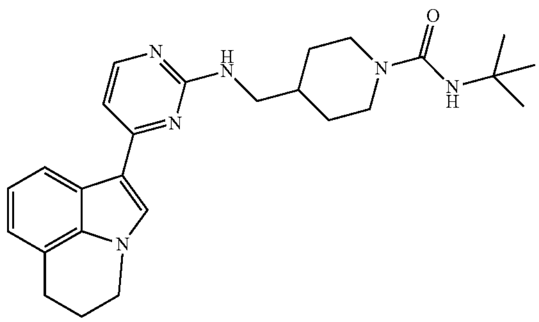 [SMILES: CC(C)(C)NC(=O)N1CCC(CNc2nccc(-c3cn4c5c(cccc35)CCC4)n2)CC1] | N-tert-butyl-4-((4-(5,6-dihydro-4H-pyrrolo[3,2,1-ij]quinolin-1-yl)pyrimidin-2-ylamino)methyl)piperidine-1-carboxamide |
| 53 | 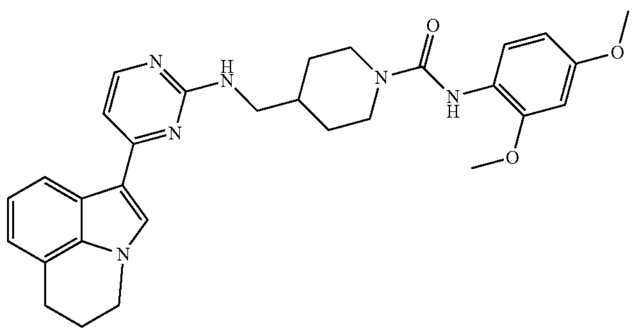 [SMILES: COc1ccc(NC(=O)N2CCC(CNc3nccc(-c4cn5c6c(cccc46)CCC5)n3)CC2)c(OC)c1] | 4-((4-(5,6-dihydro-4H-pyrrolo[3,2,1-ij]quinolin-1-yl)pyrimidin-2-ylamino)methyl)-N-(2,4-dimethoxyphenyl)piperidine-1-carboxamide |
| 54 | 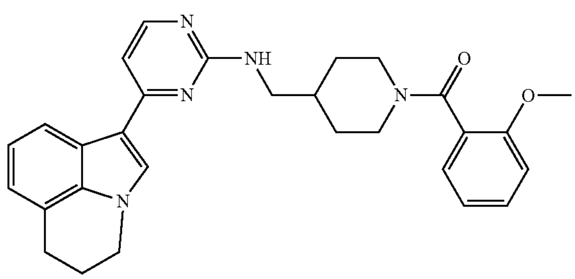 [SMILES: COc1ccccc1C(=O)N1CCC(CNc2nccc(-c3cn4c5c(cccc35)CCC4)n2)CC1] | (4-((4-(5,6-dihydro-4H-pyrrolo[3,2,1-ij]quinolin-1-yl)pyrimidin-2-ylamino)methyl)piperidin-1-yl)(2-methoxyphenyl)methanone |
| 56 | 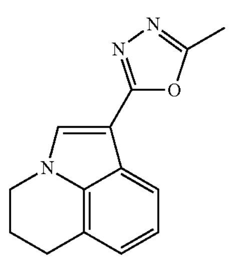 [SMILES: Cc1nnc(-c2cn3c4c(cccc24)CCC3)o1] | 1-(5-methyl-1,3,4-oxadiazol-2-yl)-5,6-dihydro-4H-pyrrolo[3,2,1-ij]quinoline |
| 57 | 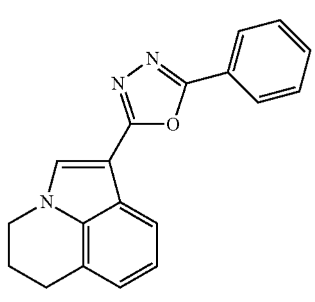 [SMILES: c1ccc(-c2nnc(-c3cn4c5c(cccc35)CCC4)o2)cc1] | 1-(5-phenyl-1,3,4-oxadiazol-2-yl)-5,6-dihydro-4H-pyrrolo[3,2,1-ij]quinoline |

TABLE 1-continued

| Compound No. | Structure | Chemical Name |
|---|---|---|
| 58 | 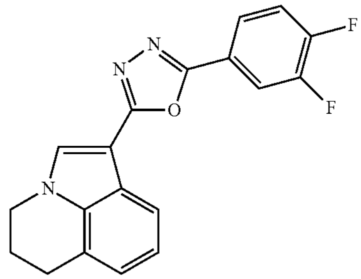 [SMILES: Fc1ccc(-c2nnc(-c3cn4c5c(cccc35)CCC4)o2)cc1F] | 1-[5-(3,4-difluorophenyl)-1,3,4-oxadiazol-2-yl]-5,6-dihydro-4H-pyrrolo[3,2,1-ij]quinoline |
| 59 | 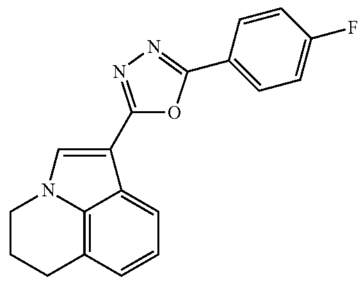 [SMILES: Fc1ccc(-c2nnc(-c3cn4c5c(cccc35)CCC4)o2)cc1] | 1-[5-(4-fluorophenyl)-1,3,4-oxadiazol-2-yl]-5,6-dihydro-4H-pyrrolo[3,2,1-ij]quinoline |
| 60 | 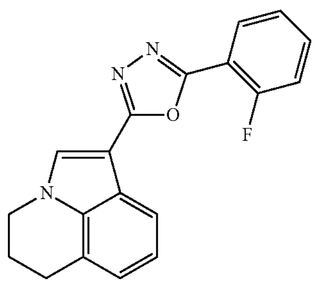 [SMILES: Fc1ccccc1-c1nnc(-c2cn3c4c(cccc24)CCC3)o1] | 1-[5-(2-fluorophenyl)-1,3,4-oxadiazol-2-yl]-5,6-dihydro-4H-pyrrolo[3,2,1-ij]quinoline |
| 61 | 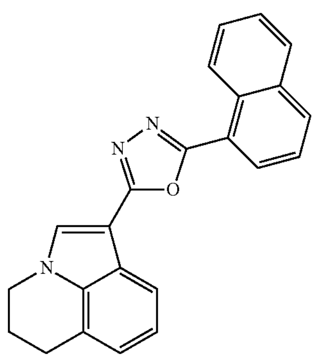 [SMILES: c1ccc2c(-c3nnc(-c4cn5c6c(cccc46)CCC5)o3)cccc2c1] | 1-[5-(1-naphthyl)-1,3,4-oxadiazol-2-yl]-5,6-dihydro-4H-pyrrolo[3,2,1-ij]quinoline |
| 62 | 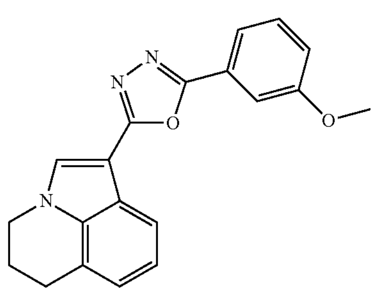 [SMILES: COc1cccc(-c2nnc(-c3cn4c5c(cccc35)CCC4)o2)c1] | 1-[5-(3-methoxyphenyl)-1,3,4-oxadiazol-2-yl]-5,6-dihydro-4H-pyrrolo[3,2,1-ij]quinoline |

TABLE 1-continued

| Compound No. | Structure | Chemical Name |
| --- | --- | --- |
| 63 | 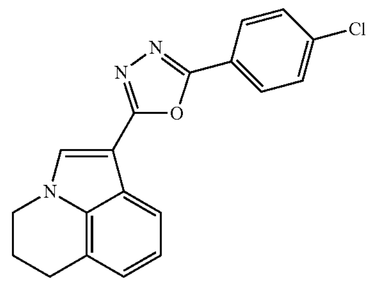 [SMILES: Clc1ccc(-c2nnc(-c3cn4c5c(cccc35)CCC4)o2)cc1] | 1-[5-(4-chlorophenyl)-1,3,4-oxadiazol-2-yl]-5,6-dihydro-4H-pyrrolo[3,2,1-ij]quinoline |
| 64 | 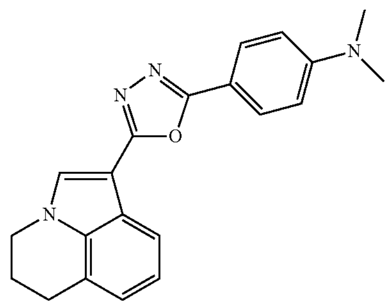 [SMILES: CN(C)c1ccc(-c2nnc(-c3cn4c5c(cccc35)CCC4)o2)cc1] | 4-[5-(5,6-dihydro-4H-pyrrolo[3,2,1-ij]quinolin-1-yl)-1,3,4-oxadiazol-2-yl]-N,N-dimethylaniline |
| 65 | 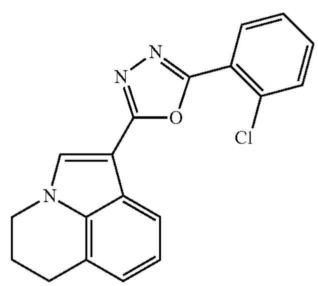 [SMILES: Clc1ccccc1-c1nnc(-c2cn3c4c(cccc24)CCC3)o1] | 1-[5-(2-chlorophenyl)-1,3,4-oxadiazol-2-yl]-5,6-dihydro-4H-pyrrolo[3,2,1-ij]quinoline |
| 66 | 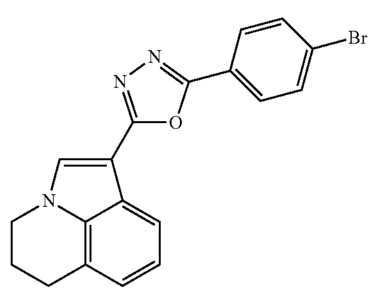 [SMILES: Brc1ccc(-c2nnc(-c3cn4c5c(cccc35)CCC4)o2)cc1] | 1-[5-(4-bromophenyl)-1,3,4-oxadiazol-2-yl]-5,6-dihydro-4H-pyrrolo[3,2,1-ij]quinoline |
| 67 | 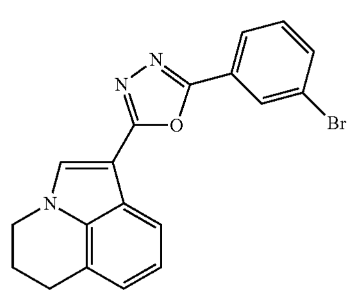 [SMILES: Brc1cccc(-c2nnc(-c3cn4c5c(cccc35)CCC4)o2)c1] | 1-[5-(3-bromophenyl)-1,3,4-oxadiazol-2-yl]-5,6-dihydro-4H-pyrrolo[3,2,1-ij]quinoline |

TABLE 1-continued

| Compound No. | Structure | Chemical Name |
|---|---|---|
| 68 | 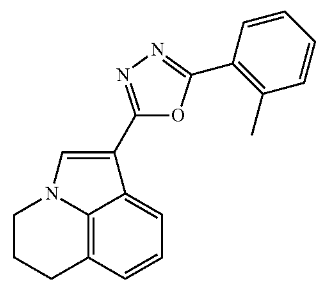 [SMILES: Cc1ccccc1-c1nnc(-c2cn3c4c(cccc24)CCC3)o1] | 1-[5-(2-methylphenyl)-1,3,4-oxadiazol-2-yl]-5,6-dihydro-4H-pyrrolo[3,2,1-ij]quinoline |
| 69 | 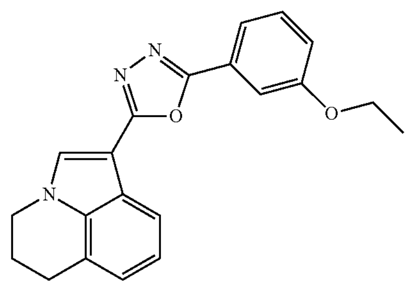 [SMILES: CCOc1cccc(-c2nnc(-c3cn4c5c(cccc35)CCC4)o2)c1] | 1-[5-(3-ethoxyphenyl)-1,3,4-oxadiazol-2-yl]-5,6-dihydro-4H-pyrrolo[3,2,1-ij]quinoline |
| 70 | 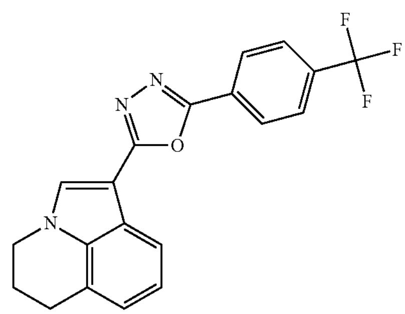 [SMILES: FC(F)(F)c1ccc(-c2nnc(-c3cn4c5c(cccc35)CCC4)o2)cc1] | 1-{5-[4-(trifluoromethyl)phenyl]-1,3,4-oxadiazol-2-yl}-5,6-dihydro-4H-pyrrolo[3,2,1-ij]quinoline |
| 71 | 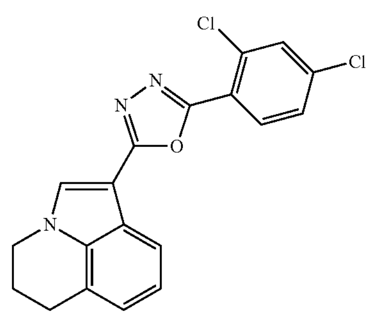 [SMILES: Clc1ccc(-c2nnc(-c3cn4c5c(cccc35)CCC4)o2)c(Cl)c1] | 1-[5-(2,4-dichlorophenyl)-1,3,4-oxadiazol-2-yl]-5,6-dihydro-4H-pyrrolo[3,2,1-ij]quinoline |
| 72 | 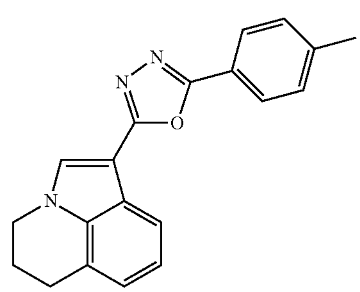 [SMILES: Cc1ccc(-c2nnc(-c3cn4c5c(cccc35)CCC4)o2)cc1] | 1-[5-(4-methylphenyl)-1,3,4-oxadiazol-2-yl]-5,6-dihydro-4H-pyrrolo[3,2,1-ij]quinoline |

TABLE 1-continued

| Compound No. | Structure | Chemical Name |
| --- | --- | --- |
| 73 | 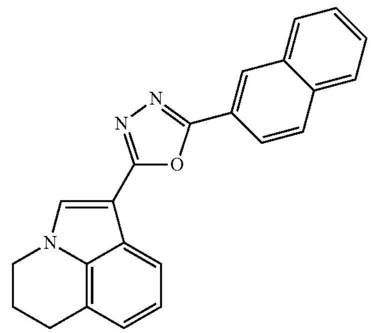 [SMILES: c1ccc2cc(-c3nnc(-c4cn5c6c(cccc46)CCC5)o3)ccc2c1] | 1-(5-naphthalen-2-yl-1,3,4-oxadiazol-2-yl)-5,6-dihydro-4H-pyrrolo[3,2,1-ij]quinoline |
| 74 | 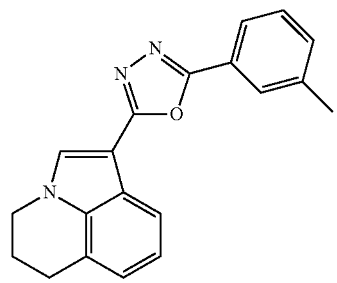 [SMILES: Cc1cccc(-c2nnc(-c3cn4c5c(cccc35)CCC4)o2)c1] | 1-[5-(3-methylphenyl)-1,3,4-oxadiazol-2-yl]-5,6-dihydro-4H-pyrrolo[3,2,1-ij]quinoline |
| 75 | 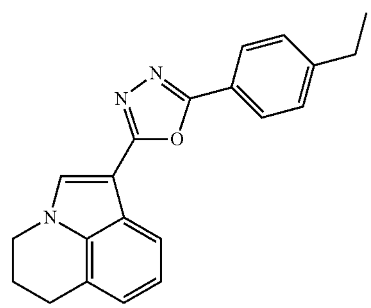 [SMILES: CCc1ccc(-c2nnc(-c3cn4c5c(cccc35)CCC4)o2)cc1] | 1-[5-(4-ethylphenyl)-1,3,4-oxadiazol-2-yl]-5,6-dihydro-4H-pyrrolo[3,2,1-ij]quinoline |
| 76 | 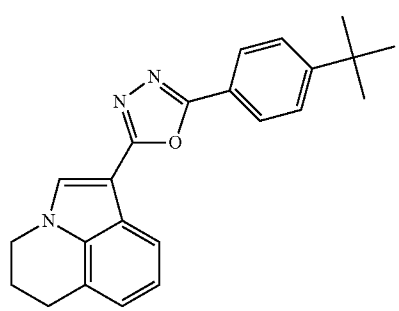 [SMILES: CC(C)(C)c1ccc(-c2nnc(-c3cn4c5c(cccc35)CCC4)o2)cc1] | 1-[5-(4-tert-butylphenyl)-1,3,4-oxadiazol-2-yl]-5,6-dihydro-4H-pyrrolo[3,2,1-ij]quinoline |
| 79 | 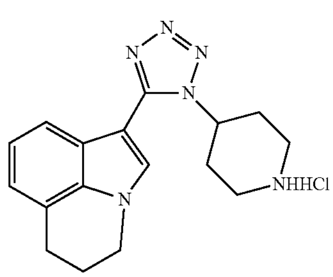 | 1-(1-(piperidin-4-yl)-1H-tetrazol-5-yl)-5,6-dihydro-4H-pyrrolo[3,2,1-ij]quinoline Hydrochloride |

TABLE 1-continued

| Compound No. | Structure | Chemical Name |
|---|---|---|
| 80 | 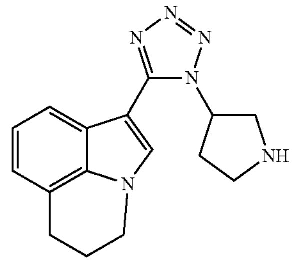 [SMILES: c1cc2c3c(c1)c(-c1nnnn1C1CCNC1)cn3CCC2] | 1-(1-pyrrolidin-3-yl-1H-tetrazol-5-yl)-5,6-dihydro-4H-pyrrolo[3,2,1-ij]quinoline |
| 81 | 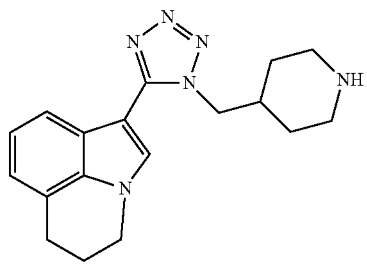 [SMILES: c1cc2c3c(c1)c(-c1nnnn1CC1CCNCC1)cn3CCC2] | 1-[1-(piperidin-4-ylmethyl)-1H-tetrazol-5-yl]-5,6-dihydro-4H-pyrrolo[3,2,1-ij]quinoline |
| 82 | 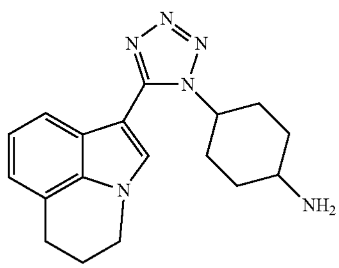 [SMILES: NC1CCC(n2nnnc2-c2cn3c4c(cccc24)CCC3)CC1] | 4-[5-(5,6-dihydro-4H-pyrrolo[3,2,1-ij]quinolin-1-yl)-1H-tetrazol-1-yl]cyclohexanamine |
| 83 | 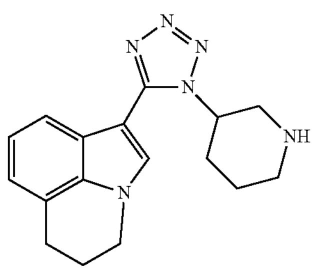 [SMILES: c1cc2c3c(c1)c(-c1nnnn1C1CCCNC1)cn3CCC2] | 1-(1-piperidin-3-yl-1H-tetrazol-5-yl)-5,6-dihydro-4H-pyrrolo[3,2,1-ij]quinoline |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

As used herein, "alkyl linker" is intended to include $C_1, C_2, C_3, C_4, C_5$ or $C_6$ straight chain (linear) saturated aliphatic hydrocarbon groups and $C_3, C_4, C_5$ or $C_6$ branched saturated aliphatic hydrocarbon groups. For example, $C_1$-$C_6$ alkyl linker is intended to include $C_1, C_2, C_3, C_4, C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]cyclooctane, [4.3.0]bicyclononane, [4.4.0] bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atmos on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O—.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "linker," as used herein, refers to a chemical moiety that bonds to two additional chemical moieties, thereby forming linkage between the additional chemical moieties. Non-limiting examples of linkers include $C_1$-$C_{24}$ alkylene, $C_2$-$C_{24}$ alkenylene, $C_2$-$C_{24}$ alkynylene, $C_5$-$C_{24}$ arylene, $C_6$-$C_{24}$ aralkylene, and $C_6$-$C_{24}$ alkarylene, any of which may contain one or more substituents and one or more heteroatoms. Examples of specific linkers include methylene, ethylene, propylene, ethenylene, ethynylene, phenylene, etc.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula I have Formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. Synthesis of Substituted Heterocyclic Compounds

The present invention provides methods for the synthesis of the compounds of formula I, II, IIa, III, IIIa, IIIb, IV or V. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's *Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with formula I, II, IIa, III, IIIa, IIIb, IV or V may be prepared according to the following procedures from commercially available starting materials or starting materials which can be prepared using literature procedures. These procedures show the preparation of representative compounds of this invention.

General Procedure A

Synthesis of tert-butyl 3-(1-(5,6-dihydro-4H-pyrrolo [3,2,1-ij]quinolin-1-yl)-3-methoxy-1,3-dioxopropan-2-yl)-1H-indole-1-caroxylate (4)

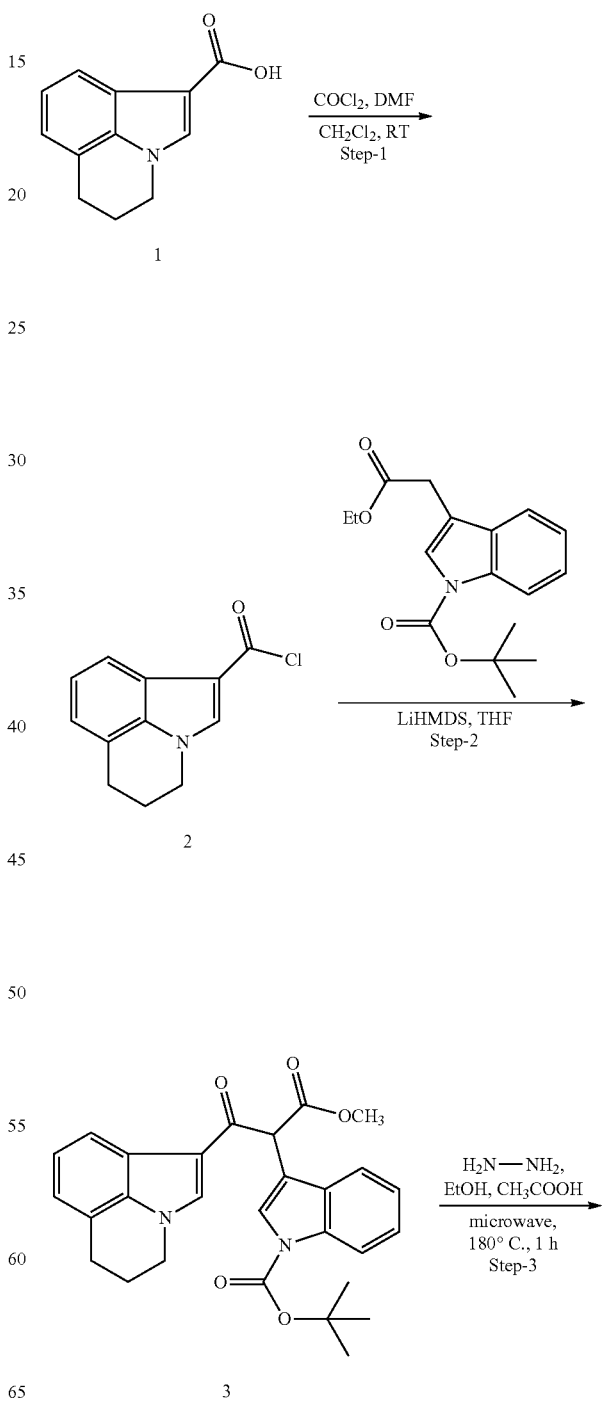

-continued

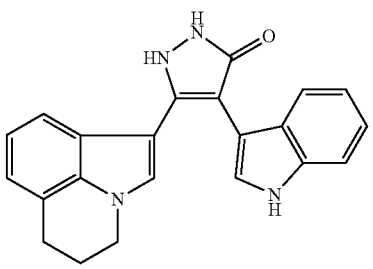

4 purified using flash column chromatography (SiO$_2$, gradient 1% methanol in dichloromethane to 3% methanol in dichloromethane) to give the desired product (1.46 g, 94%) as a white solid. M.p. 170-173° C. 400 MHz $^1$H NMR (CDCl$_3$) δ: 11.02 (s, 1H), 7.38-7.33 (m, 1H), 7.31 (s, 1H), 7.26-7.21 (m, 1H), 7.2-7.16 (m, 1H), 7.1-7.0 (m, 2H), 6.88-6.75 (m, 3H), 4.1-4.02 (m, 2H), 2.94-2.82 (m, 2H), 2.14-2.02 (m, 2H); LCMS [M+H]: 355.2.

General Procedure B

Synthesis of 5-(5,6-dihydro-4H-pyrrolo[3,2,1-ij]quinolin-1-yl)-4-(1H-indol-3-yl)-1H-pyrazol-3(2H)-one (7)

Step 1. Synthesis of 5,6-dihydro-4H-pyrrolo[3,2,1-ij]quinoline-1-carbonyl chloride (2). To a suspension of 5,6-dihydro-4H-pyrrolo[3,2,1-ij]quinoline-1-carboxylic acid (5.41 g, 26.93 mmol) in anhydrous dichloromethane (200 mL) at room temperature was added oxalyl chloride (4.68 mL, 53.86 mmol). On addition the reaction heated up and carbon dioxide was generated. Dimethylformamide (5 drops) was then added and the reaction mixture was stirred at room temperature for 2 hours. The solvent was removed under reduced pressure to yield the crude desired product as a dark oil. The oily residue was dissolved in anhydrous tetrahydrofuran (60 mL) and the solvent removed under reduced pressure. This procedure was repeated once more and the desired product was used in the next reaction without any further purification.

Step 2. Synthesis of tert-butyl 3-(1-(5,6-dihydro-4H-pyrrolo[3,2,1-ij]quinolin-1-yl)-3-methoxy-1,3-dioxopropan-2-yl)-1H-indole-1-carboxylate (3). To a solution of 3-methoxycarbonylmethyl-indole-1-carboxylic acid tert-butyl ester (8.16 g, 26.93 mmol) in anhydrous tetrahydrofuran (80 mL) at –78° C. was added LiHMDS (67.3 mL, 1 M in THF). The reaction mixture was stirred at –78° C. for 30 minutes, then warmed to room temperature and stirred for 1 hour. The reaction mixture was then cooled to –78° C. and then added in a dropwise manner a solution 5,6-dihydro-4H-pyrrolo[3,2,1-ij]quinoline-1-carbonyl chloride (26.93 mmol) in tetrahydrofuran (50 mL). The reaction mixture was stirred at –78° C. for 1 hour and at room temperature for 2 hours. The reaction was quenched by addition of saturated NH$_4$Cl (200 mL) and water (200 mL). The aqueous layer was then extracted EtOAc (400 mL). The organic layer was separated and washed with aqueous NaCl, dried using Na$_2$SO$_4$, filtered and concentrated under reduced pressure. The desired crude product was purified using flash column chromatography (SiO$_2$, gradient 20% EtOAc in hexane to 25% EtOAc in hexane) to gave tert-butyl 3-(1-(5,6-dihydro-4H-pyrrolo[3,2,1-ij]quinolin-1-yl)-3-methoxy-1,3-dioxopropan-2-yl)-1H-indole-1-carboxylate (8.77 g, 67% yield) as a light tan solid. M.p.=86-91° C.; LCMS [M+H]: 487.22.

Step 3. Synthesis of 5-(5,6-dihydro-4H-pyrrolo[3,2,1-ij]quinolin-1-yl)-4-(1H-indol-3-yl)-1H-pyrazol-3(2H)-one (4). To a solution of 3-[2-(5,6-dihydro-4H-pyrrolo[3,2,1-ij]quinolin-1-yl)-1-methoxycarbonyl-2-oxo-ethyl]-indole-1-carboxylic acid tert-butyl ester (2.12 g, 4.36 mmol) in EtOH (25 mL) was added glacial acetic acid (5 mL) followed by hydrazine (35% in water, 2.34 mL). The reaction mixture was microwaved at 180° C. for 1 hour. The solvent was then removed under reduced pressure and the crude product was

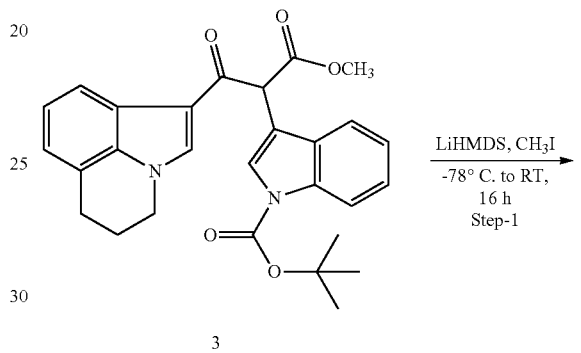

3

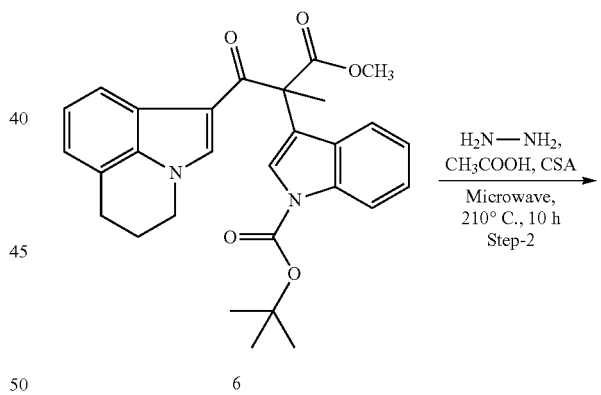

6

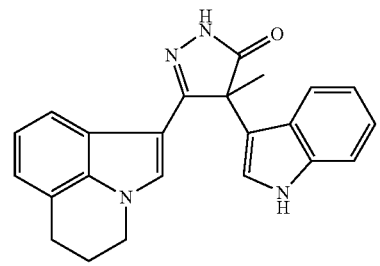

7

Step 1: Synthesis of tert-butyl 3-(1-(5,6-dihydro-4H-pyrrolo[3,2,1-ij]quinolin-1-yl)-3-methoxy-2-methyl-1,3-dioxopropan-2-yl)-1H-indole-1-carboxylate (6). To a solution of tert-butyl 3-(1-(5,6-dihydro-4H-pyrrolo[3,2,1-ij]quinolin-1-yl)-3-methoxy-1,3-dioxopropan-2-yl)-1H-indole-1-carboxylate (3) (0.72 g, 1.49 mmol) in tetrahydrofuran (30 mL) at −78° C. was added LiHMDS (3.73 mL, 1 M in THF). The reaction mixture was stirred at −78° C. for 10 min then at room temperature for 1 hour. Methyl iodide (0.28 mL, 4.47 mmol) was added at room temperature and the reaction mixture was stirred at room temperature for 16 hours. TLC analysis of the reaction showed the presence of unreacted starting material so additional LiHMDS (3.73 mL, 1M in THF) followed by methyl iodide (0.56 mL) was added to the reaction mixture. The reaction mixture was stirred at room temperature for 16 hours. The reaction was quenched by adding saturated NH₄Cl (50 mL) and water (50 mL). The aqueous layer was extracted with EtOAc (2×50 mL). The combined organic layer was washed with aqueous NaCl (50 mL), dried using Na₂SO₄, filtered and concentrated under reduced pressure to give the desired crude product as oil. The desired crude product was purified using flash column chromatography (SiO₂, 20% EtOAc in hexane) to give tert-butyl 3-(1-(5,6-dihydro-4H-pyrrolo[3,2,1-ij]quinolin-1-yl)-3-methoxy-2-methyl-1,3-dioxopropan-2-yl)-1H-indole-1-carboxylate (0.535 g, 71% yield) as a yellow foamy solid. LCMS [M+H]: 487

Step 2: Synthesis of 5-(5,6-dihydro-4H-pyrrolo[3,2,1-ij]quinolin-1-yl)-4-(1H-indol-3-yl)-1H-pyrazol-3(2H)-one (7). To a solution of tert-butyl 3-(1-(5,6-dihydro-4H-pyrrolo[3,2,1-ij]quinolin-1-yl)-3-methoxy-2-methyl-1,3-dioxopropan-2-yl)-1H-indole-1-carboxylate (6) (0.26 g, 0.52 mmol) in glacial acetic acid (2 mL) was added hydrazine (35% in H₂O, 0.25 mL) followed by a catalytic amount of camphor sulfonic acid (10 mg). The reaction mixture was then microwaved at 210° C. for 10 hours. The solvent was then removed under reduced pressure and the residue partitioned between dichloromethane (10 mL) and aqueous Na₂CO₃ (20 mL). The organic layer was separated, dried using Na₂SO₄, filtered and concentrated under reduced pressure. The crude product was purified by reverse phase (HPLC, C-18) chromatography using trifluoroacetic acid as a modifier to give the desired product (7) (0.033 g, 17% yield) as a white solid. 400 MHz ¹H NMR (CDCl₃) δ: 11.44 (s, 1H), 11.18 (s, 1H), 7.91 (d, J=4.2 Hz, 1h), 7.6 (d, J=1.4 Hz, 1H), 7.37-7.28 (m, 2H), 7.15-7.1 (m, 1H), 7.08-6.96 (m, 2H), 6.95-6.88 (m, 1H), 6.82 (t, J=6.8 Hz, 1H), 4.08-3.88 (m, 2H), 2.9-2.78 (m, 2H), 2.08-1.96 (m, 2H), 1.82 (s, 3H); LCMS [M+H]: 369.

General Procedure C

Synthesis of 4-(5,6-dihydro-4H-pyrrolo[3,2,1-ij]quinolin-1-yl)-5-phenyl-1H-pyrazol-3(2H)-one. (10)

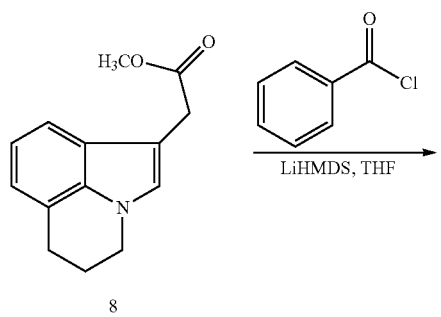

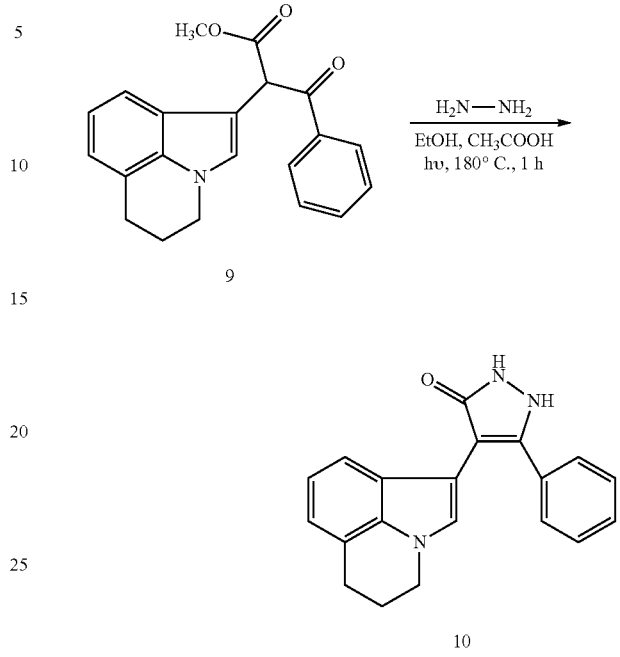

Step 1. Synthesis of methyl 2-(5,6-dihydro-4H-pyrrolo[3,2,1-ij]quinolin-1-yl)-3-oxo-3-phenylpropanoate (9). To a solution of methyl 2-(5,6-dihydro-4H-pyrrolo[3,2,1-ij]quinolin-1-yl)acetate (0.35 g, 1.53 mmol) in anhydrous THF (10 mL) at −78° C. was added LiHMDS (1M solution in THF, 3.82 mL). The reaction was stirred at −78° C. for 15 minutes and then at room temperature for 30 minutes. The reaction mixture was then cooled at −78° C. and benzoyl chloride (0.18 mL, 1.53 mmol) added in a dropwise manner. The reactions mixture was stirred at −78° C. for 1 hour and at room temperature for 2 hours. The reaction was quenched by adding saturated NH₄Cl solution (20 mL) and water (20 mL). The aqueous layer was extracted with EtOAc (40 mL), dried using sodium sulfate and concentrated under reduced pressure. The crude product was purified using flash column chromatography (SiO₂, 20% EtOAc in hexanes) to give the desired product (0.362 g, 71%) as a yellow foamy solid. 400 MHz ¹H NMR (CDCl₃) δ: 8.06-8.0 (m, 2H), 7.62-7.56 (m, 1H), 7.5-7.4 (m, 3H), 7.32 (s, 1H), 6.96-6.86 (m, 1H), 6.85-6.78 (m, 1H), 6.32 (s, 1H), 4.16-4.02 (m, 2H), 3.66 (s, 3H), 2.94-2.8 (m, 2H), 2.14-2.0 (m, 2H); LCMS [M+H]: 334.2.

Step 2. Synthesis of 4-(5,6-dihydro-4H-pyrrolo[3,2,1-ij]quinolin-1-yl)-5-phenyl-1H-pyrazol-3(2H)-one (10). To a solution of methyl 2-(5,6-dihydro-4H-pyrrolo[3,2,1-ij]quinolin-1-yl)-3-oxo-3-phenylpropanoate (0.301 g, 0.90 mmol) was added ethanol (2 mL) and glacial acetic acid (1 mL). Hydrazine monohydrate (0.28 mL, ~6 eq) was then added and the reaction mixture was microwaved at 180° C. for 60 minutes. The solvent was then removed under reduced pressure and the crude product was purified by reverse phase HPLC. The desired product (0.062 g, 22%) was obtained as an tan colored solid. 400 MHz ¹H NMR (CDCl₃) δ: 11.95 (br s, 1H), 9.63 (br s, 1H), 7.5-7.35 (m, 2H), 7.35-7.16 (m, 4H), 6.8-6.74 (m, 1H), 6.72-6.62 (m, 2H), 4.24-4.12 (m, 2H), 2.98-2.86 (m, 2H), 2.22-2.1 (m, 2H); LCMS [M+H]: 316.3.

General Procedure D

Synthesis of 3-(3-(5-amino-3-(5,6-dihydro-4H-pyrrolo[3,2,1-ij]quinolin-1-yl)-1H-pyrazol-4-yl)-1H-indol-1-yl)propan-1-ol (28)

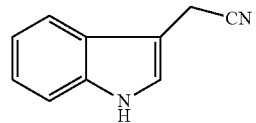 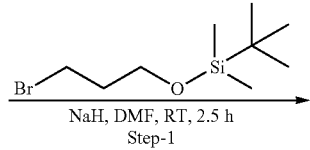 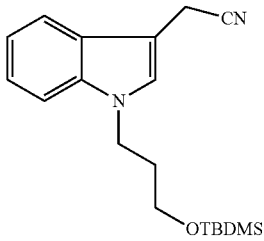 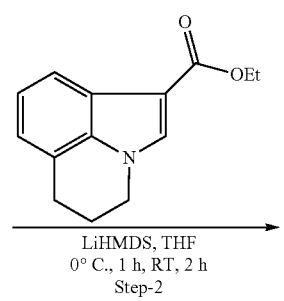

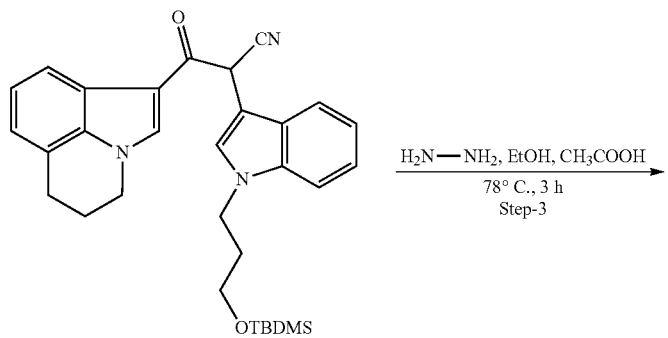

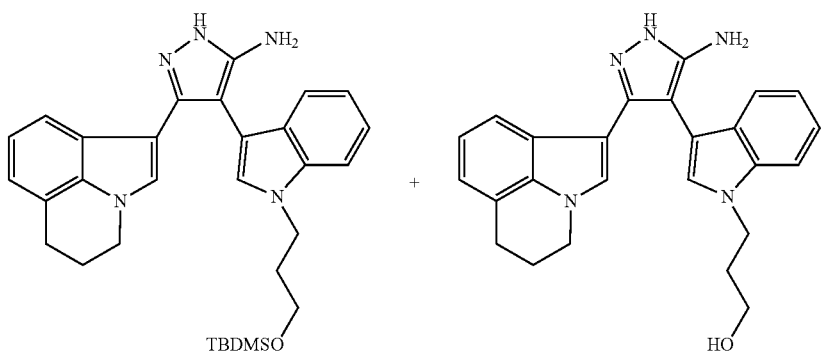

Step 1. Synthesis of 2-(1-(3-(tert-butyldimethylsilyloxy)propyl)-1H-indol-3-yl)acetonitrile (25). To a suspension of sodium hydride (0.65 g, 16.36 mmol, 60% in mineral oil) in DMF (30 mL) was added a solution of (1H-indol-3-yl)-acetonitrile (2.128 g, 13.64 mmol) in DMF (10 mL) in a dropwise manner. Once the evolution of gas had stopped the reaction was stirred for another 30 minutes at room temperature, followed by the dropwise addition of (3-bromopropoxy)(tert-butyl)dimethylsilane (3.17 mL, 13.64 mmol). The reaction mixture was stirred at room temperature for 2.5 hours. The reaction mixture was then poured into EtOAc (50 mL) and 1 N HCl (40 mL). The EtOAc layer was separated, washed with aqueous NaCl, dried over Na₂SO₄, filtered and concentrated under reduced pressure. The crude product was purified using flash column chromatography (SiO₂, 5% EtOAc in hexanes) to give 2-(1-(3-(tert-butyldimethylsilyloxy)propyl)-1H-indol-3-yl)acetonitrile (3.85 g, 86%) as a yellow oil.

Step 2. Synthesis of 2-(1-(3-(tert-butyldimethylsilyloxy)propyl)-1H-indol-3-yl)-3-(5,6-dihydro-4H-pyrrolo[3,2,1-ij]quinolin-1-yl)-3-oxopropanenitrile (26). To a solution of ethyl 5,6-dihydro-4H-pyrrolo[3,2,1-ij]quinoline-1-carboxylate (2.136 g, 9.32 mmol) and 2-(1-(3-(tert-butyldimethylsilyloxy)propyl)-1H-indol-3-yl)acetonitrile (3.059 g, 9.32 mmol) in THF (30 mL) which had been cooled to 0° C. was added LiHMDS (27.96 mL, 1 M in THF). The reaction mixture was warmed to room temperature and stirred for 3 hours. The mixture quenched by pouring onto EtOAc (300 mL) and 0.5 N HCl (100 mL). The EtOAc layer was separated, washed with aqueous NaCl (2×100 mL), dried over Na₂SO₄, filtered and concentrated under reduced pressure. The crude product was purified using flash column chromatography (SiO₂, 25% EtOAc in hexanes) to give 2-(1-(3-(tert-butyldimethylsilyloxy)propyl)-1H-indol-3-yl)-3-(5,6-dihydro-4H-pyrrolo[3,2,1-ij]quinolin-1-yl)-3-oxopropanenitrile (2.73 g, 57%) as a white solid.

Step 3. Synthesis of 3-(3-(5-amino-3-(5,6-dihydro-4H-pyrrolo[3,2,1-ij]quinolin-1-yl)-1H-pyrazol-4-yl)-1H-indol-1-yl)propan-1-ol (28). To a solution of 2-(1-(3-(tert-butyldimethylsilyloxy)propyl)-1H-indol-3-yl)-3-(5,6-dihydro-4H-pyrrolo[3,2,1-ij]quinolin-1-yl)-3-oxopropanenitrile (1.235 g, 2.41 mmol) in EtOH (15 ml) and AcOH (3 ml) was added hydrazine (1.2 mL). The reaction mixture was then heated at 78° C. for 3 hours. The solvent was removed under reduced pressure and the residue partitioned between dichloromethane (50 mL) and aqueous 1M NaOH (50 mL). The organic layer was separated, washed with aqueous NaCl (2×100 mL), dried over Na₂SO₄, filtered and concentrated under reduced pressure to give a mixture of 4-(1-(3-(tert-butyldimethylsilyloxy)propyl)-1H-indol-3-yl)-3-(5,6-dihydro-4H-pyrrolo[3,2,1-ij]quinolin-1-yl)-1H-pyrazol-5-amine and 3-(3-(5-amino-3-(5,6-dihydro-4H-pyrrolo[3,2,1-ij]quinolin-1-yl)-1H-pyrazol-4-yl)-1H-indol-1-yl)propan-1-ol in a 7:3 ratio (by HPLC and UV detection). The crude products were obtained as solids after drying under high vacuum pump for 16 hours.

The crude mixture of 4-(1-(3-(tert-butyldimethylsilyloxy)propyl)-1H-indol-3-yl)-3-(5,6-dihydro-4H-pyrrolo[3,2,1-ij]quinolin-1-yl)-1H-pyrazol-5-amine and 3-(3-(5-amino-3-(5,6-dihydro-4H-pyrrolo[3,2,1-ij]quinolin-1-yl)-1H-pyrazol-4-yl)-1H-indol-1-yl)propan-1-ol were dissolved in THF (10 mL) and tetrabutylammonium fluoride (2.42 mL, 1 M in THF) was added to it. The reaction mixture was stirred at room temperature for 1 h followed by addition of EtOAc (200 mL) and aqueous NaCl (150 mL). The EtOAc layer was separated, washed with aqueous NaCl (100 mL), dried over Na₂SO₄, filtered and concentrated under reduced pressure. The crude product was purified using flash column chromatography (SiO₂, 100% EtOAc followed by a gradient from 3% MeOH in dichloromethane to 5% MeOH in dichloromethane) to give 3-(3-(5-amino-3-(5,6-dihydro-4H-pyrrolo[3,2,1-ij]quinolin-1-yl)-1H-pyrazol-4-yl)-1H-indol-1-yl)propan-1-ol (0.746 g, 75% yield) as a tan solid.

General Procedure E

Synthesis of ethyl 2-(4-(((4-(5,6-dihydro-4H-pyrrolo[3,2,1-ij]quinolin-1-yl)pyrimidin-2-yl)amino)methyl)piperidine-1-carboxamido)acetate (34)

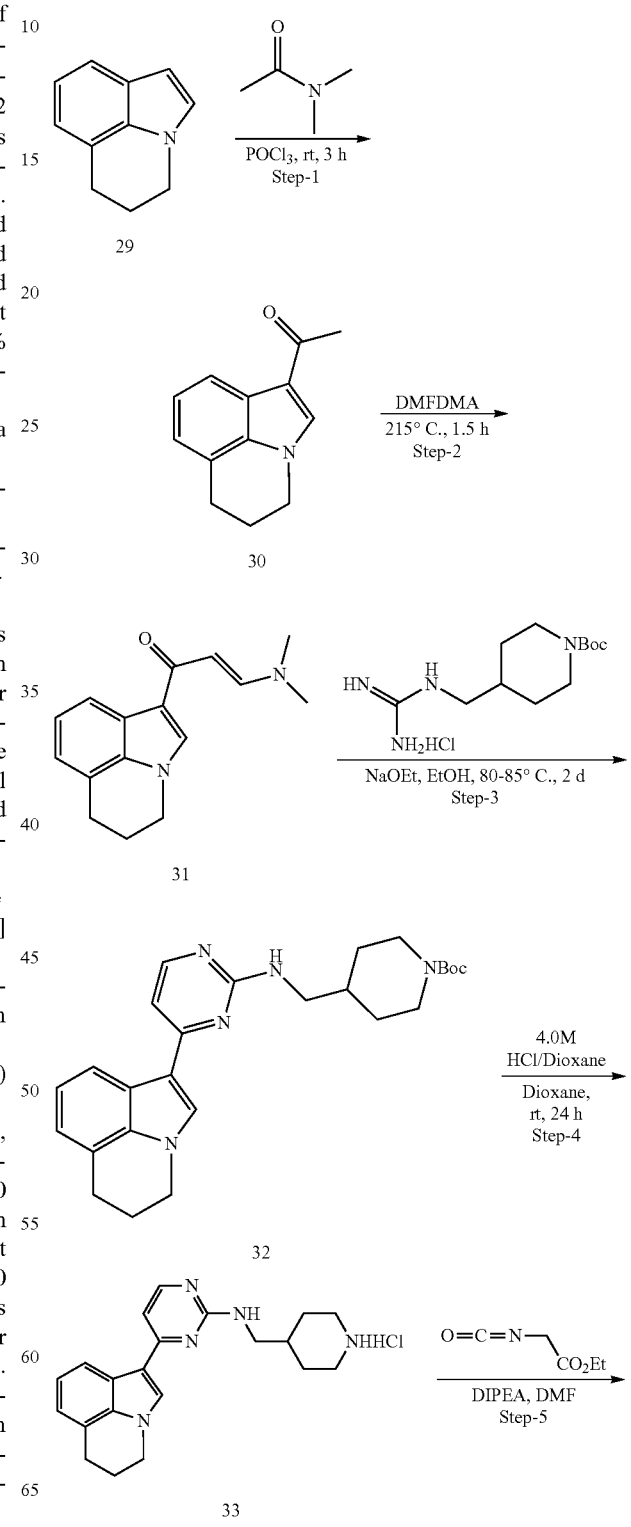

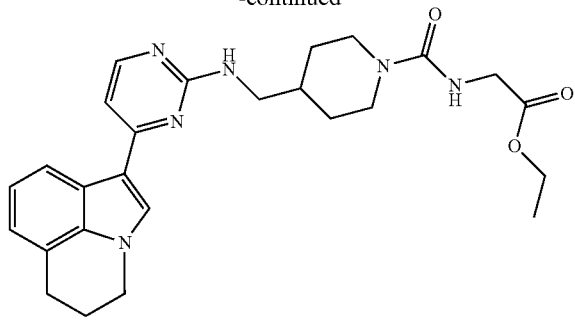

34

Step 1. Synthesis of 1-(5,6-dihydro-4H-pyrrolo[3,2,1-ij] quinolin-1-yl)ethanone (30). To a solution of N,N-dimethylacetamide (3.0 mL) in dichloroethane was added phosphorus oxychloride (5.9 mL) at room temperature. After stirring for 10 minutes, a solution of 5,6-dihydro-4H-pyrrolo[3,2,1-ij] quinoline (5.0 g, 31.85 mmol) in 1,2-dichloroethane (20 mL) was added. The reaction was stirred at room temperature for three hours. Water (250 mL) was added to the reaction mixture, and which was then basified to pH>10 using 50% aqueous NaOH solution. The organic layer was separated and the water layer was extracted with dichloromethane (200 mL). All organic layers were combined and washed with water (50 mL), brine (80 mL), dried over anhydrous sodium sulfate, and concentrated to dryness under reduced pressure. The crude product was purified by flash chromatography on silica gel eluting with Hexane/ethyl acetate (2:1) to afford 1-(5,6-dihydro-4H-pyrrolo[3,2,1-ij]quinolin-yl)ethanone as a yellow solid (4.5 g, 71%). M.p.=106-108° C.; $^1$H NMR 400 MHz (CDCl$_3$) δ 8.05 (d, J=8.0 Hz, 1H), 7.71 (s, 1H), 7.20 (t, J=7.2 Hz, 1H), 1H), 7.02 (d, J=8.0 Hz, 1H), 4.19 (t, J=6.0 Hz, 2H), 3.0 (t, J=6.4 Hz, 2H), 2.52 (s, 3H), 2.27-2.24 (m, 2H); LCMS: 201 [M+H].

Step 2. (E)-1-(5,6-dihydro-4H-pyrrolo[3,2,1-ij]quinolin-1-yl)-3-(dimethylamino)prop-2-en-1-one (31). A mixture of 1-(5,6-dihydro-4H-pyrrolo[3,2,1-ij]quinolin-yl)ethanone (0.5 g, 2.51 mmol) in N,N-dimethylformamide dimethylacetal (3 mL) was heated at 215° C. under microwave conditions for 1.5 hours. After completion, the mixture was concentrated under reduced pressure to afford (E)-1-(5,6-dihydro-4H-pyrrolo[3,2,1-ij]quinolin-1-yl)-3-(dimethylamino)prop-2-en-1-one as a yellow solid (0.63 g, 99%) that was used without further purification.

Step 3. tert-butyl 4-(((4-(5,6-dihydro-4H-pyrrolo[3,2,1-ij] quinolin-1-yl)pyrimidin-2-yl)amino)methyl)piperidine-1-carboxylate (32). To a solution of (E)-1-(5,6-dihydro-4H-pyrrolo[3,2,1-ij]quinolin-1-yl)-3-(dimethylamino)prop-2-en-1-one (5.0 g, 19.69 mmol) in anhydrous ethanol (50 mL) was added tert-butyl 4-(guanidinomethyl)piperidine-1-carboxylate hydrochloride (7.0 g, 27.29 mmol) and sodium ethoxide (10.2 mL, 27.29 mmol; 21% wt in ethanol) at room temperature. The reaction was heated at 80-85° C. for two days. The solvent was removed under reduced pressure. To the residue was added ethyl acetate (300 mL) and water (80 mL). The organic layer was separated and washed with water (60 mL), brine (80 mL), dried over anhydrous sodium sulfate and concentrated to dryness under reduced pressure. The crude product was purified by flash chromatography on silica gel eluting with ethyl acetate/hexane (3:1) to afford tert-butyl 4-(4-(5,6-dihydro-4H-pyrrolo[3,2,1-ij]quinolin-1-yl)pyrimidin-2-ylamino)methyl)piperidine-1-carboxylate as an off-white solid (6.0 g, 68%). M.p.=190-191° C.; $^1$H NMR 400 MHz (DMSO-d$_6$) δ 8.19 (d, J=7.6 Hz, 1H), 8.12 (s, 1H), 8.11 (s, 1H), 7.05 (t, J=7.2 Hz, 1H), 6.94-6.89 (m, 2H), 6.80 (s, 1H), 4.23 (t, J=5.6 Hz, 2H), 3.94 (d, J=12.8 Hz, 2H), 3.27 (t, J=6.4 Hz, 2H), 3.16 (s, 1H), 2.95 (t, J=6.0 Hz, 2H), 2.70 (t, J=11.6 Hz, 2H), 2.19-2.14 (m, 2H), 1.73 (d, J=12.4 Hz, 2H), 1.89 (s, 9H), 1.13-1.07 (m, 2H); LCMS: 448 [M+H].

Step 4. Synthesis of 4-(5,6-dihydro-4H-pyrrolo[3,2,1-ij] quinolin-1-yl)-N-(piperidin-4-ylmethyl)pyrimidin-2-amine hydrochloride (33). To a solution of tert-butyl 4-((4-(5,6-dihydro-4H-pyrrolo[3,2,1-ij]quinolin-1-yl)pyrimidin-2-ylamino)methyl)piperidine-1-carboxylate in dioxane was added 17 mL of 4.0M HCl in dioxane. The reaction was carried out at RT for 24 h. The solvent was removed under reduced pressure to afford 4-(5,6-dihydro-4H-pyrrolo[3,2,1-ij]quinolin-1-yl)-N-(piperidin-4-ylmethyl)pyrimidin-2-amine hydrochloride as a pale yellow solid (5.2 g). M.p.=192-194° C.; $^1$H NMR 400 MHz (DMSO-d$_6$) δ 9.08 (s, 1H), 8.89 (s, 1H), 8.75 (s, 1H), 8.63 (s, 1H), 8.14 (d, J=5.6 Hz, 1H), 7.26 (d, J=6.4 Hz, 1H), 7.21 (t, J=7.6 Hz, 1H), 7.06 (d, J=7.6 Hz, 1H), 4.31 (t, J=6.0 Hz, 2H), 3.56 (s, 1H), 3.52 (s, 2H), 3.28 (d, J=12.4 Hz, 2H), 2.98 (t, J=6.0 Hz, 2H), 2.85-2.78 (m, 2H), 2.19 (t, J=5.6 Hz, 2H), 1.95 (d, J=14.8 Hz, 2H), 1.56-1.52 (m, 2H); LCMS: 348 [M+H].

Step 5: Synthesis of ethyl 2-(4-((4-(5,6-dihydro-4H-pyrrolo[3,2,1-ij]quinolin-1-yl)pyrimidin-2-ylamino)methyl)piperidine-1-carboxamido)acetate (34). A solution of 4-(5,6-dihydro-4H-pyrrolo[3,2,1-ij]quinolin-1-yl)-N-(piperidin-4-ylmethyl)pyrimidin-2-amine hydrochloride (77 mg, 0.2 mmol), N,N-diisopropylethylamine (174 µL, 1.0 mmol) in N,N-dimethylformamide (2 mL) was treated with ethyl 2-isocyanatoacetate (23 mg, 0.2 mmol) and stirred at room temperature. Upon reaction completion the product was isolated by High Performance Liquid Chromatography using acetonitrile/water/trifluoroacetic acid as eluent. The pure product containing fractions were concentrated under reduced pressure to afford ethyl 2-(4-((4-(5,6-dihydro-4H-pyrrolo[3,2,1-ij]quinolin-1-yl)pyrimidin-2-ylamino)methyl)piperidine-1-carboxamido)acetate as a trifluoroacetate salt. M.p.=170-172° C.; $^1$H NMR 400 MHz (DMSO-d$_6$) δ 8.51 (s, 1H), 8.25 (m, 1H), 8.18 (m, 1H), 8.10 (d, J=6.3 Hz, 1H), 7.18 (m, 2H), 7.03 (d, J=7.0 Hz, 1H), 6.75 (s, 1H), 4.29 (m, 2H), 4.07 (q, J=7.0 Hz, 2H), 3.96 (d, J=10.3 Hz, 2H), 3.71 (s, 2H), 3.42 (s, 2H), 2.98 (t, J=5.9 Hz, 2H), 2.70 (t, J=11.7 Hz, 2H), 2.18 (m, 2H), 1.92 (m, 1H), 1.76 (d, J=10.2 Hz, 2H), 1.18 (t, J=7.0 Hz, 3H), 1.17 (m, 2H); LCMS: 477 [M+H].

General Procedure F

Synthesis of N-((1-(4-chlorophenylsulfonyl)piperidin-4-yl)methyl)-4-(5,6-dihydro-4H-pyrrolo[3,2,1-ij]quinolin-1-yl)pyrimidin-2-amine (35)

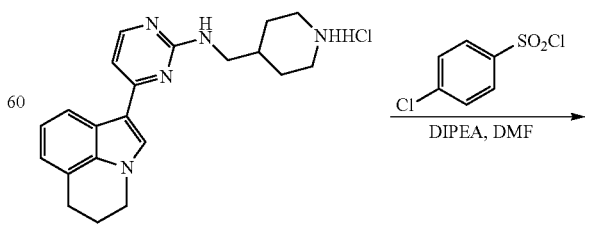

33

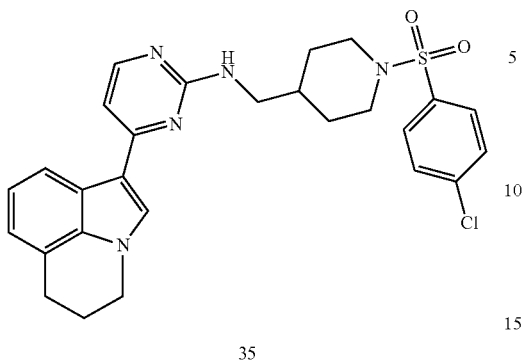

35

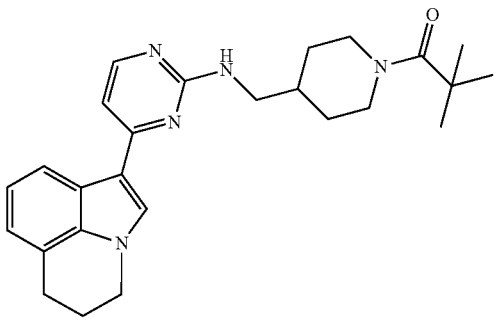

36

A solution of 4-(5,6-dihydro-4H-pyrrolo[3,2,1-ij]quinolin-1-yl)-N-(piperidin-4-ylmethyl)pyrimidin-2-amine hydrochloride (77 mg, 0.2 mmol), N,N-diisopropylethylamine (174 μL, 1.0 mmol) in N,N-dimethylformamide (2 mL) was treated with 4-chlorobenzene-1-sulfonyl chloride (23 mg, 0.2 mmol) and stirred at room temperature. Upon reaction completion the product was isolated by High Performance Liquid Chromatography using acetonitrile/water/trifluoroacetic acid as eluent. The pure product containing fractions were concentrated under reduced pressure to afford N-((1-(4-chlorophenylsulfonyl)piperidin-4-yl)methyl)-4-(5,6-dihydro-4H-pyrrolo[3,2,1-ij]quinolin-1-yl)pyrimidin-2-amine as a trifluoroacetate salt. M.p.=140-142° C.; $^1$H NMR 400 MHz (DMSO-$d_6$) δ 8.53 (s, 1H), 8.27 (s, 1H), 8.13 (s, 1H), 8.08 (d, J=6.7 Hz, 2H), 7.73 (d, J=9.0 Hz, 2H), 7.66 (d, J=8.6 Hz, 2H), 7.17 (m, 2H), 7.04 (d, J=7.0 Hz, 1H), 4.29 (m, 2H), 3.68 (d, J=12.1 Hz, 2H), 3.41 (s, 2H), 2.97 (t, J=5.9 Hz, 2H), 2.33 (t, J=11.7 Hz, 2H), 2.18 (m, 2H), 1.95 (d, J=12.9 Hz, 2H), 1.75 (m, 1H), 1.31 (m, 2H); LCMS: 522 [M+H].

General Procedure G

Synthesis of 1-(4-((4-(5,6-dihydro-4H-pyrrolo[3,2,1-ij]quinolin-1-yl)pyrimidin-2-ylamino)methyl)piperidin-1-yl)-2,2-dimethylpropan-1-one (36)

A solution of 4-(5,6-dihydro-4H-pyrrolo[3,2,1-ij]quinolin-1-yl)-N-(piperidin-4-ylmethyl)pyrimidin-2-amine hydrochloride (77 mg, 0.2 mmol), N,N-diisopropylethylamine (174 μL, 1.0 mmol) in N,N-dimethylformamide (2 mL) was treated with pivaloyl chloride (24 mg, 0.2 mmol) and stirred at room temperature. Upon reaction completion the product was isolated by High Performance Liquid Chromatography using acetonitrile/water/trifluoroacetic acid as eluent. The pure product containing fractions were concentrated under reduced pressure to afford 1-(4-((4-(5,6-dihydro-4H-pyrrolo[3,2,1-ij]quinolin-1-yl)pyrimidin-2-ylamino)methyl)piperidin-1-yl)-2,2-dimethylpropan-1-one as a trifluoroacetate salt. M.p.=170-172° C.; $^1$H NMR 400 MHz (DMSO-$d_6$) δ 8.47 (s, 1H), 8.19 (m, 1H), 8.09 (d, J=6.3 Hz, 1H), 7.98 (m, 1H), 7.15 (m, 2H), 7.03 (d, J=7.0 Hz, 1H), 4.28 (m, 4H), 2.98 (t, J=5.9 Hz, 2H), 2.78 (t, J=12.1 Hz, 2H), 2.18 (m, 2H), 1.99 (m, 1H), 1.81 (d, J=11.7 Hz, 2H), 1.19 (s, 9H), 1.14 (m, 2H); LCMS: 432 [M+H].

General Procedure H

Synthesis of 2-(5,6-dihydro-4H-pyrrolo[3,2,1-ij]quinolin-1-yl)-5-methyl-1,3,4-oxadiazole (56)

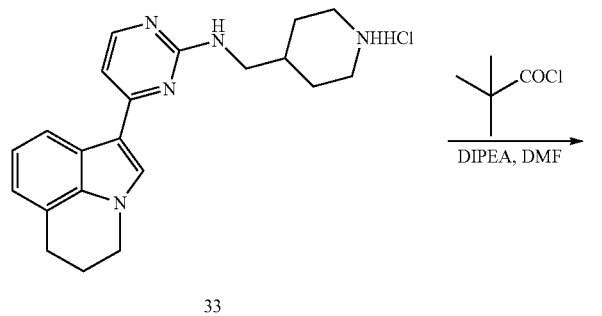

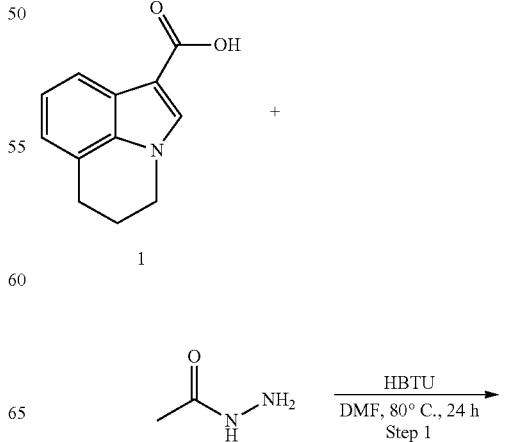

General Procedure J

Synthesis of 1-(1-(piperidin-4-yl)-1H-tetrazol-5-yl)-5,6-dihydro-4H-pyrrolo[3,2,1-ij]quinoline hydrochloride (79)

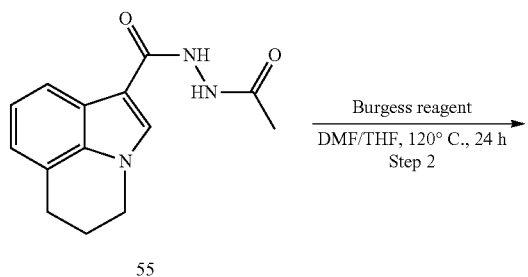

55

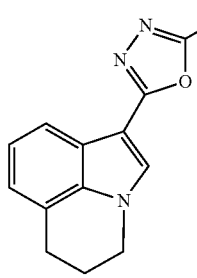

56

Step 1: To a solution of 5,6-dihydro-4H-pyrrolo[3,2,1-ij]quinoline-1-carboxylic acid (20 mg, 100 μmol) in dry N,N-dimethylformamide (700 μL) were added O-(7-azabenzotriazol-1-yl)-N,N,N',N'-tetramethyluronium hexafluorophosphate (42 mg, 110 μmol), triethylamine (21 μL, 150 μmol), and acetohydrazide (10 μmol). The reaction was heated at 80° C. for 24 hours. The solvent was removed under reduced pressure. To the residue were added 1.5 mL of mixture of butanol and 1,2-dichloroethane (1:2.5) and 1.0 mL of sat. NaHCO₃. The organic layer was separated and the solvent was removed under reduced pressure to afford N'-acetyl-5,6-dihydro-4H-pyrrolo[3,2,1-ij]quinoline-1-carbohydrazide (55). The crude was used for the next step without further purification.

Step 2: N'-acetyl-5,6-dihydro-4H-pyrrolo[3,2,1-ij]quinoline-1-carbohydrazide was dissolved in 0.8 mL of mixture of N,N-dimethylformamide/tetrahydrofuran (9:1). To the solution was added Burgess Reagent (120 mg, 500 μmol). The reaction was heated at 120° C. for 24 hours. The solvent was removed under reduced pressure. residues were purified The crude product was purified using reverse phase chromatography (HPLC, C-18) using trifluoroacetic acid as a modifier to give 2-(5,6-dihydro-4H-pyrrolo[3,2,1-ij]quinolin-1-yl)-5-methyl-1,3,4-oxadiazole (56) as a yellow solid. Mp=70-72° C.; 400 MHz $^1$HNMR (DMSO-d₆) δ 8.01 (s, 1H), 7.80 (d, J=8.4 Hz, 1H), 7.15 (t, J=7.6 Hz, 1H), 7.02 (d, J=7.2 Hz, 1H), 4.27 (t, J=5.6 Hz, 2H), 2.97 (t, J=6.0 Hz, 2H), 2.56 (s, 3H), 2.18-2.14 (m, 2H); LCMS [M+H]: 240.

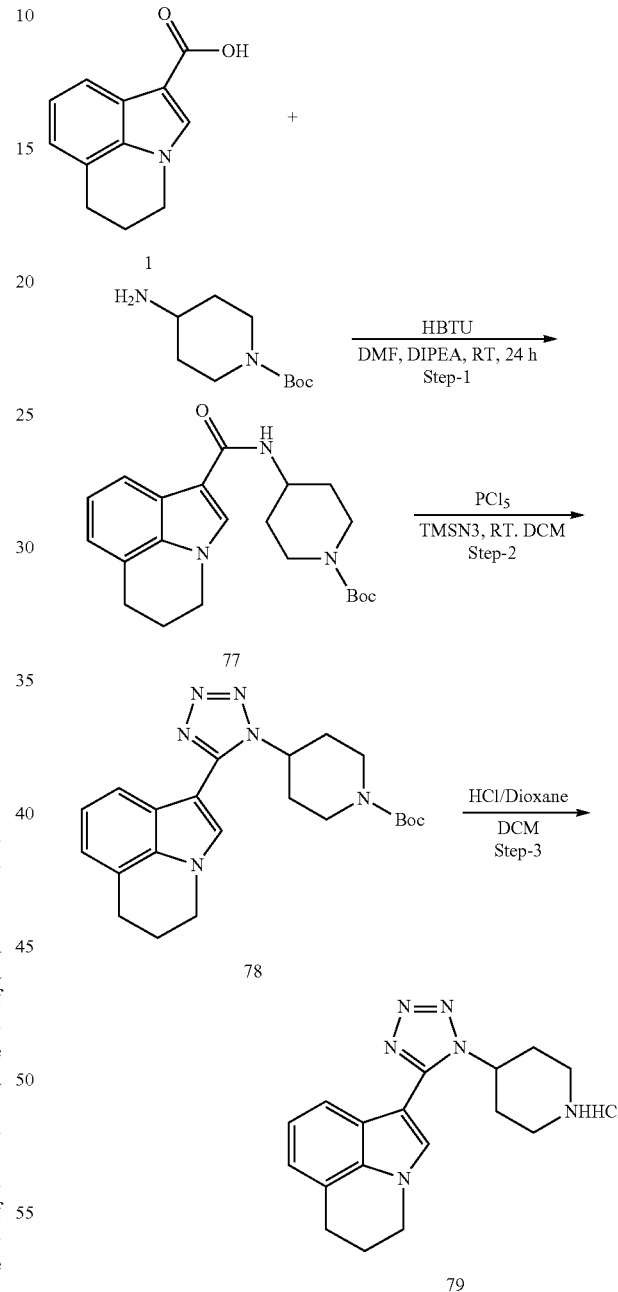

Step 1: To a solution of 5,6-dihydro-4H-pyrrolo[3,2,1-ij]quinoline-1-carboxylic acid (200 mg, 1.00 mmol) in dry N,N-dimethylformamide (3 mL) were added O-(7-azabenzotriazol-1-yl)-N,N,N',N'-tetramethyluronium hexafluorophosphate (HBTU) (417 mg, 1.10 mmol) and diisopropylethyl amine (0.35 mL, 2.0 mmol), and tert-butyl 4-aminopiperidine-1-carboxylate (1.00 mmol). The reaction was stirred at room temperature and monitored by LC-MS. Upon completion, the mixture was diluted with ethyl acetate (50 mL) and washed with water (25 mL), sat. NaHCO$_3$ solution (25 mL) and brine. The organic phase was separated and dried over sodium sulfate. After removing solvent, the crude product was purified by silica gel chromatography (EtOAc/Hexanes) to give the desired product tert-butyl 4-(5,6-dihydro-4H-pyrrolo[3,2,1-ij]quinoline-1-carboxamido)piperidine-1-carboxylate (77) as a white solid. Mp=187-189° C., LC/MS [M+H]: 384.22.

Step 2: Amide (77) (1 eq), was dissolved in dicholoromethane (15 mL/1 mmol) and phosphorus pentachloride (1 eq) was added. The mixture was stirred at ambient temperature for 2 hours then trimethylsilyl azide (8 eq) was added. Mixture was stirred at room temperature for additional 4 hours and reaction progress was followed by LC-MS. Upon completion, saturated NaHCO$_3$ solution was added and the mixture was extracted with dicholoromethane (30 mL/mol), Combined organics were combined and dried Na$_2$SO$_4$ Solvent was removed and the crude product was purified by silica gel chromatography (EtOAc/Hexanes, 25-40% gradient) to give the desired product tert-butyl 4-(5-(5,6-dihydro-4H-pyrrolo [3,2,1-ij]quinolin-1-yl)-1H-tetrazol-1-yl)piperidine-1-carboxylate (78) as a solid. LC/MS [M+H]: 409.23.

Step 3: Carbamate (78) (1 equivalent) was dissolved in dicholoromethane and HCl (20 equivalent, 4 M in dioxane) was added and stirred at room temperature for 2 to 4 hours. Concentration of the solution under reduced pressure gave the pure desired product 1-(1-(piperidin-4-yl)-1H-tetrazol-5-yl)-5,6-dihydro-4H-pyrrolo[3,2,1-ij]quinoline hydrochloride (79) as a white solid Mp=198-200° C., LC/MS [M+H]: 309.18.

3. Methods of Treatment

The present invention provides methods for the treatment of a cell proliferative disorder in a subject in need thereof by administering to a subject in need of such treatment, a therapeutically effective amount of a compound of the present invention, or a pharmaceutically acceptable salt, prodrug, metabolite, polymorph or solvate thereof. The cell proliferative disorder can be cancer or a precancerous condition. The present invention further provides the use of a compound of the present invention, or a pharmaceutically acceptable salt, prodrug, metabolite, polymorph or solvate thereof, for the preparation of a medicament useful for the treatment of a cell proliferative disorder.

The present invention also provides methods of protecting against a cell proliferative disorder in a subject in need thereof by administering a therapeutically effective amount of compound of the present invention, or a pharmaceutically acceptable salt, prodrug, metabolite, polymorph or solvate thereof, to a subject in need of such treatment. The cell proliferative disorder can be cancer or a precancerous condition. The present invention also provides the use of compound of the present invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of TO or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www-.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target kinase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention, or a pharmaceutically acceptable salt, prodrug, metabolite, polymorph or solvate thereof, demonstrates a minimum of a four fold differential, preferably a ten fold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a kinase of interest.

The present invention provides methods to assess biological activity of a compound of the present invention, or a pharmaceutically acceptable salt, prodrug, metabolite, polymorph or solvate thereof. In one method, an assay based on enzymatic activity can be utilized. In one specific enzymatic activity assay, the enzymatic activity is from a kinase. As used herein, "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular protein/peptide substrates, they all bind the same second substrate ATP in a highly conserved pocket. About 50% of the known oncogene products are protein tyrosine kinases (PTKs), and their kinase activity has been shown to lead to cell transformation. Preferably, the kinase assayed is a tyrosine kinase.

A change in enzymatic activity caused by a compound of the present invention, or a pharmaceutically acceptable salt, prodrug, metabolite, polymorph or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, adaptor proteins such as Gab-1, Grb-2, Shc, SHP2 and c-Cbl, and signal transducers such as Ras, Src, PI3K, PLC-γ, STATs, ERK1 and 2 and FAK.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor, a HER2 inhibitor, a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard;

Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin, eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680

(targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

4. Pharmaceutical Compositions

The present invention also provides pharmaceutical compositions comprising a compound of formula I, II, IIa, III, IIIa, IIIb, IV or V in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same.

"Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

5. Examples

Example 1

Synthesis of 5-(5,6-dihydro-4H-pyrrolo[3,2,1-ij]quinolin-1-yl)-4-(3-methoxyphenyl)-1H-pyrazol-3(2H)-one (5)

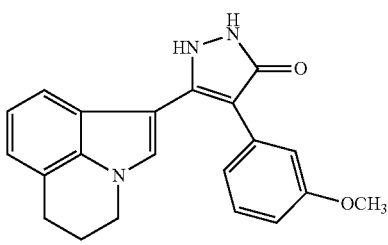

5-(5,6-dihydro-4H-pyrrolo[3,2,1-ij]quinolin-1-yl)-4-(3-methoxyphenyl)-1H-pyrazol-3(2H)-one was synthesized as outlined in General Procedure A using (3-methoxy-phenyl)-acetic acid methyl ester. The crude product was purified using reverse phase chromatography (HPLC, C-18) and trifluoroacetic acid as a modifier to give the desired product as an off-white solid (0.241 g, 39%). M.p.=126-129° C.; 400 MHz $^1$H NMR (CDCl$_3$) δ: 7.48 (s, 1H), 7.12-7.04 (m, 1H), 6.96-6.9 (m, 2H), 6.88-6.76 (m, 3H), 6.68-6.63 (m, 1H), 4.2 (t, J=6 Hz, 2H), 2.94 (t, J=6 Hz, 2H), 2.2-2.1 (m, 2H); LCMS [M+H]: 346.4.

Example 2

Synthesis of 2-(5,6-dihydro-4H-pyrrolo[3,2,1-ij]quinolin-1-yl)-5-phenyl-1,3,4-oxadiazole (57)

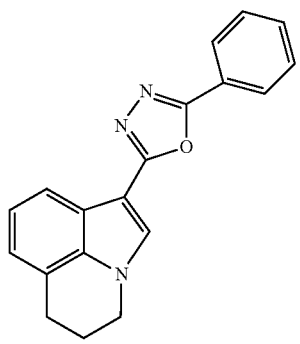

2-(5,6-dihydro-4H-pyrrolo[3,2,1-ij]quinolin-1-yl)-5-phenyl-1,3,4-oxadiazole was synthesized as outlined in General Procedure J using 5,6-dihydro-4H-pyrrolo[3,2,1-ij]quinoline-1-carboxylic acid and benzohydrazide. The crude product was purified using reverse phase chromatography (HPLC, C-18) using trifluoroacetic acid as a modifier to give the desired product 2-(5,6-dihydro-4H-pyrrolo[3,2,1-ij]quinolin-1-yl)-5-phenyl-1,3,4-oxadiazole as a yellow solid. Mp=155-157° C.; 400 MHz $^1$HNMR (DMSO-d$_6$) δ 8.31 (s, 1H), 8.13-8.10 (m, 2H), 7.90 (d, J=8.0 Hz, 1H), 7.65-7.63 (m, 3H), 7.21 (t, J=6.8 Hz, 1H), 7.06 (d, J=7.6 Hz, 1H), 4.31 (t, J=5.6 Hz, 2H), 2.99 (t, J=6.0 Hz, 2H), 2.21-2.18 (m, 2H); LCMS [M+H]: 302.

Example 3

Synthesis of Heterocyclic Compounds

The compounds described in Table 2 were synthesized by using corresponding acid chlorides as described in general procedure C.

TABLE 2

| Compound No. | Structure | [M + H] |
|---|---|---|
| 10 | 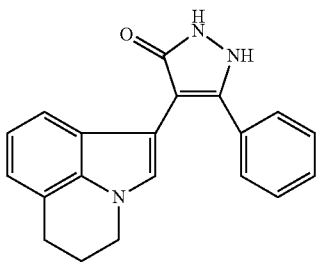 [SMILES: O=c1[nH][nH]c(-c2ccccc2)c1-c1cn2c3c(cccc13)CCC2] | 316 |
| 11 | 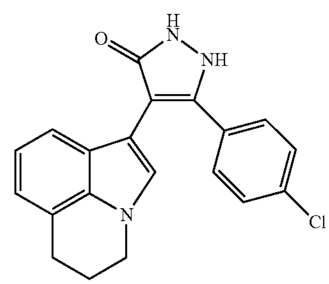 [SMILES: O=c1[nH][nH]c(-c2ccc(Cl)cc2)c1-c1cn2c3c(cccc13)CCC2] | 350 |
| 12 | 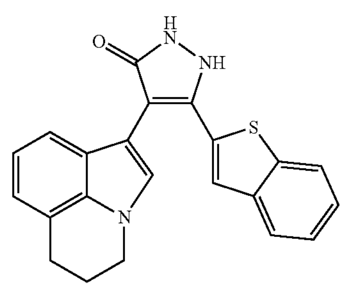 [SMILES: O=c1[nH][nH]c(-c2cc3ccccc3s2)c1-c1cn2c3c(cccc13)CCC2] | 372 |
| 13 | 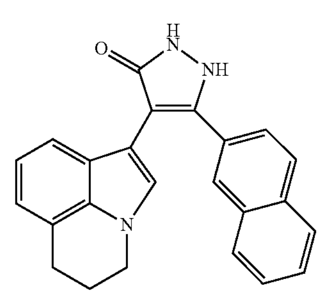 [SMILES: O=c1[nH][nH]c(-c2ccc3ccccc3c2)c1-c1cn2c3c(cccc13)CCC2] | 366 |

TABLE 2-continued
| Compound No. | Structure | [M + H] |
|---|---|---|
| 14 | 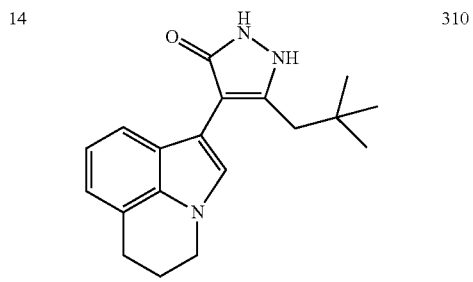 | 310 |
| 15 | 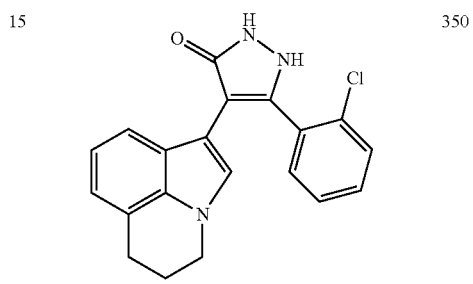 | 350 |
| 16 | 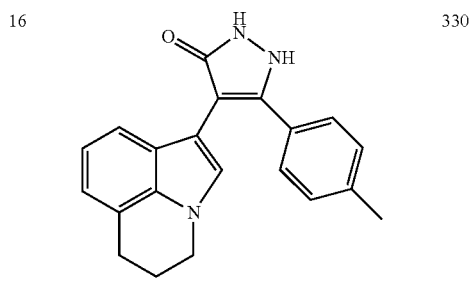 | 330 |
| 17 | 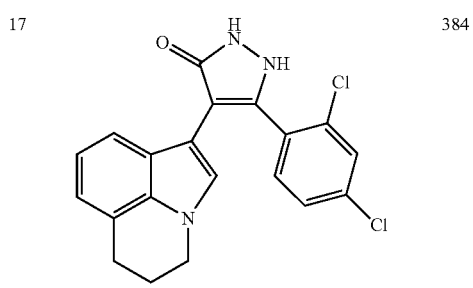 | 384 |
TABLE 2-continued
| Compound No. | Structure | [M + H] |
|---|---|---|
| 18 | 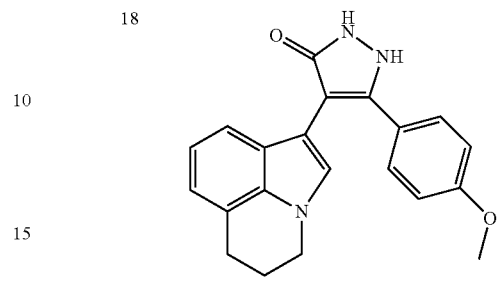 | 346 |
| 19 | 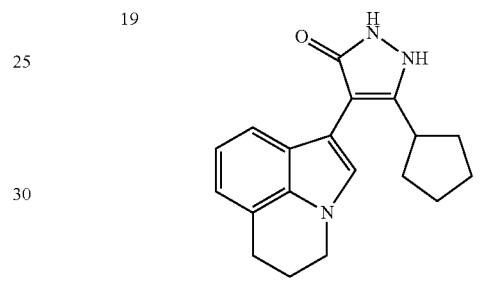 | 308 |
| 20 | 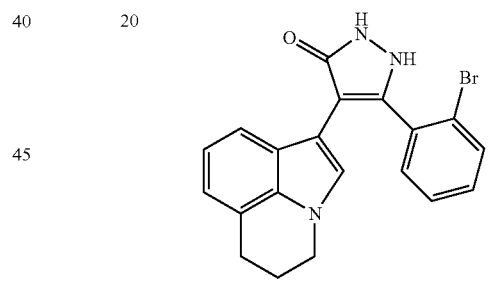 | 394 |
| 21 | 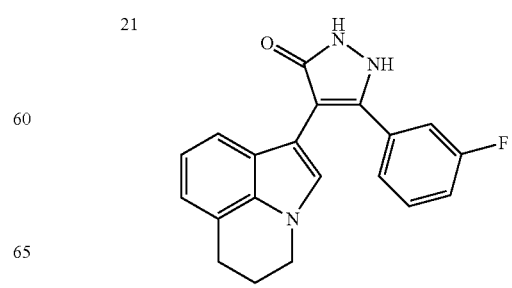 | 334 |

TABLE 2-continued

| Compound No. | Structure | [M + H] |
|---|---|---|
| 22 | 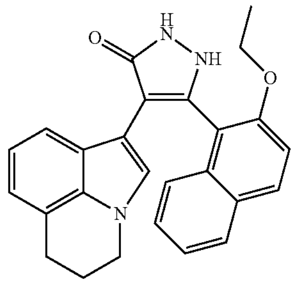 [SMILES: CCOc1ccc2ccccc2c1-c1[nH][nH]c(=O)c1-c1cn2c3c(cccc13)CCC2] | 410 |
| 23 | 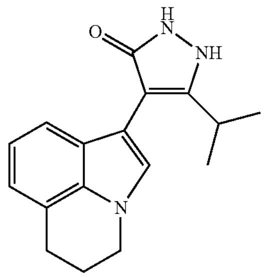 [SMILES: CC(C)c1[nH][nH]c(=O)c1-c1cn2c3c(cccc13)CCC2] | 282 |

Compound 28 in Table 3 was synthesized using general procedure D.

TABLE 3

| Compound No. | Structure | [M + H] |
|---|---|---|
| 28 | 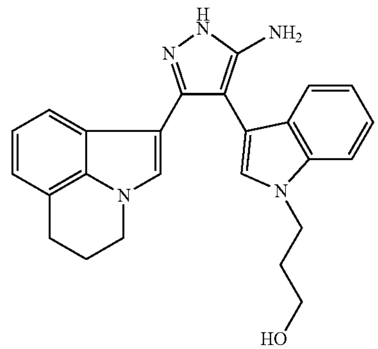 [SMILES: Nc1[nH]nc(-c2cn3c4c(cccc24)CCC3)c1-c1cn(CCCO)c2ccccc12] | 412 |

The following compounds described in Table 4 were synthesized using general procedure E, F and G with corresponding isocyanates for general procedure E, sulfonyl chloride for general procedure F and acid chloride for general procedure G.

TABLE 4

| Compound No. | Structure | [M + H] | Procedure |
|---|---|---|---|
| 33 | 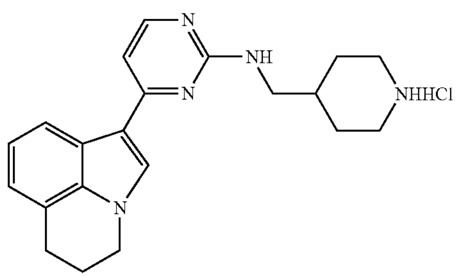 | 384 | E |
| 34 | 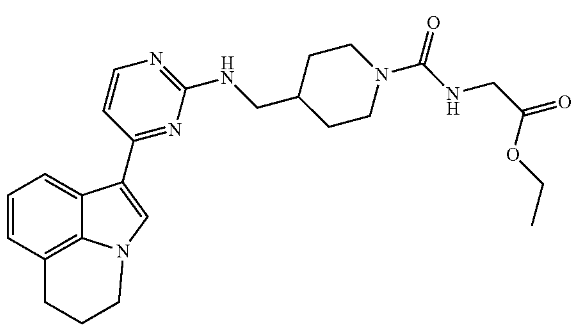 [SMILES: CCOC(=O)CNC(=O)N1CCC(CNc2nccc(-c3cn4c5c(cccc35)CCC4)n2)CC1] | 477 | E |

TABLE 4-continued

| Compound No. | Structure | [M + H] | Procedure |
|---|---|---|---|
| 35 | 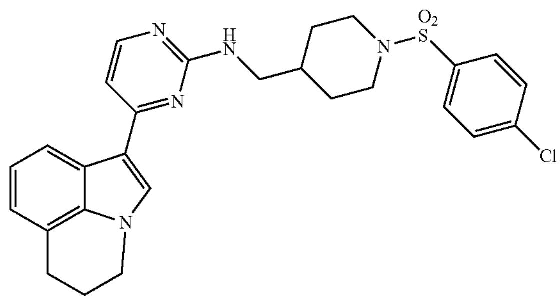 [SMILES: O=S(=O)(c1ccc(Cl)cc1)N1CCC(CNc2nccc(-c3cn4c5c(cccc35)CCC4)n2)CC1] | 522 | F |
| 36 | 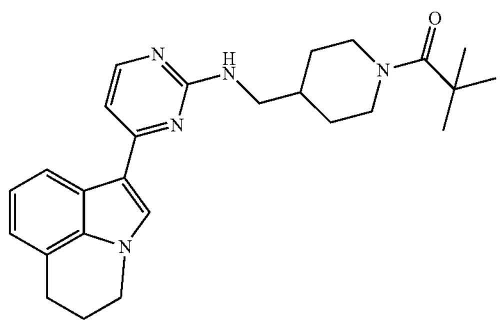 [SMILES: CC(C)(C)C(=O)N1CCC(CNc2nccc(-c3cn4c5c(cccc35)CCC4)n2)CC1] | 432 | G |
| 37 | 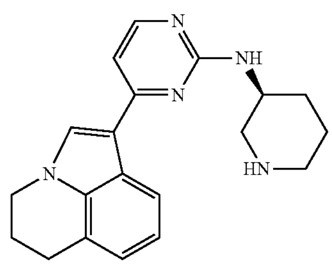 [SMILES: c1cc2c3c(c1)c(-c1ccnc(N[C@H]4CCCNC4)n1)cn3CCC2] | 334 | E |
| 38 | 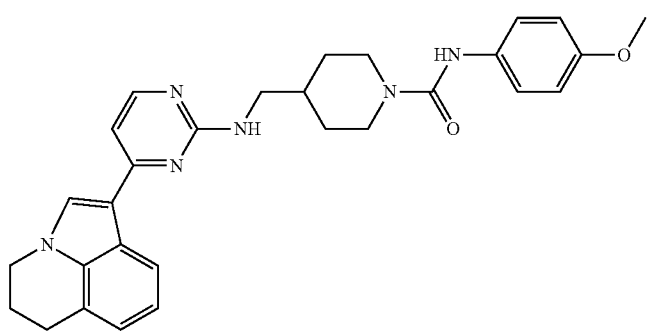 [SMILES: COc1ccc(NC(=O)N2CCC(CNc3nccc(-c4cn5c6c(cccc46)CCC5)n3)CC2)cc1] | 497 | E |
| 39 | 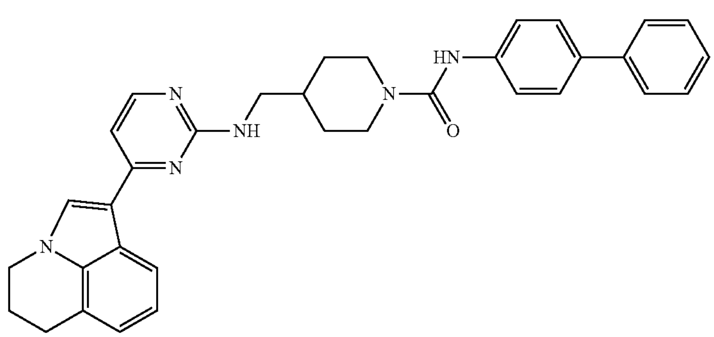 [SMILES: O=C(Nc1ccc(-c2ccccc2)cc1)N1CCC(CNc2nccc(-c3cn4c5c(cccc35)CCC4)n2)CC1] | 543 | E |

TABLE 4-continued
| Compound No. | Structure | [M + H] | Procedure |
|---|---|---|---|
| 40 | 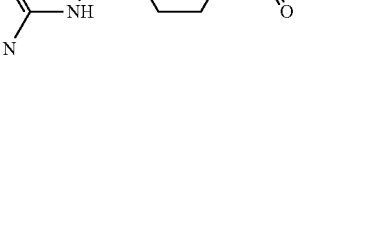 | 539 | E |
| 41 | 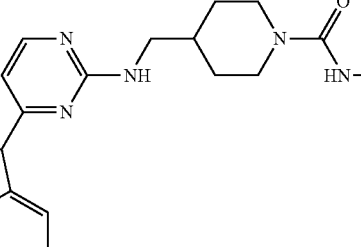 | 463 | E |
| 42 | 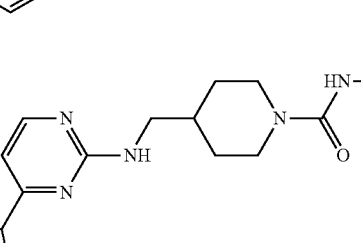 | 426 | E |
| 43 | 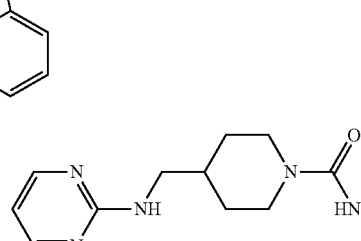 | 433 | E |
| 44 | 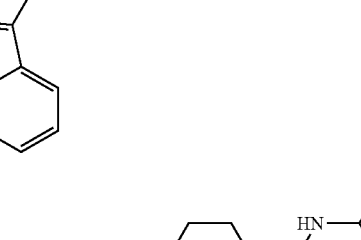 | 501 | E |

TABLE 4-continued

| Compound No. | Structure | [M + H] | Procedure |
|---|---|---|---|
| 45 | 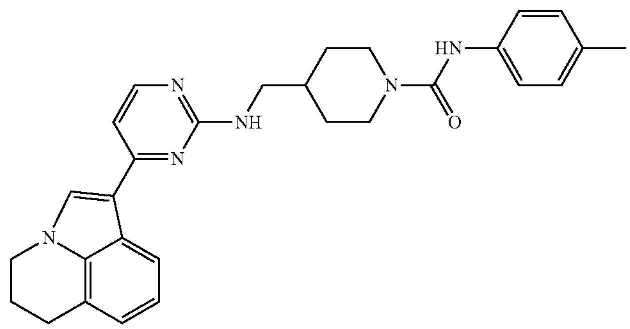 [SMILES: Cc1ccc(NC(=O)N2CCC(CNc3nccc(-c4cn5c6c(cccc46)CCC5)n3)CC2)cc1] | 481 | E |
| 46 | 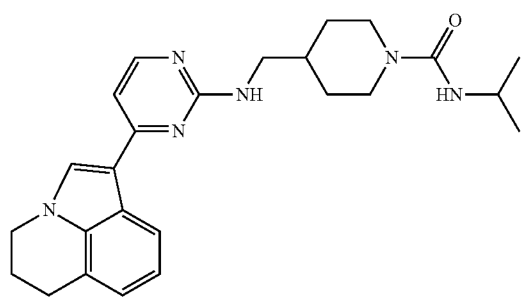 [SMILES: CC(C)NC(=O)N1CCC(CNc2nccc(-c3cn4c5c(cccc35)CCC4)n2)CC1] | 433 | E |
| 47 | 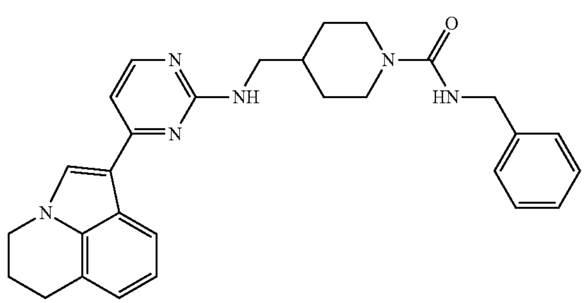 [SMILES: O=C(NCc1ccccc1)N1CCC(CNc2nccc(-c3cn4c5c(cccc35)CCC4)n2)CC1] | 481 | E |
| 48 | 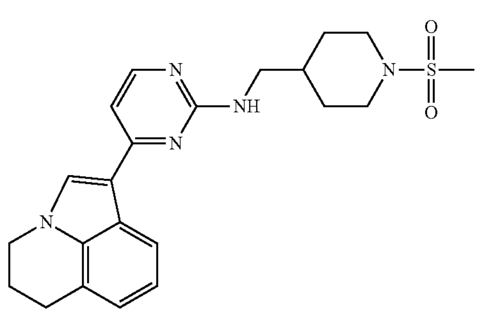 [SMILES: CS(=O)(=O)N1CCC(CNc2nccc(-c3cn4c5c(cccc35)CCC4)n2)CC1] | 467 | F |

TABLE 4-continued

| Compound No. | Structure | [M + H] | Procedure |
|---|---|---|---|
| 49 | 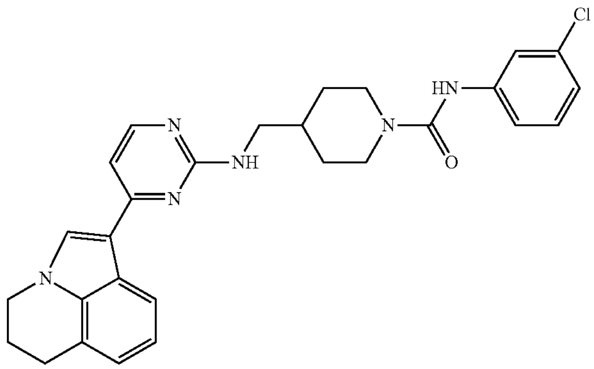 [SMILES: O=C(Nc1cccc(Cl)c1)N1CCC(CNc2nccc(-c3cn4c5c(cccc35)CCC4)n2)CC1] | 501 | E |
| 50 | 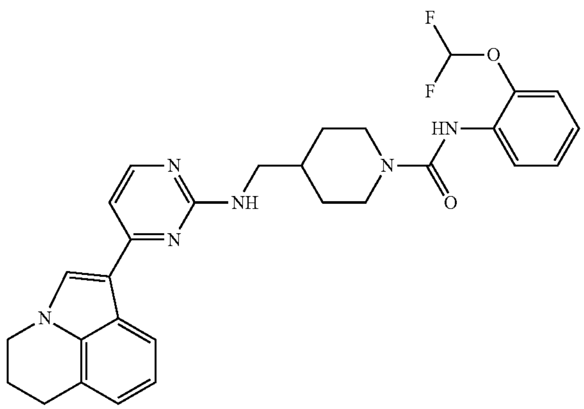 [SMILES: O=C(Nc1ccccc1OC(F)F)N1CCC(CNc2nccc(-c3cn4c5c(cccc35)CCC4)n2)CC1] | 533 | E |
| 51 | 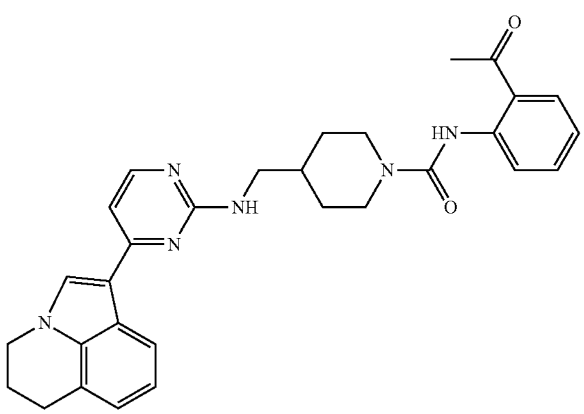 [SMILES: CC(=O)c1ccccc1NC(=O)N1CCC(CNc2nccc(-c3cn4c5c(cccc35)CCC4)n2)CC1] | 509 | E |
| 52 | 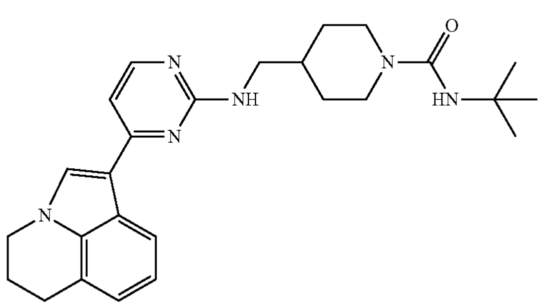 [SMILES: CC(C)(C)NC(=O)N1CCC(CNc2nccc(-c3cn4c5c(cccc35)CCC4)n2)CC1] | 447 | E |

TABLE 4-continued
| Compound No. | Structure | [M + H] | Procedure |
|---|---|---|---|
| 53 | 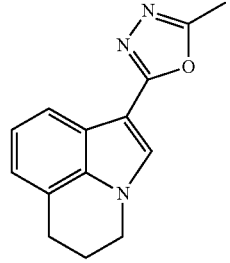 | 527 | E |
| 54 | 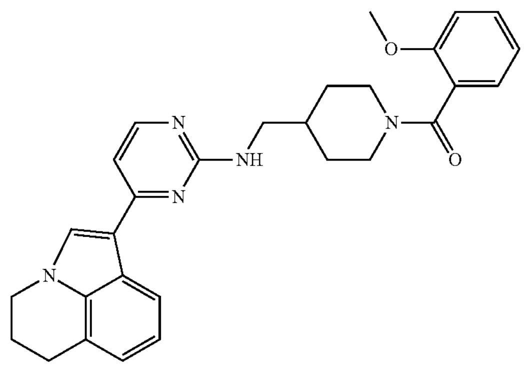 [SMILES: COc1ccccc1C(=O)N1CCC(CNc2nccc(-c3cn4c5c(cccc35)CCC4)n2)CC1] | 482 | G |
The following compounds described in Table 5 were made using general procedure H using corresponding acetohydrazides.
TABLE 5
| Compound No. | Structure | [M + H] |
|---|---|---|
| 56 | 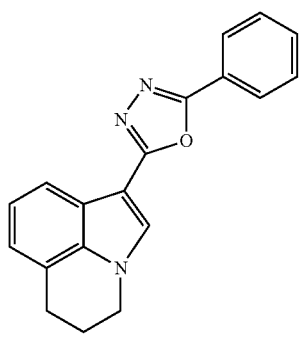 | 240 |
| 57 | 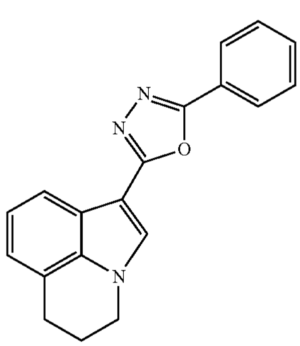 [SMILES: c1ccc(-c2nnc(-c3cn4c5c(cccc35)CCC4)o2)cc1] | 302 |
| 58 | | 338 |
| 59 | | 320 |

TABLE 5-continued

| Compound No. | Structure | [M + H] |
|---|---|---|
| 60 | 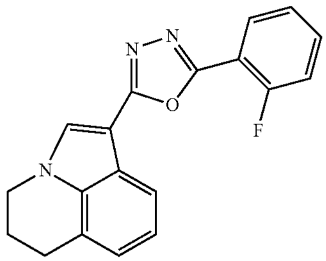 [SMILES: Fc1ccccc1-c1nnc(-c2cn3c4c(cccc24)CCC3)o1] | 320 |
| 61 | 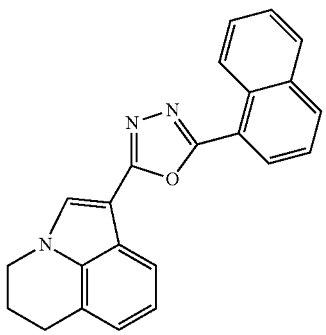 [SMILES: c1ccc2c(-c3nnc(-c4cn5c6c(cccc46)CCC5)o3)cccc2c1] | 352 |
| 62 | 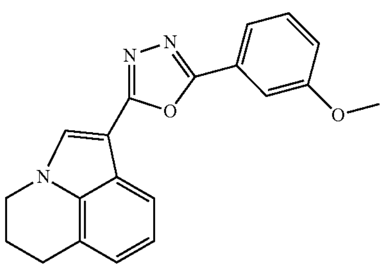 [SMILES: COc1cccc(-c2nnc(-c3cn4c5c(cccc35)CCC4)o2)c1] | 332 |
| 63 | 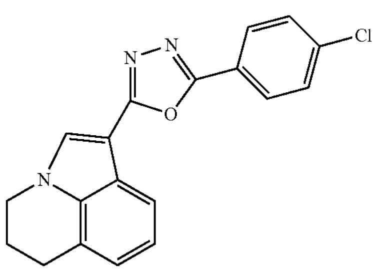 [SMILES: Clc1ccc(-c2nnc(-c3cn4c5c(cccc35)CCC4)o2)cc1] | 336 |
| 64 | 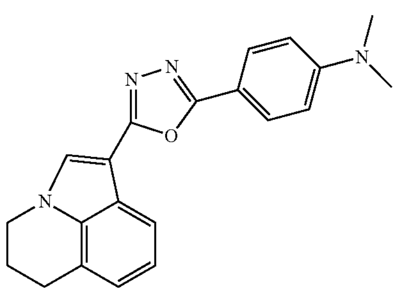 [SMILES: CN(C)c1ccc(-c2nnc(-c3cn4c5c(cccc35)CCC4)o2)cc1] | 345 |
| 65 | | 336 |
| 66 | | 380 |
| 67 | | 380 |
| 68 | | 316 |
| 69 | | 346 |

TABLE 5-continued
| Compound No. | Structure | [M + H] |
|---|---|---|
| 70 | 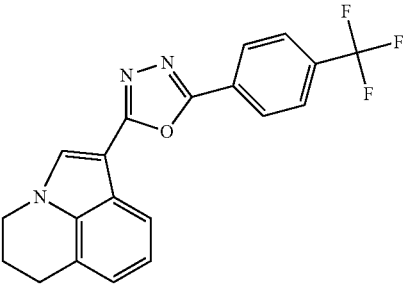 [SMILES: FC(F)(F)c1ccc(-c2nnc(-c3cn4c5c(cccc35)CCC4)o2)cc1] | 370 |
| 71 | 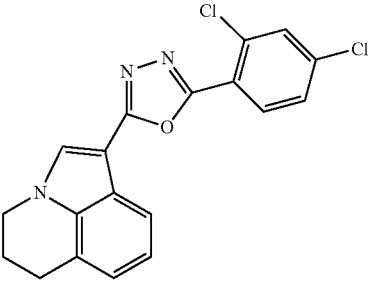 [SMILES: Clc1ccc(-c2nnc(-c3cn4c5c(cccc35)CCC4)o2)c(Cl)c1] | 370 |
| 72 | 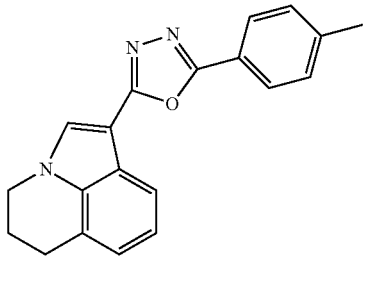 [SMILES: Cc1ccc(-c2nnc(-c3cn4c5c(cccc35)CCC4)o2)cc1] | 316 |
| 73 | 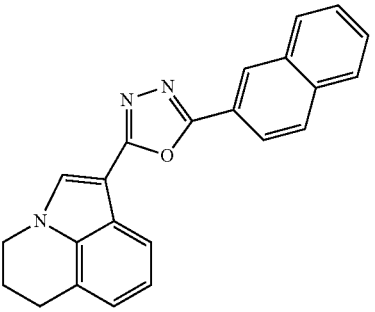 [SMILES: c1ccc2cc(-c3nnc(-c4cn5c6c(cccc46)CCC5)o3)ccc2c1] | 352 |
| 74 | 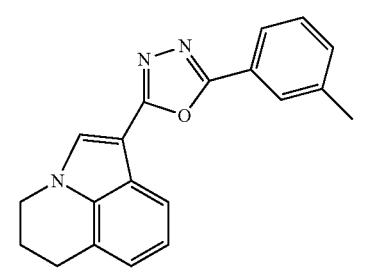 [SMILES: Cc1cccc(-c2nnc(-c3cn4c5c(cccc35)CCC4)o2)c1] | 316 |
TABLE 5-continued
| Compound No. | Structure | [M + H] |
|---|---|---|
| 75 | 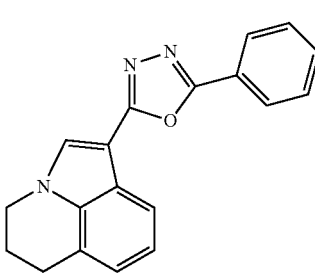 | 330 |
| 76 | 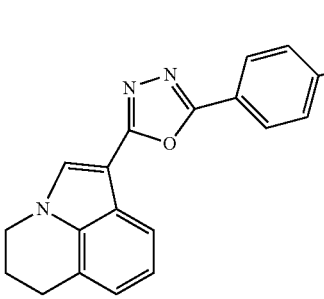 | 358 |
The following compounds described in Table 6 were synthesized by using general procedure J and corresponding amines.
TABLE 6
| Compound No. | Structure | [M + H] |
|---|---|---|
| 79 | 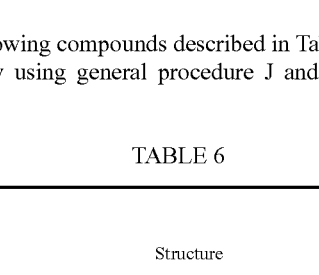 | 309 |
| 80 | 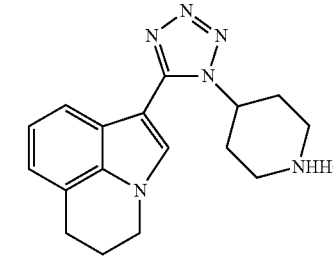 | 295 |

TABLE 6-continued

| Compound No. | Structure | [M + H] |
|---|---|---|
| 81 | 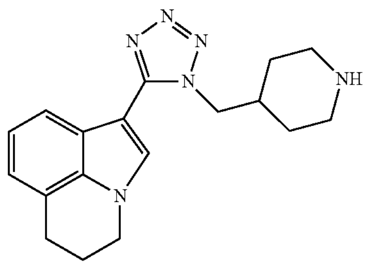 [SMILES: c1cc2c3c(c1)c(-c1nnnn1CC1CCNCC1)cn3CCC2] | 323 |
| 82 | 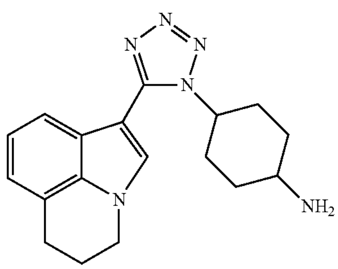 [SMILES: NC1CCC(n2nnnc2-c2cn3c4c(cccc24)CCC3)CC1] | 323 |
| 83 | 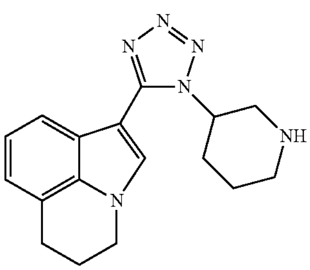 [SMILES: c1cc2c3c(c1)c(-c1nnnn1C1CCCNC1)cn3CCC2] | 309 |

Example 4

Abl Kinase Activity Assay

The disclosed compounds were assayed for their ability to inhibit the activity of ABL kinase. Nunc Maxisorb plates are coated with streptavidin by overnight incubation with 100 μL per well of 1 μg/mL streptavidin in DPBS. Prior to the start of the experiment, the plates are washed with TBST (3×200 μL) and blocked for at least 3 hours by adding 150 μL of 5% BSA/TBST. The plates are washed with TBST (3×200 μL/well) and left dry immediately before the capture step.

The test articles and controls (Gleevec) are prepared using the following assay buffer @ 10× desired final concentration (50 mM Tris pH 7.0, 0.02 mg/ml BSA, 10 mM MgCl$_2$, 0.1 mM Na$_3$VO$_4$, 1 mM EGTA, 0.01% NP-40, 1 mM DTT in 10% glycerol/water). In a reaction plate are added rapidly 5 μL test article (or control) and 30 μL ABL or ABL T315I (0.089 nM final concentration, in the above buffer). The plate is incubated for 20 minutes. To the reaction plate is added ATP (100 μM final concentration) and AblTide (128 nM final concentration) in a volume of 15 μL. The plate is incubated at room temperature for one hour.

From the reaction plate, 40 μL is transferred to the streptavidin coated plate. The capture plate is incubated at room temperature for 30 minutes then washed 3× with TBST. To the capture plate is added 100 μL/well of Cell Signaling anti-phospho tyrosine at a dilution of 1:3000 in 2% BSA/TBST. The plate is incubated for two hours at room temperature then washed 3× with TBST. To the capture plate is added 100 μL/well of Alkaline Phosphatase Tagged Goat anti Mouse Antibody at a dilution of 1:4000 in 2% BSA/TBST. The plate is incubated for one hour at room temperature then washed 3× with TBST.

The fluorescent readout was initiated by the addition of 100 μL/well of Attophos reagent (6 mg/10 mL). The reading was done on the Perkin Elmer Envision system.

Table 7 shows the ABL kinase inhibition activity of selected compounds.

Example 5

FGFR2 Kinase Activity Assay

The enzymatic assays described herein are conducted according to the following procedures from commercially available reagents. In one, non limiting, example, a fluorescent ELISA assay is used to identify and characterize inhibitors of FGFR2 kinase as described herein. This heterogeneous assay utilizes a biotinylated peptide with a tyrosine motif as a substrate and an anti-phospho-tyrosine antibody to measure phosphorylation of the substrate. The reaction is initiated by adding the test compound, 37 μM Pyk2 substrate (Midwest Biotech, Cat. # MBT2383), 12.5 μM ATP (Roche, Cat. #11 140 965 001) and 0.5 μM FGFR2 enzyme (Millipore, Cat. #14-742) sequentially to a non-binding polypropylene V-well plate. All reagents are in an assay buffer consisting of: 50 mM Tris-HCL, 0.02 mg/ml BSA, 10 mM MgCl$_2$, 0.1 mM Na$_3$VO$_4$, 1 mM EGTA, 75 μM ATP, 0.01% NP-40, 2 mM DTT and 10% glycerol. The reaction is incubated for 60 minutes. As the reaction proceeds, FGFR2 phosphorylates tyrosines in the peptide. The reaction mixture is then moved to a blocked streptavidin-coated Nunc Maxisorb plate (coated with 100 ng streptavidin from Pierce (Cat. #15-124) per well), allowing for the capture of the biotinylated peptide. Peptides are captured for 30 minutes at room temperature, the phosphorylation of peptides continues during this phase. The reaction is stopped by washing the streptavidin-coated plate 6 times with TBST. Phosphorylated peptide is detected by adding anti-phospho-tyrosine antibody (Cell Signaling, Cat. #9411, diluted 1:3000) to the streptavidin-coated plate. Unbound anti-phospho-tyrosine antibody is removed by washing the streptavidin-coated plate 6 times with TBST. Secondary detection is performed using alkaline phosphatase tagged goat anti-mouse antibody (Pierce, Cat. #31320, diluted 1:4000) for one hour. Unbound secondary antibody is removed by washing the streptavidin-coated plate 6 times with TBST. The fluorescent readout is initiated by adding to the streptavidin-coated plate Promega Attophos substrate (Promega, Cat. # S1000, dilution=6 mg/10 ml), which, when dephosphorylated by alkaline phosphatase, emits a fluorescent signal of 595 nm in wavelength when excited by a signal of 400 nm in wavelength. The reading of the 595 nm signal is done on the Perkin Elmer Envision system. Compounds which prevent FGFR2 from phosphorylating the peptide result in a lower fluorescent signal. The 595 nm fluorescent signal is directly proportional to the activity of FGFR2. Thus, the inhibition of FGFR2 by compounds is monitored by the decrease in the 595 nm fluorescent signal. Biological activity of selected compounds is shown in Table 7.

TABLE 7

| Compound No. | Abl (T315I) inhibition @ 10 μM (%) | FGFR2 (N549H) inhibition @ 30 μM (%) |
|---|---|---|
| 4 | 63 | 96 |
| 10 | 25 | NA |
| 11 | 13 | NA |
| 12 | 53 | NA |
| 13 | 37 | 94 |
| 14 | 8 | NA |
| 15 | 20 | 33 |
| 16 | 83 | NA |
| 17 | 81 | 48 |
| 18 | 9 | NA |
| 19 | 77 | NA |
| 20 | 87 | 45 |
| 21 | 79 | 75 |
| 22 | 11 | 41 |
| 23 | 8 | NA |
| 34 | NA | 60 |
| 37 | NA | 102 |
| 38 | NA | 79 |
| 39 | NA | 71 |
| 40 | NA | 68 |
| 41 | NA | 68 |
| 42 | NA | 66 |
| 43 | NA | 65 |
| 44 | NA | 65 |
| 45 | NA | 64 |
| 46 | NA | 61 |
| 47 | NA | 60 |
| 48 | NA | 59 |
| 49 | NA | 58 |
| 50 | NA | 55 |
| 51 | NA | 52 |
| 52 | NA | 51 |
| 53 | NA | 48 |
| 54 | NA | 46 |
| 81 | NA | 91 |
| 82 | NA | 91 |
| 83 | NA | 84 |

TABLE 8

| Compound No | MTS, MDA-MB-231, 72 h, 10 μM (% Inhibition) | MTS, DLD-1, 72 h, 10 μM (% Inhibition) |
|---|---|---|
| 10 | 37 | 46 |
| 11 | 97 | 97 |
| 12 | 90 | 87 |
| 13 | 46 | 61 |
| 14 | 72 | 57 |
| 16 | 63 | 78 |
| 17 | NA | 40 |
| 18 | 59 | 72 |
| 34 | NA | 65 |
| 35 | 98 | 97 |
| 36 | NA | 85 |
| 37 | 83 | 83 |
| 38 | 98 | 97 |
| 39 | 31 | 52 |
| 40 | 99 | 98 |
| 41 | 33 | NA |
| 42 | 79 | 97 |
| 43 | 43 | 86 |
| 44 | 84 | 97 |
| 45 | 72 | 94 |
| 46 | NA | 52 |
| 47 | 97 | 98 |
| 49 | 85 | 96 |
| 50 | 53 | 55 |
| 51 | 72 | 97 |
| 52 | NA | 55 |
| 53 | 95 | 98 |
| 54 | 37 | 95 |
| 56 | 77 | 94 |
| 63 | 100 | 98 |

Example 6

MTS Assay

Cells were maintained at 37° C., 5% $CO_2$ in RPMI media supplemented with 1% fetal bovine serum, penicillin/streptomycin and fungizone (Invitrogen). Cells were seeded into 96-well tissue culture plates at 3000 per well and cultured at 37° C. for 18 h. Test compounds were dissolved and diluted to 300× in DMSO then diluted 1:40 in DMEM. Cells were incubated with test compounds for 72 hours followed by incubation with tetrazolium compound (3-(4,5-dimethylthiazol-2-yl)-5-(3-carboxymethoxyphenyl)-2-(4-sulfophenyl)-2H-tetrazolium, inner salt; MTS) and the electron coupling reagent, phenazine methosulfate (PMS) for 4 hours. MTS was chemically reduced by dehydrogenase in cells into formazan. The ability of compounds to inhibit cell growth in this assay is correlated with the reduction of dehydrogenase enzyme activity found in metabolically active cells. The measurement of the absorbance of the formazan was assessed using an ENVISION™ (Perkin Elmer) microplate reader at 492 nm. The calculated $IC_{50}$ value is the concentration of the test compound that causes a 50% decrease in the absorbance. Compounds of the present invention inhibit the growth of a variety of cancer cells. The data for certain compounds of the invention are shown in Table 8.

What is claimed is:

1. A compound of Formula I or a pharmaceutically acceptable salt, prodrug, or derivative thereof:

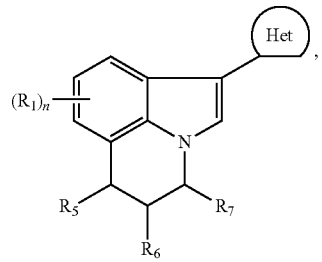

(I)

wherein:

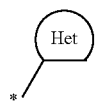

is an optionally substituted heteroaryl or heterocycle selected from:

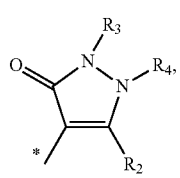 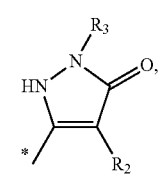 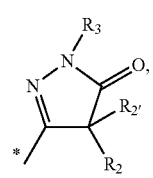

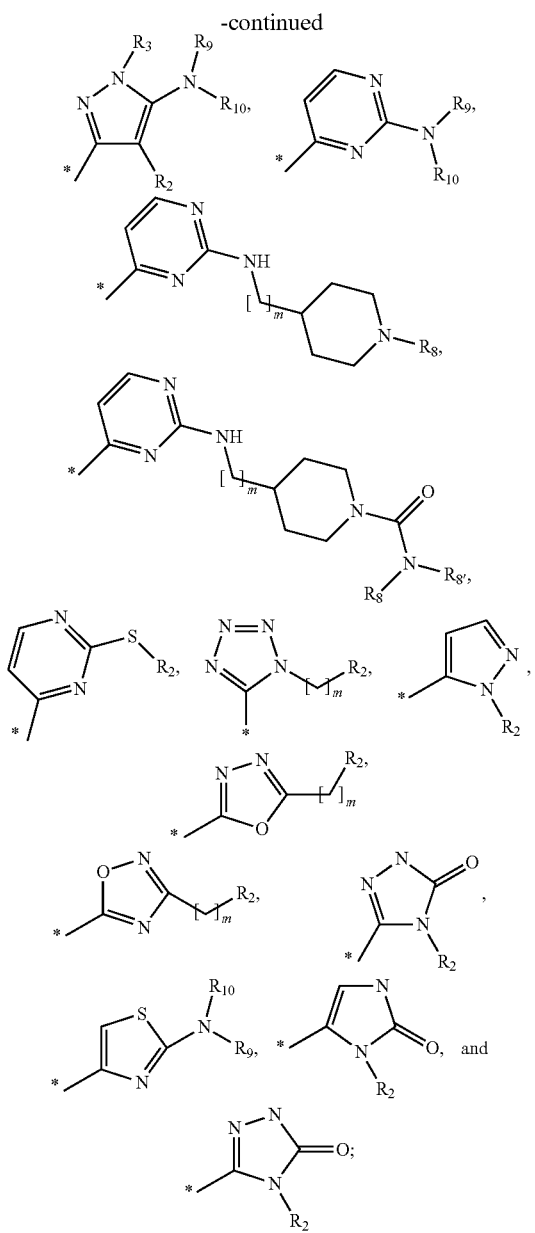

wherein "*" indicates the point of attachment of the optionally substituted heteroaryl or heterocycle;

n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ and $R_{2'}$ are each independently H, unsubstituted or substituted $C_1$-$C_9$ alkyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2,5- or 6-member rings and 1-4 heteroatoms selected from N, O and S, and optionally containing unsaturation, or -$T_r$-$R_r$;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2,5- or 6-member rings and 1-4 heteroatoms selected from N, O and S, and optionally containing unsaturation;

$R_3$, $R_4$, $R_5$, $R_6$, $R_7$ and $R_8$ are each independently H, unsubstituted or substituted $C_1$-$C_6$ alkyl, or unsubstituted or substituted $C_3$-$C_{10}$ carbocycle optionally containing unsaturation;

$R_{8'}$ is H, unsubstituted or substituted $C_1$-$C_6$ alkyl, —C(O)$R_{11}$, —C(O)O$R_{11}$, —C(O)N$R_{11}R_{12}$, or —S(O)$_2R_{11}$;

$R_9$ and $R_{10}$ are each independently H, unsubstituted or substituted $C_1$-$C_6$ alkyl, or -$T_q$-$R_q$;

$T_q$ is unsubstituted or substituted $C_1$-$C_6$ alkyl linker, or a bond;

$R_q$ is H, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle, or unsubstituted or substituted heterocycle comprising 1 or 2,5- or 6-member rings and 1-4 heteroatoms selected from N, O and S;

$R_{11}$ and $R_{12}$ are each independently H, unsubstituted or substituted $C_1$-$C_6$ alkyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle, or unsubstituted or substituted heterocycle comprising 1 or 2,5- or 6-member rings and 1-4 heteroatoms selected from N, O and S, or -$T_r$-$R_t$;

$T_r$ is unsubstituted or substituted $C_1$-$C_6$ alkyl linker, or a bond;

$R_t$ is H, unsubstituted or substituted $C_1$-$C_6$ alkyl, unsubstituted or substituted $C_6$-$C_{10}$ aryl, unsubstituted or substituted $C_1$-$C_6$ alkoxy, unsubstituted or substituted $C_6$-$C_{10}$ aryloxy, unsubstituted or substituted heteroaryl comprising 1 or 2,5- or 6-member rings and 1-4 heteroatoms selected from N, O and S, unsubstituted or substituted $C_3$-$C_{10}$ carbocycle, unsubstituted or substituted heterocycle comprising 1 or 2,5- or 6-member rings and 1-4 heteroatoms selected from N, O and S, —C(O)O$R_{13}$, or —C(O)$R_{13}$; and $R_{13}$ is H or unsubstituted or substituted $C_1$-$C_6$ alkyl.

2. The compound of claim 1, wherein

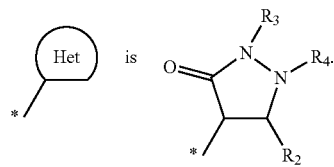

3. The compound of claim 1, wherein

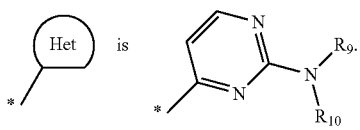

4. The compound of claim 1, wherein said compound is a compound of Formula II or a pharmaceutically acceptable salt, prodrug, or derivative thereof:

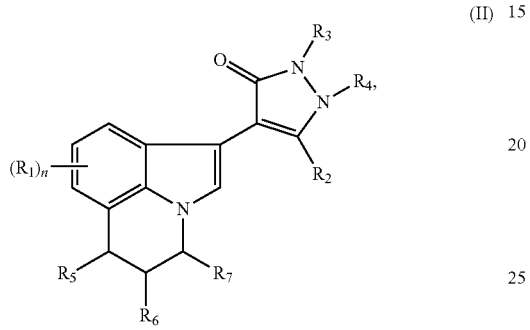

(II)

wherein:
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

$R_2$ is H, unsubstituted or substituted $C_1$-$C_9$ alkyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2,5- or 6-member rings and 1-4 heteroatoms selected from N, O and S, and optionally containing unsaturation, or -$T_r$-$R_r$;

$R_3$, $R_4$, $R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation;

$T_r$ is unsubstituted or substituted $C_1$-$C_6$ alkyl linker, or a bond; and $R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2,5- or 6-member rings and 1-4 heteroatoms selected from N, O and S, and optionally containing unsaturation.

5. The compound of claim 4, wherein $R_2$ is $C_1$-$C_6$ straight chain or $C_3$-$C_6$ branched alkyl substituted with one or more groups, each of which can be the same or different, selected from hydroxyl, halogen, amino, unsubstituted or substituted $C_1$-$C_6$ alkylamino, unsubstituted or substituted di-$C_1$-$C_6$ alkylamino, unsubstituted or substituted $C_1$-$C_6$ alkoxyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2,5- or 6-member rings and 1-4 heteroatoms selected from N, O and S, and optionally containing unsaturation.

6. The compound of claim 4, wherein $R_2$ is unsubstituted or substituted phenyl or naphthyl.

7. The compound of claim 1, wherein said compound is a compound of Formula III, or a pharmaceutically acceptable salt, prodrug, or derivative thereof:

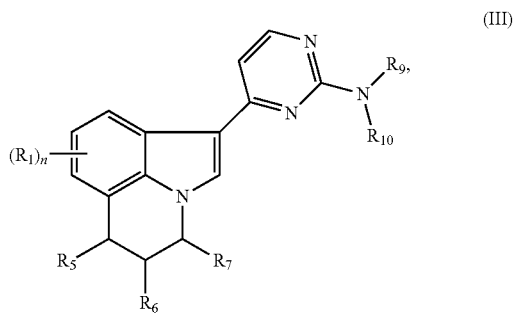

(III)

wherein:
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

$R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation;

$R_9$ and $R_{10}$ are each independently H, unsubstituted or substituted $C_1$-$C_6$ alkyl, or -$T_q$-$R_q$;

$T_q$ is unsubstituted or substituted $C_1$-$C_6$ alkyl linker, or a bond; and $R_q$ is H, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle, or unsubstituted or substituted heterocycle comprising 1 or 2,5- or 6-member rings and 1-4 heteroatoms selected from N, O and S.

8. The compound of claim 7, wherein n is 0.

9. The compound of claim 7, wherein $R_q$ is heterocycle selected from pyrrolidinyl, imidazolidinyl, pyrazolidinyl, oxazolidinyl, isoxazolidinyl, triazolidinyl, tetrahyrofuranyl, piperidinyl, piperazinyl, and morpholinyl, and the like, and is optionally substituted.

10. The compound of claim 7, wherein $R_q$ is piperidinyl.

11. The compound of claim 1, wherein said compound is a compound of Formula IV or a pharmaceutically acceptable salt, prodrug, or derivative thereof:

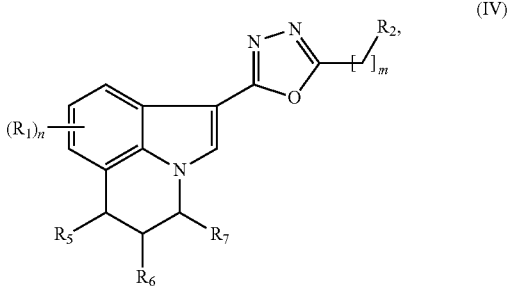

(IV)

wherein:
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ is H, unsubstituted or substituted $C_1$-$C_9$ alkyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2,5- or 6-member rings and 1-4 heteroatoms selected from N, O and S, and optionally containing unsaturation, or -$T_r$-$R_r$;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2,5- or 6-member rings and 1-4 heteroatoms selected from N, O and S, and optionally containing unsaturation; and $R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation.

12. The compound of claim 11, wherein $R_2$ is unsubstituted or substituted phenyl or naphthyl.

13. The compound of claim 11, wherein $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2,5- or 6-member rings and 1-4 heteroatoms selected from N, O and S, and optionally containing unsaturation.

14. The compound of claim 1, wherein said compound is a compound of Formula V or a pharmaceutically acceptable salt, prodrug, or derivative thereof:

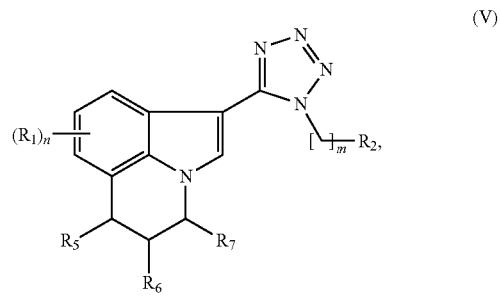

(V)

wherein
n is 0, 1, 2 or 3, and each $R_1$ is independently selected from hydroxyl, unsubstituted or substituted $C_1$-$C_6$ alkyl, unsubstituted or substituted $C_1$-$C_6$ alkoxyl, halogen, cyano, nitro, amino, unsubstituted or substituted $C_1$-$C_6$ alkylamino, and unsubstituted or substituted di-$C_1$-$C_6$ alkylamino;

m is 0, 1, 2, 3, 4, 5 or 6;

$R_2$ is H, unsubstituted or substituted $C_1$-$C_9$ alkyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, unsubstituted or substituted heterocycle comprising 1 or 2,5- or 6-member rings and 1-4 heteroatoms selected from N, O and S, and optionally containing unsaturation, or -$T_r$-$R_r$;

$T_r$ is unsubstituted or substituted $C_1$-$C_6$ alkyl linker, or a bond;

$R_r$ is H, hydroxyl, unsubstituted or substituted $C_1$-$C_6$ alkoxyl, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, or unsubstituted or substituted heterocycle comprising 1 or 2,5- or 6-member rings and 1-4 heteroatoms selected from N, O and S, and optionally containing unsaturation; and $R_5$, $R_6$, and $R_7$ are each independently H, unsubstituted or substituted $C_1$-$C_6$ alkyl, or unsubstituted or substituted $C_3$-$C_{10}$ carbocycle optionally containing unsaturation.

15. The compound of claim 14, wherein $R_2$ is unsubstituted or substituted phenyl or naphthyl.

16. The compound of claim 14, wherein $R_2$ is phenyl or naphthyl substituted with one or more groups, each of which can be the same or different, selected from hydroxyl, halogen, nitro, cyano, unsubstituted or substituted $C_1$-$C_6$ alkyl, unsubstituted or substituted $C_1$-$C_6$ alkoxyl, unsubstituted or substituted $C_6$-$C_{10}$ aryloxyl, unsubstituted or substituted heteroaryloxyl, amino, unsubstituted or substituted $C_1$-$C_6$ alkylamino, unsubstituted or substituted di-$C_1$-$C_6$ alkylamino, unsubstituted or substituted $C_1$-$C_6$ alkylcarbonyl, unsubstituted or substituted $C_1$-$C_6$ alkoxylcarbonyl, unsubstituted or substituted $C_6$-$C_{10}$ arylcarbonyl, unsubstituted or substituted $C_1$-$C_6$ alkylaminocarbonyl, unsubstituted or substituted di-$C_1$-$C_6$ alkylaminocarbonyl, unsubstituted or substituted $C_6$-$C_{10}$ arylaminocarbonyl, unsubstituted or substituted $C_6$-$C_{10}$ aryl, unsubstituted or substituted heteroaryl comprising 1 or 2,5- or 6-member rings and 1-4 heteroatoms selected from N, O and S, unsubstituted or substituted $C_3$-$C_{10}$ carbocycle optionally containing unsaturation, and unsubstituted or substituted heterocycle comprising 1 or 2,5- or 6-member rings and 1-4 heteroatoms selected from N, O and S, and optionally containing unsaturation.

17. A pharmaceutical composition comprising a compound of claim 1 and one or more pharmaceutically acceptable carriers.

\* \* \* \* \*